US012678495B2

(12) United States Patent
Follmann et al.

(10) Patent No.: US 12,678,495 B2
(45) **Date of Patent: *Jul. 14, 2026**

(54) **VACCINES AGAINST *CHLAMYDIA* SP**

(71) Applicant: STATENS SERUM INSTITUT, Copenhagen (DK)

(72) Inventors: Frank Follmann, Soborg (DK); Ida Rosenkrands, Vaerlose (DK); Anja Olsen, Soborg (DK); Peter Andersen, Bronshoj (DK)

(73) Assignee: STATENS SERUM INSTITUT, Copenhagen S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 19/197,254

(22) Filed: May 2, 2025

(65) Prior Publication Data

US 2025/0255951 A1      Aug. 14, 2025

Related U.S. Application Data

(60) Division of application No. 17/155,264, filed on Jan. 22, 2021, which is a continuation of application No. 15/956,731, filed on Apr. 18, 2018, now Pat. No. 10,925,954, which is a continuation of application No. 14/216,403, filed on Mar. 17, 2014, now abandoned.

(60) Provisional application No. 61/802,907, filed on Mar. 18, 2013.

(30) Foreign Application Priority Data

Mar. 18, 2013    (DK) ................................. 2013 00155
Dec. 11, 2013    (DK) ................................. 2013 00684

(51) Int. Cl.
*C07K 14/295*        (2006.01)
*A61K 39/00*         (2006.01)
*A61K 39/118*        (2006.01)

(52) U.S. Cl.
CPC .......... *A61K 39/118* (2013.01); *C07K 14/295* (2013.01); *A61K 2039/6031* (2013.01); *C07K 2319/40* (2013.01)

(58) Field of Classification Search
CPC .......... A61K 39/118; A61K 2039/6031; C07K 14/295; C07K 2319/40
See application file for complete search history.

(56) References Cited

U.S. PATENT DOCUMENTS

| | | |
|---|---|---|
| 5,869,608 A | 2/1999 | Caldwell et al. |
| 6,384,206 B1 | 5/2002 | Caldwell et al. |
| 6,680,182 B1 | 1/2004 | Khan et al. |
| 2009/0214570 A1 | 8/2009 | Mrsny et al. |
| 2009/0304722 A1 | 12/2009 | Theisen et al. |

FOREIGN PATENT DOCUMENTS

| | | |
|---|---|---|
| WO | 94/06827 A1 | 3/1994 |
| WO | 1997/006263 A1 | 2/1997 |
| WO | 2011/147975 A1 | 12/2011 |
| WO | 2012/172042 A1 | 12/2012 |

OTHER PUBLICATIONS

Chinese Office Action, dated Jun. 27, 2024, issued in corresponding CN Patent Application No. 2021104074428.

Anttila, et al., Serotypes of Chlamydia trachomatis and risk for development of cervical squamous cell carcinoma, JAMA, Jan. 3, 2001, 285(1): 47-51.

Baehr, et al., Mapping antigenic domains expressed by Chlamydia trachomatis major outer membrane protein genes, Proc Natl Acad Sci USA., Jun. 1988, 85(11): 4000-4004.

Bandea, et al., Chlamydia trachomatis serovars among strains isolated from members of rural indigenous communities and urban populations in Australia, J Clin Microbiol., Jan. 2008, 46(1): 355-356.

Batteiger, et al., Protective immunity to Chlamydia trachomatis genital infection: evidence from human studies, J Infect Dis., Jun. 15, 2010, 201 Suppl 2: S178-S189.

Batteiger, et al., Species-, serogroup-, and serovar-specific epitopes are juxtaposed in variable sequence region 4 of the major outer membrane proteins of some Chlamydia trachomatis serovars, Infect Immun., Jul. 1996, 64(7):2839-2841.

Batteiger, et al., The major outer membrane protein of a single Chlamydia trachomatis serovar can possess more than one serovar-specific epitope, Infect Immun., Feb. 1996, 64(2):542-547.

Bavoil, et al., Role of disulfide bonding in outer membrane structure and permeability in Chlamydia trachomatis, Infect Immun., May 1984, 44(2): 479-485.

Brunham, et al., Immunology of Chlamydia infection: implications for a Chlamydia trachomatis vaccine, Nat Rev Immunol., Feb. 2005, 5(2): 149-161.

Caldwell, et al., Neutralization of Chlamydia trachomatis infectivity with antibodies to the major outer membrane protein, Infect Immun., Nov. 1982, 38(2): 745-754.

Caldwell, et al., Purification and partial characterization of the major outer membrane protein of Chlamydia trachomatis, Infect Immun., Mar. 1981, 31(3): 1161-1176.

Carmichael, et al., Induction of protection against vaginal shedding and infertility by a recombinant Chlamydia vaccine, Vaccine, Jul. 18, 2011, 29(32): 5276-5283—author manuscript format submitted (available in PMC Jul. 18, 2012—18 pp.).

(Continued)

*Primary Examiner* — Erinne R Dabkowski
(74) *Attorney, Agent, or Firm* — Howson & Howson, LLP; Kathleen D. Rigaut; Richard F. Kane

(57) ABSTRACT

The present invention describes an efficient vaccine against a *Chlamydia trachomatis* (Ct). The vaccine is based on recombinant fusion molecules that are capable of generating a high titered neutralizing antibody response that is protective against various Ct serovars. Our invention furthermore describe the combination of these antibody promoting fragments with Ct antigens that are targets for T cells with the aim to provide a vaccine that activate both arms of the immune system.

16 Claims, 28 Drawing Sheets

Specification includes a Sequence Listing.

(56)                    References Cited

OTHER PUBLICATIONS

Cheng, et al., Characterization of the humoral response induced by a peptide corresponding to variable domain IV of the major outer membrane protein of Chlamydia trachomatis serovar E, Infect Immun., Aug. 1992, 60(8):3428-3432.

Coler, et al., Identification and characterization of novel recombinant vaccine antigens for immunization against genital Chlamydia trachomatis, FEMS Immunol Med Microbiol., Mar. 2009, 55(2): 258-270—author manuscript format submitted (available in PMC Mar. 1, 2010—19 pp.).

Cotter, et al.., Protective efficacy of major outer membrane protein-specific immunoglobulin A (IgA) and IgG monoclonal antibodies in a murine model of Chlamydia trachomatis genital tract infection, Infect Immun., Dec. 1995, 63(12): 4704-4714.

Crane, et al., Chlamydia trachomatis polymorphic membrane protein D is a species-common pan-neutralizing antigen, Proc Natl Acad Sci USA., Feb. 7, 2006, 103(6): 1894-1899.

Darville, et al., Pathogenesis of genital tract disease due to Chlamydia trachomatis, J Infect Dis., Jun. 15, 2010, 201 Suppl 2: S114-S125—author manuscript format submitted (available in PMC Aug. 4, 2011—18 pp.).

Farris, et al., Vaccination against Chlamydia genital infection utilizing the murine C. muridarum model, Infect Immun., Mar. 2011, 79(3): 986-996.

Findlay, et al., Surface expression, single-channel analysis and membrane topology of recombinant Chlamydia trachomatis Major Outer Membrane Protein, BMC Microbiol., Jan. 26, 2005, 5:5, 15 pp.

Follmann, et al., Antigenic profiling of a Chlamydia trachomatis gene-expression library, J Infect Dis., Mar. 15, 2008 edition, published electronically on Feb. 20, 2008, 197 (6):897-905.

Golden, et al., Duration of untreated genital infections with chlamydia trachomatis: a review of the literature, Sex Transm Dis., Jul. 2000, 27(6): 329-337.

Hansen, et al., Liposome Delivery of Chlamydia muridarum Major Outer Membrane Protein Primes a Th1 Response That Protects against Genital Chlamydial Infection in a Mouse Model, J Infect Dis., electronically published Jul. 24, 2008, 198(5): 758-767.

Harboe, et al., Evidence for occurrence of the ESAT-6 protein in Mycobacterium tuberculosis and virulent Mycobacterium bovis and for its absence in Mycobacterium bovis BCG, Infect Immun., Jan. 1996, 64(1): 16-22.

Hatch, et al., Structural and polypeptide differences between envelopes of infective and reproductive life cycle forms of *Chlamydia* spp., J Bacteriol., Jan. 1984, 157(1): 13-20.

Hinton, et al., Pattern recognition by B cells: the role of antigen repetitiveness versus Toll-like receptors. Current topics in microbiology and immunology, 2008, 319: 1-15—pp. 1-5 provided.

Hsu, et al., Genotyping of Chlamydia trachomatis from clinical specimens in Taiwan, J Med Microbiol., Mar. 2006, 55(Pt 3): 301-308.

Jonsdottir, et al., The molecular epidemiology of genital Chlamydia trachomatis in the greater Reykjavik area, Iceland, Sex Transm Dis., Mar. 2003, 30(3): 249-256.

Kalbina, et al., A novel chimeric MOMP antigen expressed in *Escherichia coli, Arabidopsis thaliana*, and Daucus carota as a potential Chlamydia trachomatis vaccine candidate, Protein Expression and Purification, Dec. 2011, 80(2):194-202.

Kaltenboeck, et al., Structures of and allelic diversity and relationships among the major . . . , J Bacteriol., Jan. 1993, 175(2): 487-502.

Kang, et al., Processing and Reactivity of T Cell Epitopes Containing Two Cysteine Residues from Hen Egg-White Lysozyme (HEL74-90), J. Immunol., Feb. 2000, 164 (4) 1775-1782.

Kari, et al., Chlamydia trachomatis native major outer membrane protein induces partial protection in nonhuman primates: implication for a trachoma transmission-blocking vaccine, J Immunol., Jun. 15, 2009, 182(12): 8063-8070.

Karunakaran, et al., Immunoproteomic discovery of novel T cell antigens from the obligate intracellular pathogen Chlamydia, J Immunol., Feb. 15, 2008, 180(4): 2459-2465.

Kawa, et al., Immune response to the Chlamydia trachomatis outer membrane protein PorB, Vaccine, Oct. 2004, 22(31-32):4282-4286.

Kim, et al., Epitope clusters in the major outer membrane protein of Chlamydia trachomatis, Curr Opin Immunol., Aug. 2001, 13(4): 429-436.

Kubo, et al., Characterization and functional analysis of PorB, a Chlamydia porin and neutralizing target, Mol Microbiol., Nov. 2000, 38(4): 772-780.

Li, et al., Immunization with a combination of integral chlamydial antigens and a defined secreted protein induces robust immunity against genital chlamydial challenge, Infect Immun., Sep. 2010, 78(9): 3942-3949.

Lysen, et al., Characterization of ompA genotypes by sequence analysis of DNA from all detected cases of Chlamydia trachomatis infections during 1 year of contact tracing in a Swedish County, J Clin Microbiol., Apr. 2004, 42(4): 1641-1647.

Millman, et al. Population-based genetic and evolutionary analysis of Chlamydia trachomatis urogenital strain variation in the United States, J Bacteriol., Apr. 2004, 186(8): 2457-2465.

Molina, et al., Identification of immunodominant antigens of Chlamydia trachomatis using proteome microarrays, Vaccine Apr. 9, 2010, 28(17): 3014-3024—author manuscript format submitted (available in PMC Apr. 9, 2011—21 pp.).

Moore, et al., Fc receptor-mediated antibody regulation of T cell immunity against intracellular pathogens, J Infect Dis., electronically published Mar. 17, 2003, 188(4): 617-624.

Morrison, et al., Immunity to murine Chlamydia trachomatis genital tract reinfection involves B cells and CD4(+) T cells but not CD8(+) T cells, Infect Immun., Dec. 2000, 68(12): 6979-6987.

Morrison, et al., Resolution of secondary Chlamydia trachomatis genital tract infection in immune mice with depletion of both CD4+ and CD8+ T cells, Infect Immun., Apr. 2001, 69(4): 2643-2649.

Morrison, et al., Immunity to murine chlamydial genital infection, Infect Immun., Jun. 2002, 70(6): 2741-2751.

Motin, et al., Immunization with a peptide corresponding to chlamydial heat shock protein 60 increases the humoral immune response in C3H mice to a peptide representing variable domain 4 of the major outer membrane protein of Chlamydia trachomatis, Clin Diagn Lab Immunol., May 1999, 6(3): 356-363.

Murdin, et al., A poliovirus hybrid expressing a neutralization epitope from the major outer membrane protein of Chlamydia trachomatis is highly immunogenic, Infect Immun., Oct. 1993, 61(10): 4406-4414.

Murdin, et al., Poliovirus hybrids expressing neutralization epitopes from variable domains I and IV of the major outer membrane protein of Chlamydia trachomatis elicit broadly cross-reactive C. trachomatis-neutralizing antibodies, Infect Immun., Mar. 1995, 63(3): 1116-1121.

Mygind, et al., Detection of Chlamydia trachomatis-specific antibodies in human sera by recombinant major outer-membrane protein polyantigens, J Med Microbiol., May 2000, 49(5): 457-465.

Nunez, et al., Dominant Antigen Reveals Distinct Evolutionary Scenarios for B- and T-cell Epitopes: Worldwide Survey, PLOS One, Oct. 5, 2010, 5(10):e13171 (10 pp.).

Olsen, et al., Identification of CT521 as a frequent target of Th1 cells in patients with urogenital Chlamydia trachomatis infection, J Infect Dis., electronically published Sep. 22, 2006, 194(9): 1258-1266.

Olsen, et al., Identification of human T-cell targets recognized during the Chlamydia trachomatis genital infection, J Infect Dis., electronically published Oct. 31, 2007, 196: 1546-1552.

Olsen, et al., Protection against Chlamydia promoted by a subunit vaccine (CTH1) compared with a primary intranasal infection in a mouse genital challenge model, PLoS One, May 21, 2010, 5(5): e10768 (11 pp.).

Paavonen, et al., Chlamydia trachomatis: impact on human reproduction, Hum Reprod Update., Sep. 1999, 5(5): 433-447.

Pal, et al., Vaccination of mice with DNA plasmids coding for the Chlamydia trachomatis major outer membrane protein elicits an immune response but fails to protect against a genital challenge, Vaccine, Feb. 5, 1999, 17(5): 459-465.

(56)        References Cited

OTHER PUBLICATIONS

Pal, et al., Immunogenic and protective ability of the two developmental forms of Chlamydiae in a mouse model of infertility, Vaccine, Nov. 12, 1999, 18(7-8): 752-761.

Pal, et al., Immunization with the Chlamydia trachomatis mouse pneumonitis major outer membrane protein can elicit a protective immune response against a genital challenge, Infect Immun., Oct. 2001, 69(10): 6240-6247.

Pal, et al., Mapping of a surface-exposed B-cell epitope to the variable sequent 3 of the major outer-membrane protein of Chlamydia trachomatis, J. Gen. Microbiol., Jul. 1993, 139(7):1565-70.

Peeling, et al., In vitro neutralization of Chlamydia trachomatis with monoclonal antibody to an epitope on the major outer membrane protein, Infect Immun., Nov. 1984, 46(2): 484-488.

Peterson, et al., The effect of orientation within a chimeric peptide on the immunogenicity of Chlamydia trachomatis epitopes, Mol Immunol., Mar. 1996, 33(4-5): 335-339.

Plummer, et al., Cofactors in male-female sexual transmission of human immunodeficiency virus type 1, J Infect Dis., Feb. 1991, 163(2): 233-239.

Qu, et al., Characterization of a Neutralizing Monoclonal Antibody Directed at Variable Domain I of the Major Outer Membrane Protein of Chlamydia trachomatis C-Complex Serovars, Infect Imm., Apr. 1993, 61(4):1365-1370.

Qu, et al., Analysis of the humoral response elicited in mice by a chimeric peptide representing variable segments I and IV of the major outer membrane protein of Chlamydia trachomatis, Vaccine, May 1994, 12(6): 557-564.

Rasmussen, Chlamydia immunology, Curr Opin Infect Dis., Feb. 1998, 11(1): 37-41.

Ravn, et al., Human T cell responses to the ESAT-6 antigen from Mycobacterium tuberculosis, J Infect Dis, Mar. 1999, 179(3): 637-645.

Rockey, et al., Chlamydia vaccine candidates and tools for chlamydial antigen discovery, Expert Rev Vaccines., Oct. 2009, 8(10):1365-1377.

Sette, et al., Reverse vaccinology: developing vaccines in the era of genomics, Immunity, Oct. 2010, 33(4):530-541—author manuscript format submitted (available in PMC Apr. 6, 2012—23 pp.).

Sharma, et al., Profiling of human antibody responses to Chlamydia trachomatis urogenital tract infection using microplates arrayed with 156 chlamydial fusion proteins, Infect Immun., Mar. 2006, 74(3): 1490-1499.

Shaw, et al., Dendritic cells pulsed with a recombinant chlamydial major outer membrane protein antigen elicit a CD4 (+) type 2 rather than type 1 immune response that is not protective, Infect Immun., Mar. 2002, 70(3): 1097-1105.

Stephens, et al., Diversity of Chlamydia trachomatis major outer membrane protein genes, J Bacteriol., Sep. 1987, 169(9): 3879-3885.

Stephens, et al., High-resolution mapping of serovar-specific and common antigenic determinants of the major outer membrane protein of Chlamydia trachomatis, J Exp Med., Mar. 1, 1988, 167(3): 817-831.

Su, et al., Differential effect of trypsin on infectivity of Chlamydia trachomatis . . . , Infect Immun., Aug. 1988, 56(8): 2094-2100.

Su, et al., Immunogenicity of a chimeric peptide corresponding to T helper and B cell epitopes of the Chlamydia trachomatis major outer membrane protein, J Exp Med., Jan. 1992, 175(1):227-235.

Common T-helper and B-cell neutralizing epitopes of the major outer membrane protein of Chlamydia trachomatis, Vaccine, 1993, 11(11): 1159-1166.

Su, et al., Protective efficacy of a parenterally administered MOMP-derived synthetic oligopeptide vaccine in a murine model of Chlamydia trachomatis genital tract infection: serum neutralizing IgG antibodies do not protect against chlamydial genital tract infection, Vaccine, Aug. 1995, 13(11):1023-1032.

Su, et al., CD4+ T cells play a significant role in adoptive immunity to Chlamydia trachomatis infection of the mouse genital tract, Infect Immun., Sep. 1995, 63(9): 3302-3308.

Tifrea, et al., Vaccination with the Recombinant Major Outer Membrane Protein Elicits Antibodies to the Constant Domains and Induces Cross-Serovar Protection against Intranasal Challenge with Chlamydia trachomatis, Infect. Immun., epub Mar. 11, 2013, 81(5):1741-1750.

Toye, et al., Immunologic characterization of a cloned fragment containing the species-specific epitope from the major outer membrane protein of Chlamydia trachomatis, Infect Immun., Dec. 1990, 58(12): 3909-3913.

Villeneuve, et al., Characterization of the humoral response induced by a synthetic peptide of the major outer membrane protein of Chlamydia trachomatis serovar B, Infect Immun., Aug. 1994, 62(8): 3547-3549.

Villeneuve, et al., Determination of neutralizing epitopes in variable domains I and IV of the major outer-membrane protein from Chlamydia trachomatis serovar K, Microbiology, Sep. 1994, 140 ( Pt 9): 2481-2487.

Volp, et al., Peptide immunization of guinea pigs against Chlamydia psittaci (GPIC agent) infection induces good vaginal secretion antibody response, in vitro neutralization and partial protection against live challenge, Immunol Cell Biol., Jun. 2001, 79(3): 245-250.

Who, Global Prevalence and Incidence of selected Curable Sexually Transmitted Infections: Overview and Estimates, World Health Organization, Geneva, Switzerland, Nov. 2001, 50 pp. (42 numbered pages).

Xu, et al., Protective immunity against Chlamydia trachomatis genital infection induced by a vaccine based on the major outer membrane multi-epitope human papillomavirus major capsid protein L1, Vaccine, Mar. 2011, epub Feb. 12, 2011, 29(15):2672-2678.

Yen, et al., Characterization of the disulfide bonds and free cysteine residues of the Chlamydia trachomatis mouse pneumonitis major outer membrane protein, Biochemistry, Apr. 2005, 44(16):6250-6256.

Yu, et al., Novel Chlamydia muridarum T cell antigens induce protective immunity against lung and genital tract infection in murine models, J Immunol., Feb. 1, 2009, 182(3): 1602-1608—author manuscript format submitted (available in PMC Feb. 1, 2010—18 pp.).

Yuan, et al., Nucleotide and deduced amino acid sequences for the four variable domains . . . , Infect Immun., Apr. 1989, 57(4): 1040-1049.

Zhang, et al., Cloning and sequence analysis of the major outer membrane protein genes . . . , Infect Immun., May 1989, 57(5): 1621-1625.

Zhang, et al., Protective monoclonal antibodies recognize epitopes located on the major outer membrane protein of Chlamydia trachomatis, J Immunol., Jan. 15, 1987, 138(2): 575-581.

Zhang, et al., Protective monoclonal antibodies to Chlamydia trachomatis serovar- and serogroup-specific major outer membrane protein determinants, Infect Immun., Feb. 1989, 57(2): 636-638.

Zhang, et al., Characterization of immune responses following intramuscular DNA immunization with the MOMP gene of Chlamydia trachomatis mouse pneumonitis strain, Immunology, Feb. 1999, 96(2): 314-321.

International Search Report mailed Jul. 24, 2014 in International Patent Application No. PCT/DK2014/000015, which application shares common priority with the present application.

Written Opinion mailed Jul. 24, 2014 in International Patent Application No. PCT/DK2014/000015, which application shares common priority with the present application.

Sep. 24, 2014 Letter accompanying the Article 34 Claim Amendments and comments to the Written Opinion in International Patent Application No. PCT/DK2014/000015, which application shares common priority with the present application.

Sep. 24, 2014 Article 34 Claim Amendments in International Patent Application No. PCT/DK2014/000015, which application shares common priority with the present application.

Office Action issued Jun. 16, 2020 (drafted Jun. 2, 2020) in counterpart Japanese Patent Application No. 2019-052389.

Decision of Refusal dated Apr. 30, 2021, in counterpart Japanese Patent Application No. 2019-052389.

(56)     References Cited

OTHER PUBLICATIONS

Appeal dated Sep. 13, 2021, in counterpart Japanese Patent Application No. 2019-052389.
Meoni, et al., CT043, a Protective Antigen That Induces a CD4+ Th1 Response during Chlamydia trachomatis Infection in Mice and Humans, Infection and Immunity, Sep. 2009, 77(9): 4168-4176.

Figure 2

Variable domain (VD4)

```
SvD  VD4ext  NMFTPYIGVKWSRASFDADTIRIAQPKSATAIFDTTTLNPTIAGAGDVK-TGAEGQLGDTMQIVSLQLN
SvE  VD4ext  ........................................................-AS.....................
SvE  VD4ext  ...............S...........RLV.PVV.I..C.S.AGANT...IS....................
SvG  VD4ext  ...............SN..........L.KPVV.I..C.S.VAANS...IS....................
SvI  VD4ext  .........V.................L.E..L.V..K.T.VSS-.NE.A....................
SvJ  VD4ext  .........V.................L.E..L.V..K.T.VAS.S.ND.A...................
```

Conserved epitope

Figure 7 A)

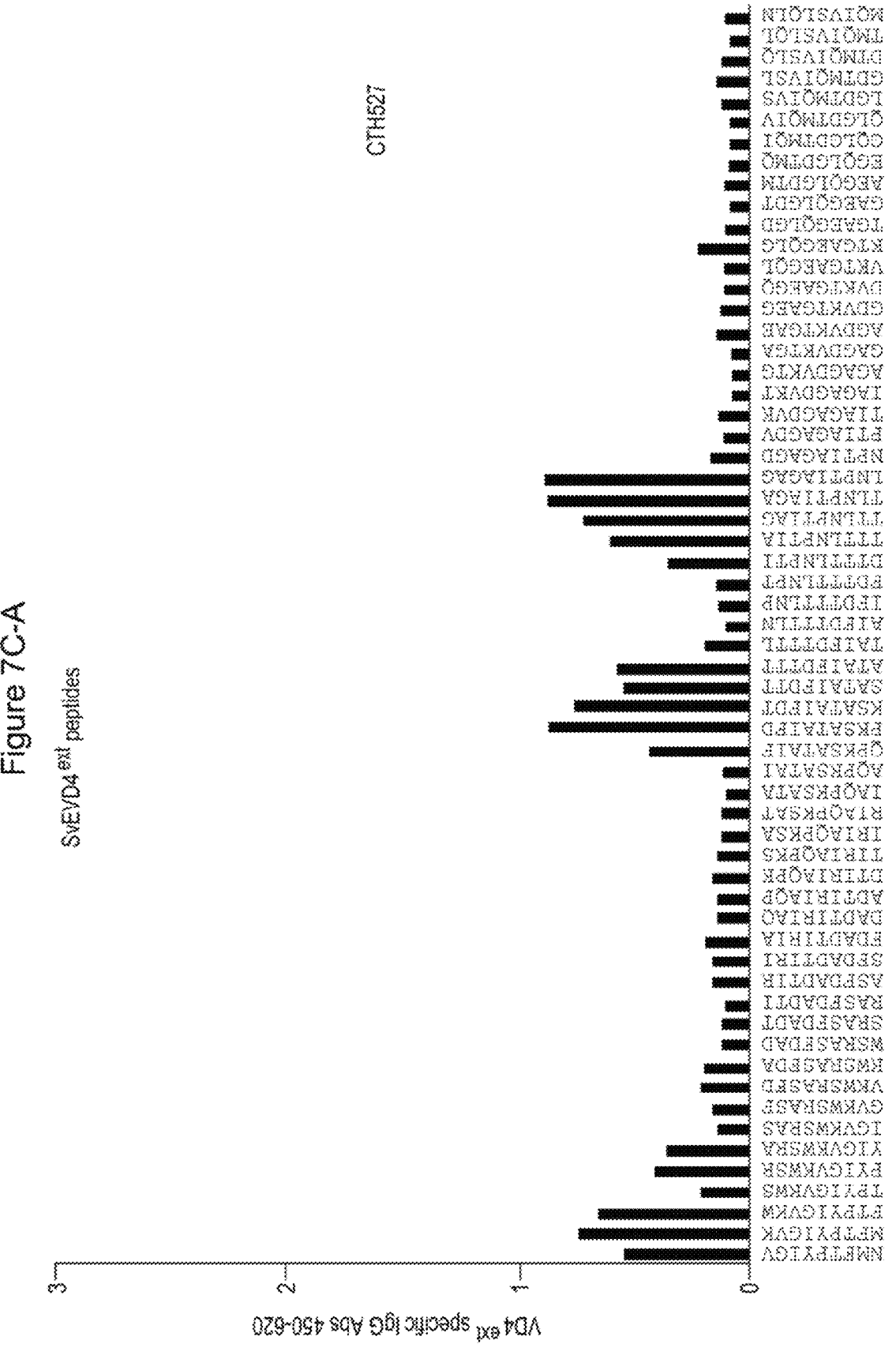
Figure 7C-A

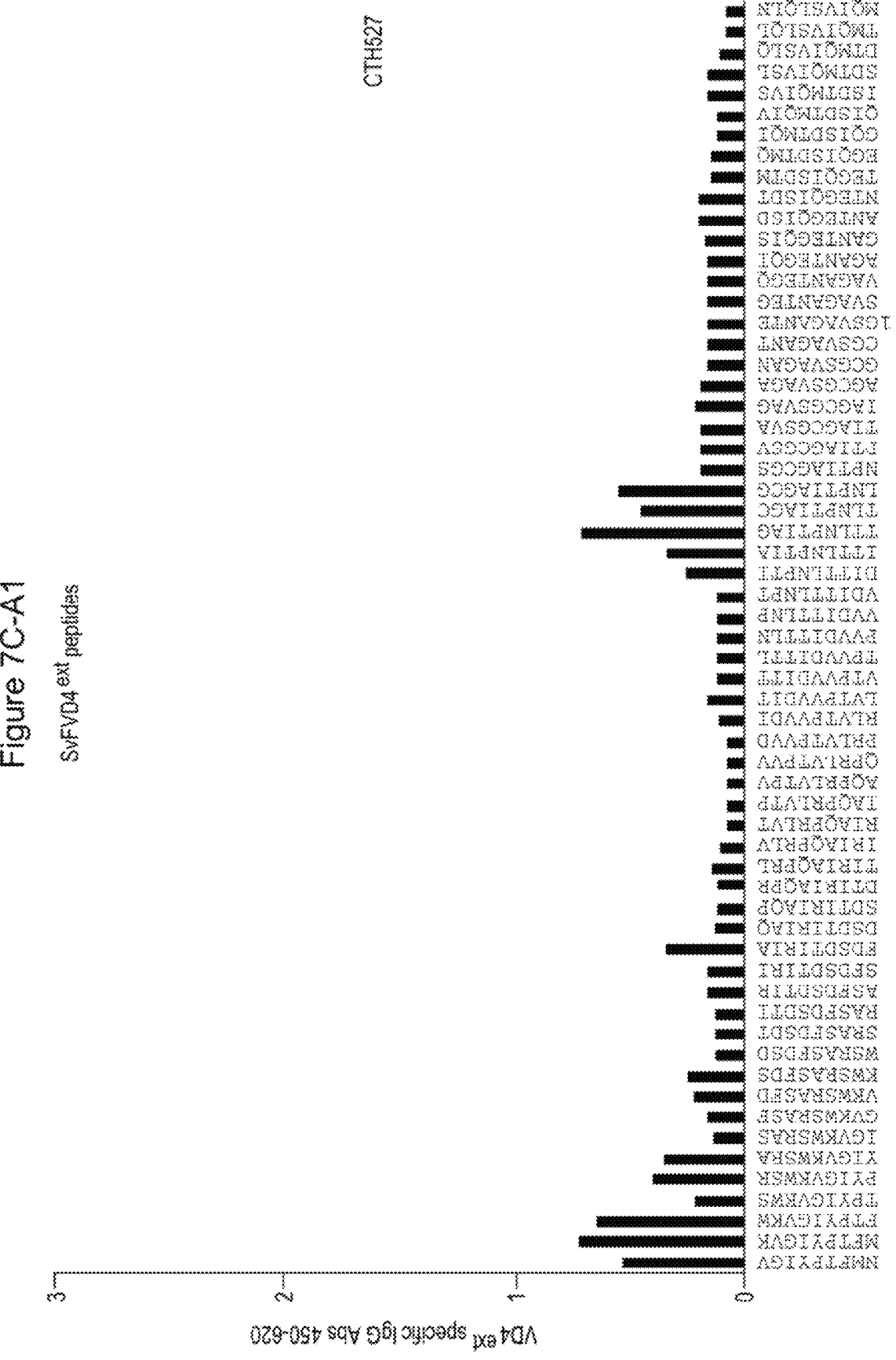
Figure 7C-A1

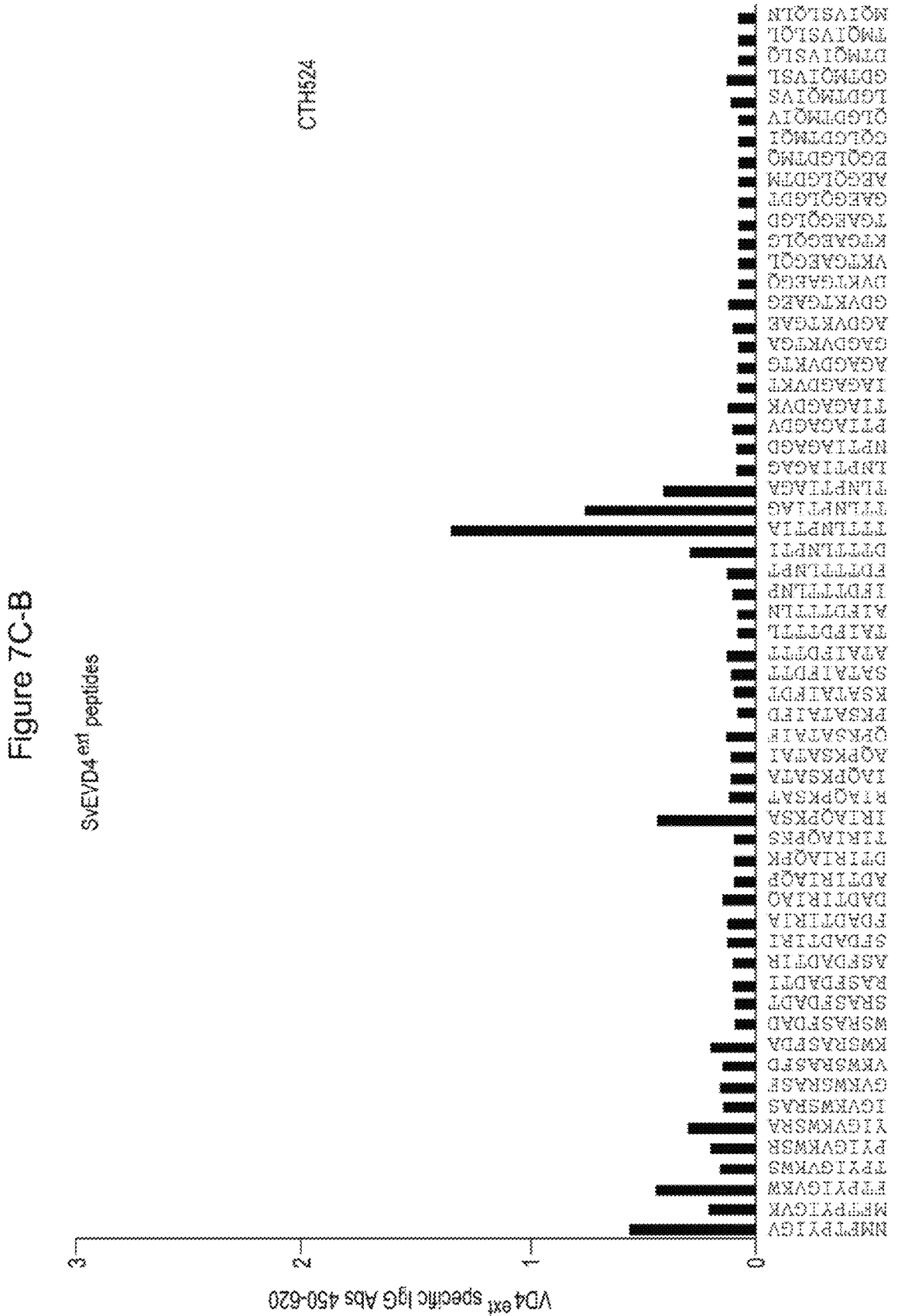
Figure 7C-B

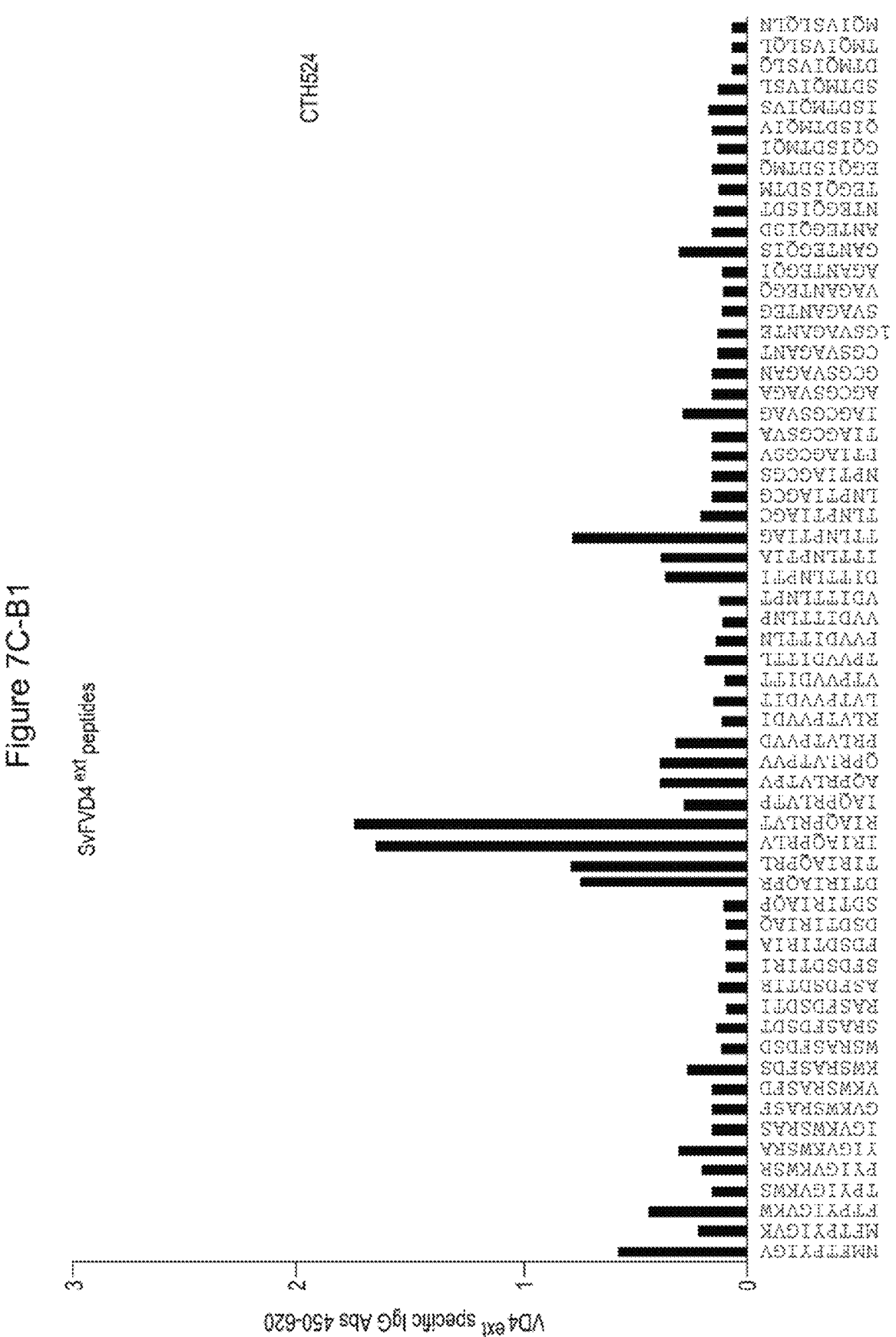
Figure 7C-B1

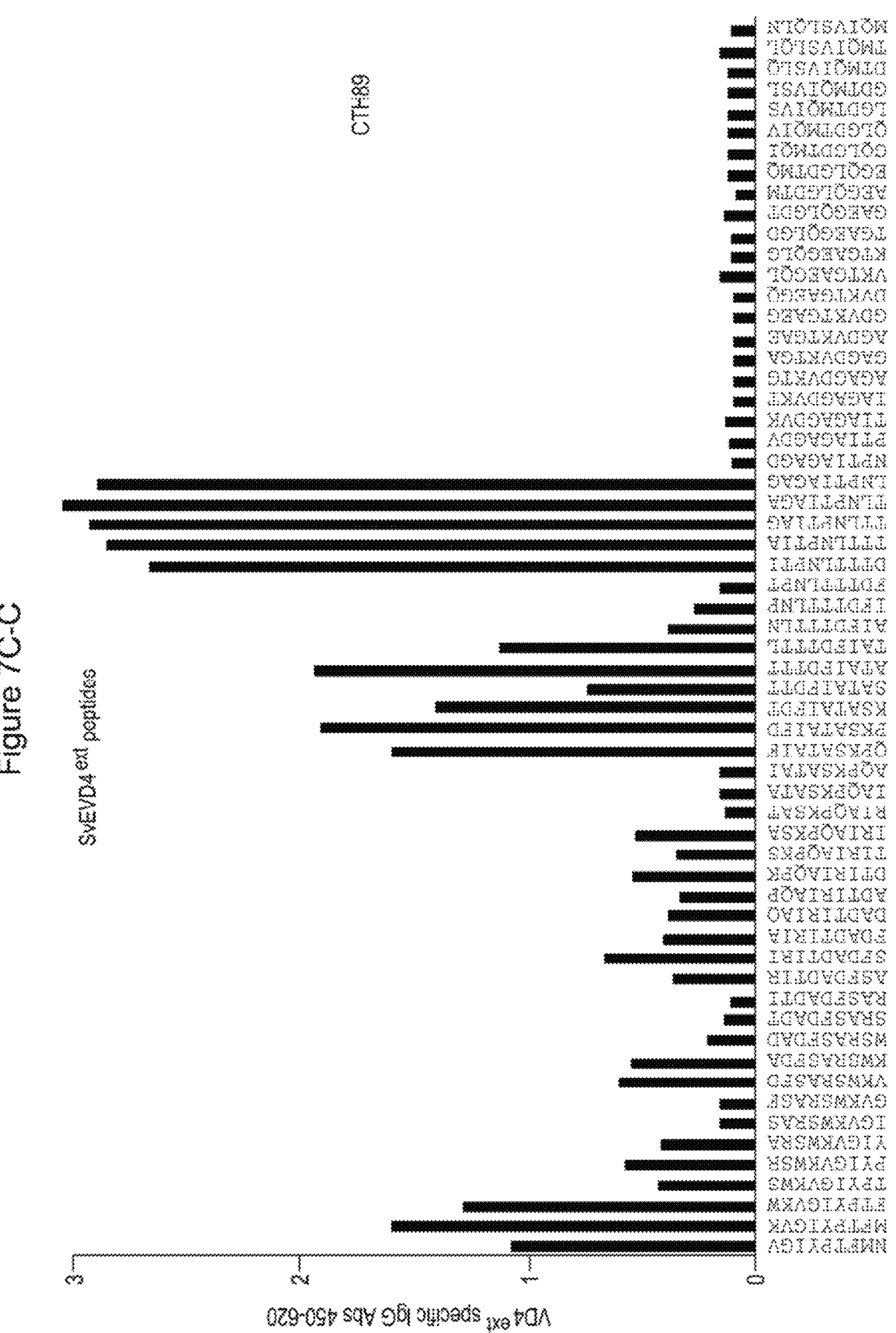
Figure 7C-C

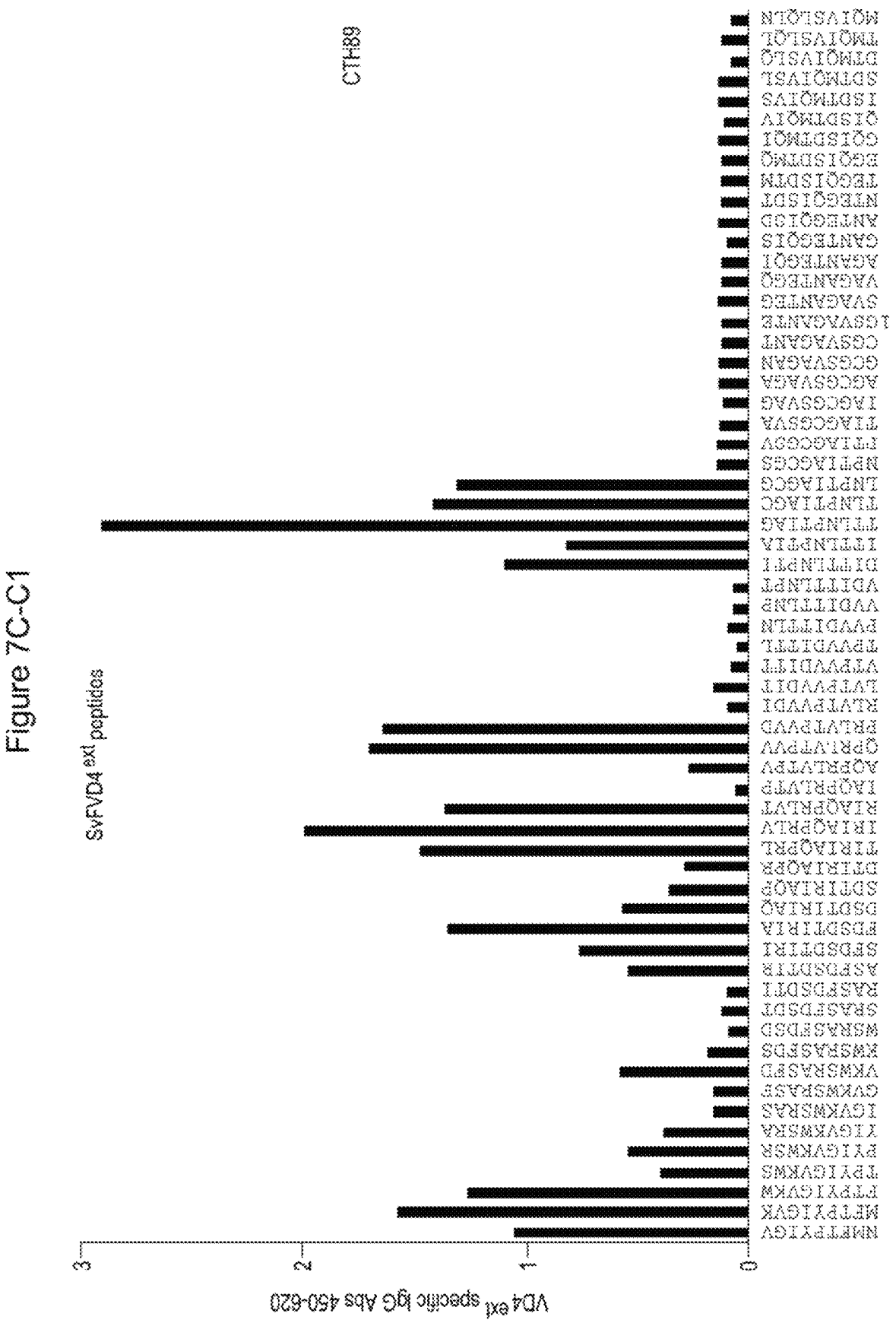
Figure 7C-C1

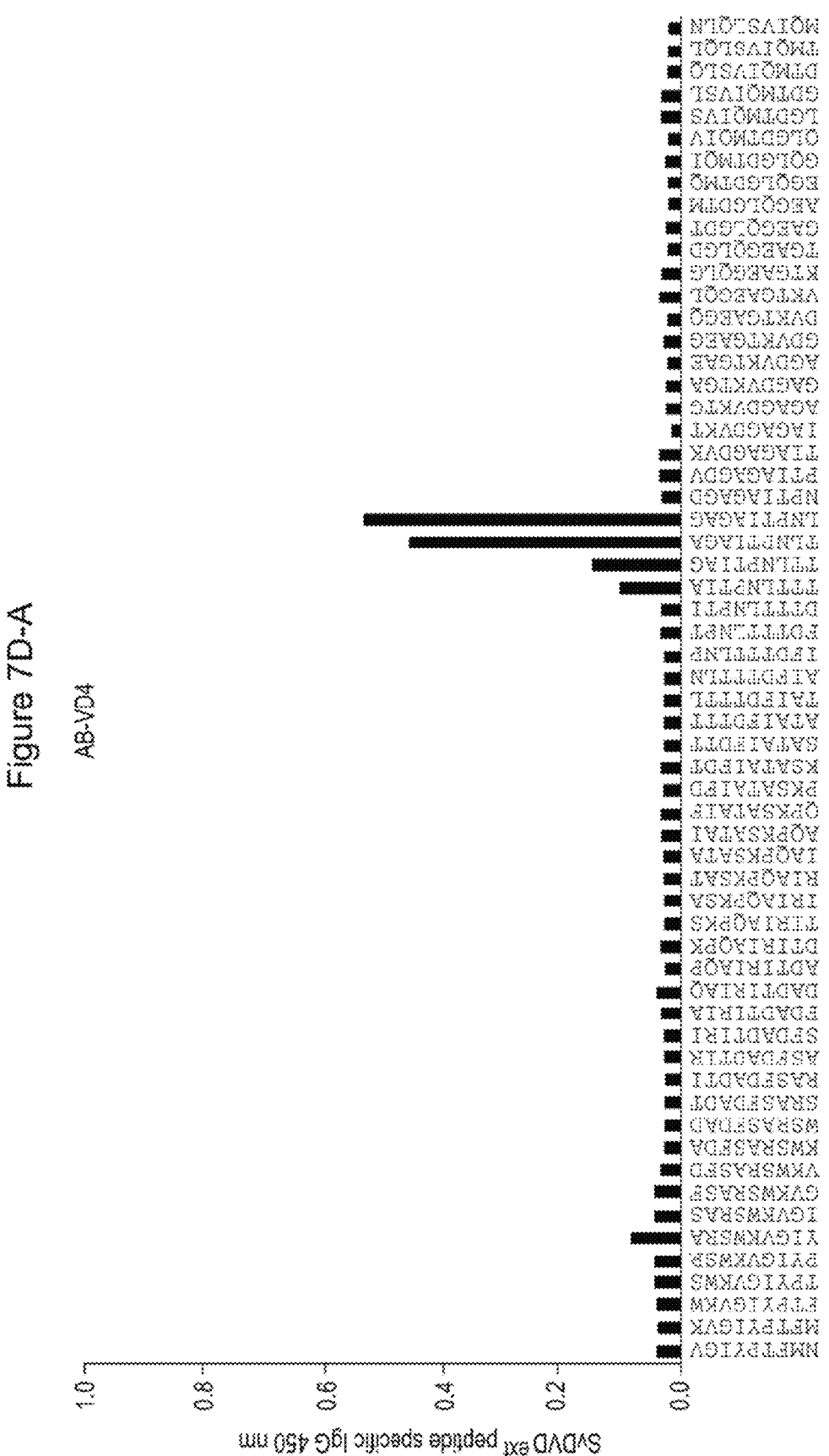
Figure 7D-A

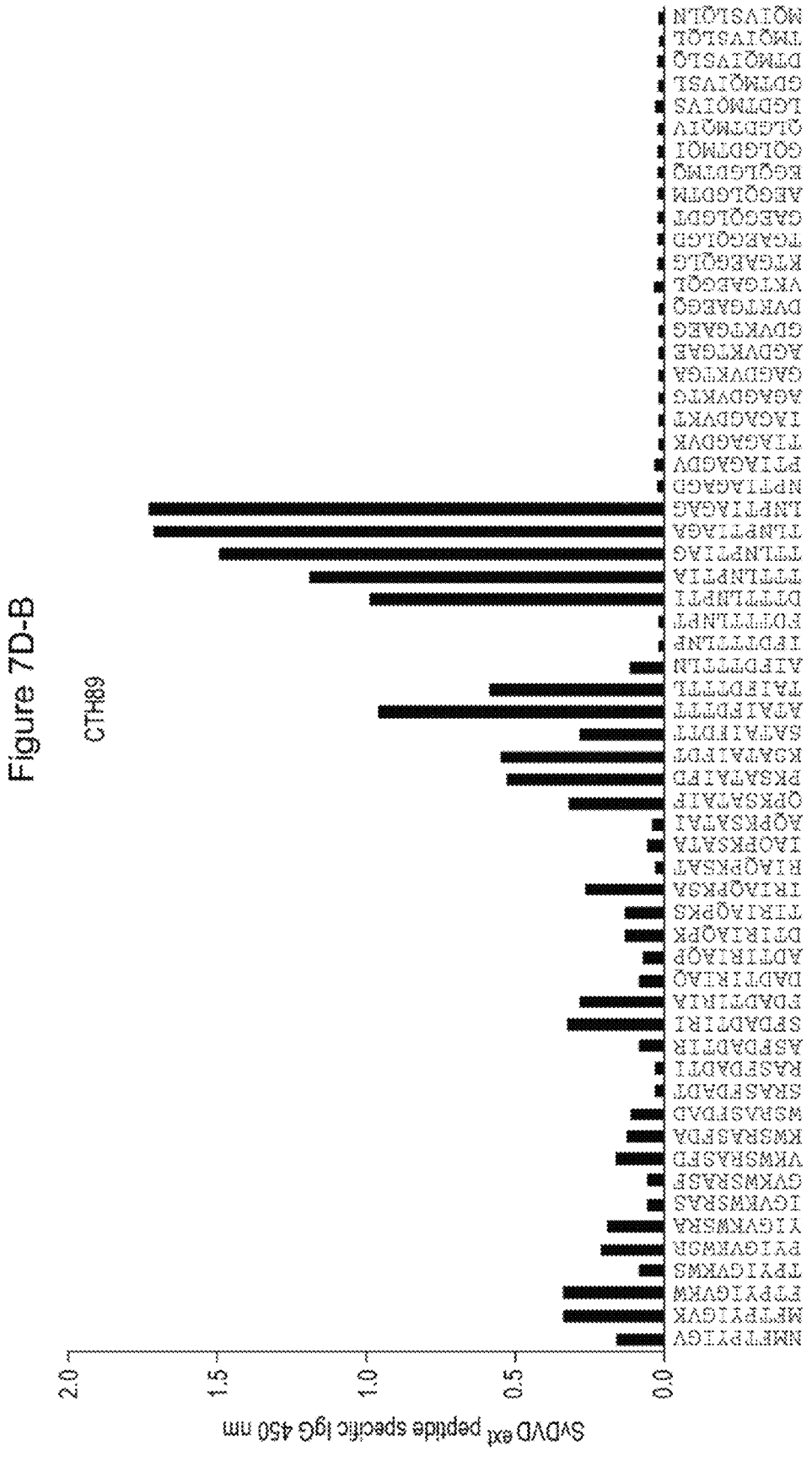
Figure 7D-B

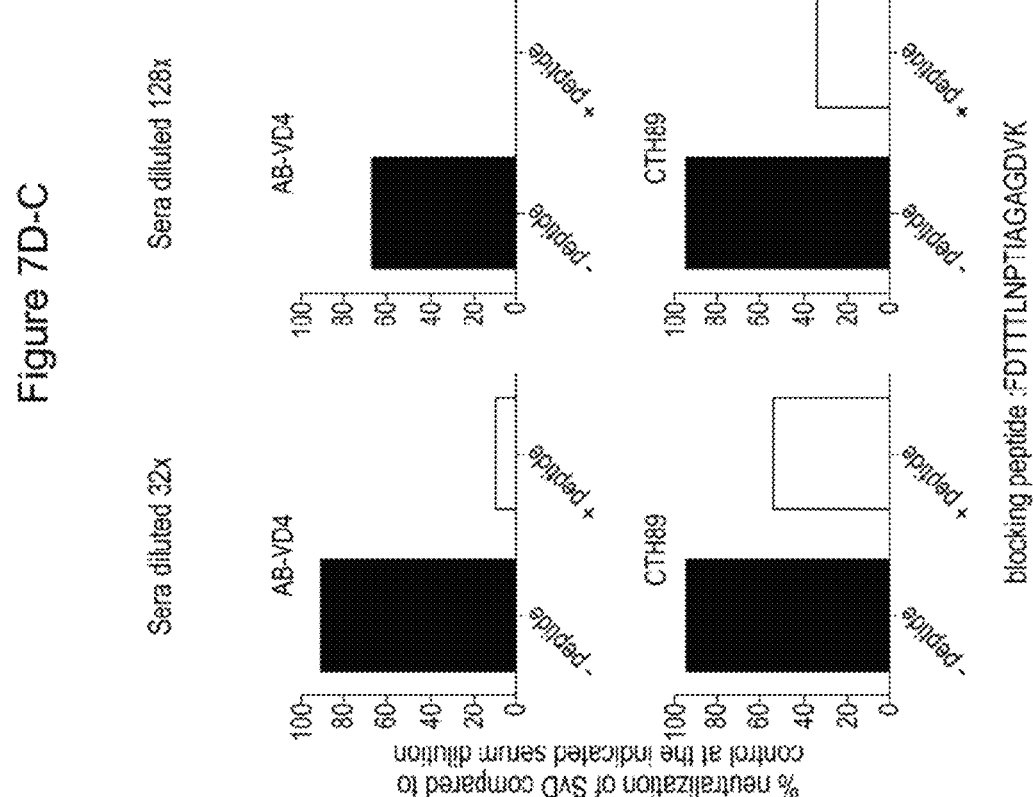
Figure 7D-C

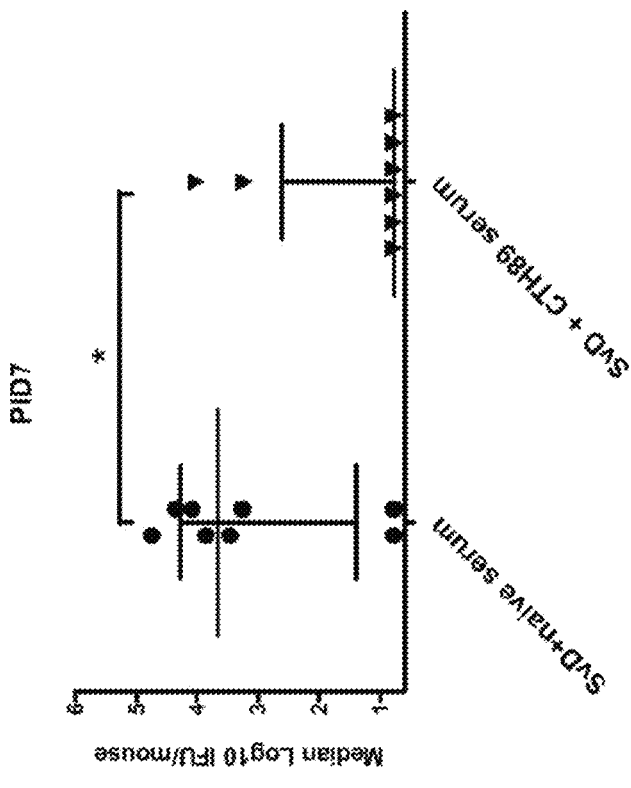
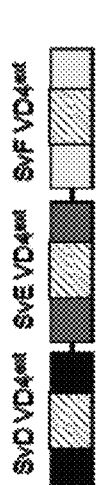
Figure 9

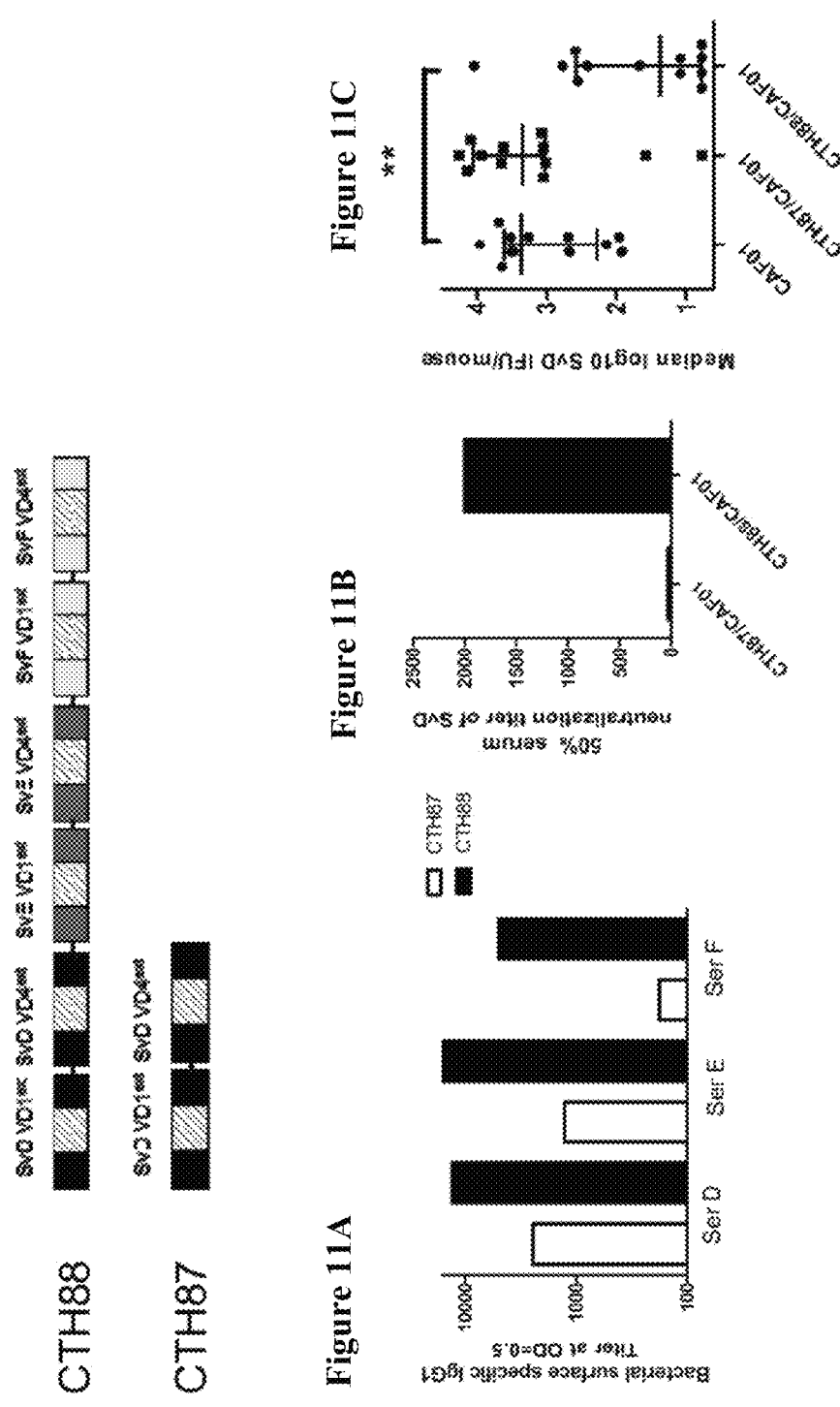

SEQUENCE LISTING

```
Sequence total quantity: 255
SEQ ID NO: 1            moltype = AA  length = 20
FEATURE                 Location/Qualifiers
source                  1..20
                        mol_type = protein
                        organism = Chlamydia trachomatis
SEQUENCE: 1
AKPTTDTGNS AAPSTLTARE                                              20

SEQ ID NO: 2            moltype = AA  length = 20
FEATURE                 Location/Qualifiers
source                  1..20
                        mol_type = protein
                        organism = Chlamydia trachomatis
SEQUENCE: 2
DKPTSTTGNA TAPTTLTARE                                              20

SEQ ID NO: 3            moltype = AA  length = 21
FEATURE                 Location/Qualifiers
source                  1..21
                        mol_type = protein
                        organism = Chlamydia trachomatis
SEQUENCE: 3
EALAGASGNT TSTLSKLVER T                                            21

SEQ ID NO: 4            moltype = AA  length = 21
FEATURE                 Location/Qualifiers
source                  1..21
                        mol_type = protein
```

-continued

```
                         organism = Chlamydia trachomatis
SEQUENCE: 4
EALAGASGNT TSTLSKLVER T                                                    21

SEQ ID NO: 5            moltype = AA  length = 22
FEATURE                 Location/Qualifiers
source                  1..22
                        mol_type = protein
                        organism = Chlamydia trachomatis
SEQUENCE: 5
AAPTTKDIAG LENDPTTNVA RP                                                   22

SEQ ID NO: 6            moltype = AA  length = 22
FEATURE                 Location/Qualifiers
source                  1..22
                        mol_type = protein
                        organism = Chlamydia trachomatis
SEQUENCE: 6
AAPTTSDVAG LQNDPTTNVA RP                                                   22

SEQ ID NO: 7            moltype = AA  length = 30
FEATURE                 Location/Qualifiers
source                  1..30
                        mol_type = protein
                        organism = Chlamydia trachomatis
SEQUENCE: 7
DAISMRVGYY GDFVFDRVLK TDVNKEFQMG                                           30

SEQ ID NO: 8            moltype = AA  length = 18
FEATURE                 Location/Qualifiers
source                  1..18
                        mol_type = protein
                        organism = Chlamydia trachomatis
SEQUENCE: 8
NPAYGRHMQD AEMFTNAA                                                        18

SEQ ID NO: 9            moltype = AA  length = 59
FEATURE                 Location/Qualifiers
source                  1..59
                        mol_type = protein
                        organism = Chlamydia trachomatis
SEQUENCE: 9
AISMRVGYYG DFVFDRVLKT DVNKEFQMGA KPTTDTGNSA APSTLTAREN PAYGRHMQD    59

SEQ ID NO: 10           moltype = AA  length = 59
FEATURE                 Location/Qualifiers
source                  1..59
                        mol_type = protein
                        organism = Chlamydia trachomatis
SEQUENCE: 10
AISMRMGYYG DFVFDRVLKT DVNKEFQMGD KPTSTTGNAT APTTLTAREN PAYGRHMQD    59

SEQ ID NO: 11           moltype = AA  length = 60
FEATURE                 Location/Qualifiers
source                  1..60
                        mol_type = protein
                        organism = Chlamydia trachomatis
SEQUENCE: 11
AISMRMGYYG DFVFDRVLKT DVNKEFEMGE ALAGASGNTT STLSKLVERT NPAYGKHMQD   60

SEQ ID NO: 12           moltype = AA  length = 60
FEATURE                 Location/Qualifiers
source                  1..60
                        mol_type = protein
                        organism = Chlamydia trachomatis
SEQUENCE: 12
AISMRMGYYG DFVFDRVLKT DVNKEFEMGE ALAGASGNTT STLSKLVERT NPAYGKHMQD   60

SEQ ID NO: 13           moltype = AA  length = 61
FEATURE                 Location/Qualifiers
source                  1..61
                        mol_type = protein
                        organism = Chlamydia trachomatis
SEQUENCE: 13
AISMRMGYYG DFVFDRVLKT DVNKEFQMGA APTTKDIAGL ENDPTTNVAR PNPAYGKHMQ   60
D                                                                  61

SEQ ID NO: 14           moltype = AA  length = 61
FEATURE                 Location/Qualifiers
```

-continued

```
source                  1..61
                        mol_type = protein
                        organism = Chlamydia trachomatis
SEQUENCE: 14
AISMRMGYYG DFVFDRVLKT DVNKEFQMGA APTTSDVAGL QNDPTTNVAR PNPAYGKHMQ  60
D                                                                  61

SEQ ID NO: 15          moltype = AA  length = 30
FEATURE                Location/Qualifiers
source                 1..30
                       mol_type = protein
                       organism = Chlamydia trachomatis
SEQUENCE: 15
SATAIFDTTT LNPTIAGAGD VKTGAEGQLG                                   30

SEQ ID NO: 16          moltype = AA  length = 30
FEATURE                Location/Qualifiers
source                 1..30
                       mol_type = protein
                       organism = Chlamydia trachomatis
SEQUENCE: 16
SATAIFDTTT LNPTIAGAGD VKASAEGQLG                                   30

SEQ ID NO: 17          moltype = AA  length = 31
FEATURE                Location/Qualifiers
source                 1..31
                       mol_type = protein
                       organism = Chlamydia trachomatis
SEQUENCE: 17
LVTPVVDITT LNPTIAGCGS VAGANTEGQI S                                 31

SEQ ID NO: 18          moltype = AA  length = 31
FEATURE                Location/Qualifiers
source                 1..31
                       mol_type = protein
                       organism = Chlamydia trachomatis
SEQUENCE: 18
LAKPVVDITT LNPTIAGCGS VVAANSEGQI S                                 31

SEQ ID NO: 19          moltype = AA  length = 31
FEATURE                Location/Qualifiers
source                 1..31
                       mol_type = protein
                       organism = Chlamydia trachomatis
SEQUENCE: 19
LAEAILDVTT LNPTIAGKGT VVASGSDNDL A                                 31

SEQ ID NO: 20          moltype = AA  length = 31
FEATURE                Location/Qualifiers
source                 1..31
                       mol_type = protein
                       organism = Chlamydia trachomatis
SEQUENCE: 20
LAEAILDVTT LNPTIAGKGT VVASGSENDL A                                 31

SEQ ID NO: 21          moltype = AA  length = 39
FEATURE                Location/Qualifiers
source                 1..39
                       mol_type = protein
                       organism = Chlamydia trachomatis
SEQUENCE: 21
EWQASLALSY RLNMFTPYIG VKWSRASFDA DTIRIAQPK                         39

SEQ ID NO: 22          moltype = AA  length = 30
FEATURE                Location/Qualifiers
source                 1..30
                       mol_type = protein
                       organism = Chlamydia trachomatis
SEQUENCE: 22
DTMQIVSLQL NKMKSRKSCG IAVGTTIVDA                                   30

SEQ ID NO: 23          moltype = AA  length = 68
FEATURE                Location/Qualifiers
source                 1..68
                       mol_type = protein
                       organism = Chlamydia trachomatis
SEQUENCE: 23
NMFTPYIGVK WSRASFDADT IRIAQPKSAT AIFDTTTLNP TIAGAGDVKT GAEGQLGDTM  60
QIVSLQLN                                                           68
```

```
SEQ ID NO: 24            moltype = AA   length = 68
FEATURE                  Location/Qualifiers
source                   1..68
                         mol_type = protein
                         organism = Chlamydia trachomatis
SEQUENCE: 24
NMFTPYIGVK WSRASFDADT IRIAQPKSAT AIFDTTTLNP TIAGAGDVKA SAEGQLGDTM   60
QIVSLQLN                                                            68

SEQ ID NO: 25            moltype = AA   length = 69
FEATURE                  Location/Qualifiers
source                   1..69
                         mol_type = protein
                         organism = Chlamydia trachomatis
SEQUENCE: 25
NMFTPYIGVK WSRASFDSDT IRIAQPRLVT PVVDITTLNP TIAGCGSVAG ANTEGQISDT   60
MQIVSLQLN                                                           69

SEQ ID NO: 26            moltype = AA   length = 69
FEATURE                  Location/Qualifiers
source                   1..69
                         mol_type = protein
                         organism = Chlamydia trachomatis
SEQUENCE: 26
NMFTPYIGVK WSRASFDSNT IRIAQPKLAK PVVDITTLNP TIAGCGSVVA ANSEGQISDT   60
MQIVSLQLN                                                           69

SEQ ID NO: 27            moltype = AA   length = 69
FEATURE                  Location/Qualifiers
source                   1..69
                         mol_type = protein
                         organism = Chlamydia trachomatis
SEQUENCE: 27
NMFTPYIGVK WSRVSFDADT IRIAQPKLAE AILDVTTLNP TIAGKGTVVA SGSDNDLADT   60
MQIVSLQLN                                                           69

SEQ ID NO: 28            moltype = AA   length = 69
FEATURE                  Location/Qualifiers
source                   1..69
                         mol_type = protein
                         organism = Chlamydia trachomatis
SEQUENCE: 28
NMFTPYIGVK WSRVSFDADT IRIAQPKLAE AILDVTTLNP TIAGKGTVVA SGSENDLADT   60
MQIVSLQLN                                                           69

SEQ ID NO: 29            moltype = AA   length = 21
FEATURE                  Location/Qualifiers
source                   1..21
                         mol_type = protein
                         organism = Chlamydia trachomatis
SEQUENCE: 29
DNENQKTVKA ESVPNMSFDQ S                                             21

SEQ ID NO: 30            moltype = AA   length = 21
FEATURE                  Location/Qualifiers
source                   1..21
                         mol_type = protein
                         organism = Chlamydia trachomatis
SEQUENCE: 30
DNENQSTVKT NSVPNMSLDQ S                                             21

SEQ ID NO: 31            moltype = AA   length = 21
FEATURE                  Location/Qualifiers
source                   1..21
                         mol_type = protein
                         organism = Chlamydia trachomatis
SEQUENCE: 31
DGVNATKPAA DSIPNVQLNQ S                                             21

SEQ ID NO: 32            moltype = AA   length = 21
FEATURE                  Location/Qualifiers
source                   1..21
                         mol_type = protein
                         organism = Chlamydia trachomatis
SEQUENCE: 32
DSENATQPAA TSIPNVQLNQ S                                             21

SEQ ID NO: 33            moltype = AA   length = 22
```

-continued

```
FEATURE                  Location/Qualifiers
source                   1..22
                         mol_type = protein
                         organism = Chlamydia trachomatis
SEQUENCE: 33
TKTQSSNFNT AKLIPNAALN QA                                                       22

SEQ ID NO: 34            moltype = AA  length = 22
FEATURE                  Location/Qualifiers
source                   1..22
                         mol_type = protein
                         organism = Chlamydia trachomatis
SEQUENCE: 34
TKTQASSFNT ANLFPNTALN QA                                                       22

SEQ ID NO: 35            moltype = AA  length = 23
FEATURE                  Location/Qualifiers
source                   1..23
                         mol_type = protein
                         organism = Chlamydia trachomatis
SEQUENCE: 35
TLGATSGYLK GNSASFNLVG LFG                                                      23

SEQ ID NO: 36            moltype = AA  length = 22
FEATURE                  Location/Qualifiers
source                   1..22
                         mol_type = protein
                         organism = Chlamydia trachomatis
SEQUENCE: 36
VVELYTDTTF AWSVGARAAL WE                                                       22

SEQ ID NO: 37            moltype = AA  length = 14
FEATURE                  Location/Qualifiers
source                   1..14
                         mol_type = protein
                         organism = Chlamydia trachomatis
SEQUENCE: 37
KEFPLDLTAG TDAA                                                                14

SEQ ID NO: 38            moltype = AA  length = 14
FEATURE                  Location/Qualifiers
source                   1..14
                         mol_type = protein
                         organism = Chlamydia trachomatis
SEQUENCE: 38
QEFPLALIAG TDAA                                                                14

SEQ ID NO: 39            moltype = AA  length = 14
FEATURE                  Location/Qualifiers
source                   1..14
                         mol_type = protein
                         organism = Chlamydia trachomatis
SEQUENCE: 39
KEFPLDLTAG TDAA                                                                14

SEQ ID NO: 40            moltype = AA  length = 14
FEATURE                  Location/Qualifiers
source                   1..14
                         mol_type = protein
                         organism = Chlamydia trachomatis
SEQUENCE: 40
QEFPLALTAG TDAA                                                                14

SEQ ID NO: 41            moltype = AA  length = 14
FEATURE                  Location/Qualifiers
source                   1..14
                         mol_type = protein
                         organism = Chlamydia trachomatis
SEQUENCE: 41
AEFPLDITAG TEAA                                                                14

SEQ ID NO: 42            moltype = AA  length = 14
FEATURE                  Location/Qualifiers
source                   1..14
                         mol_type = protein
                         organism = Chlamydia trachomatis
SEQUENCE: 42
AEFPLDITAG TEAA                                                                14
```

-continued

```
SEQ ID NO: 43            moltype = AA   length = 38
FEATURE                  Location/Qualifiers
source                   1..38
                         mol_type = protein
                         organism = Chlamydia trachomatis
SEQUENCE: 43
ATLGASFQYA QSKPKVEELN VLCNAAEFTI NKPKGYVG                              38

SEQ ID NO: 44            moltype = AA   length = 35
FEATURE                  Location/Qualifiers
source                   1..35
                         mol_type = protein
                         organism = Chlamydia trachomatis
SEQUENCE: 44
TGTKDASIDY HEWQASLALS YRLNMFTPYI GVKWS                                35

SEQ ID NO: 45            moltype = AA   length = 127
FEATURE                  Location/Qualifiers
source                   1..127
                         mol_type = protein
                         organism = Chlamydia trachomatis
SEQUENCE: 45
AISMRVGYYG DFVFDRVLKT DVNKEFQMGA KPTTDTGNSA APSTLTAREN PAYGRHMQDN     60
MFTPYIGVKW SRASFDADTI RIAQPKSATA IFDTTTLNPT IAGAGDVKTG AEGQLGDTMQ    120
IVSLQLN                                                             127

SEQ ID NO: 46            moltype = AA   length = 383
FEATURE                  Location/Qualifiers
source                   1..383
                         mol_type = protein
                         organism = Chlamydia trachomatis
SEQUENCE: 46
AISMRVGYYG DFVFDRVLKT DVNKEFQMGA KPTTDTGNSA APSTLTAREN PAYGRHMQDN     60
MFTPYIGVKW SRASFDADTI RIAQPKSATA IFDTTTLNPT IAGAGDVKTG AEGQLGDTMQ    120
IVSLQLNAIS MRMGYYGDFV FDRVLKTDVN KEFQMGDKPT STTGNATAPT TLTARENPAY    180
GRHMQDNMFT PYIGVKWSRA SFDADTIRIA QPKSATAIFD TTTLNPTIAG AGDVKASAEG    240
QLGDTMQIVS LQLNAISMRM GYYGDFVFDR VLKTDVNKEF EMGEALAGAS GNTTSTLSKL    300
VERTNPAYGK HMQDNMFTPY IGVKWSRASF DSDTIRIAQP RLVTPVVDIT TLNPTIAGSG    360
SVAGANTEGQ ISDTMQIVSL QLN                                           383

SEQ ID NO: 47            moltype = AA   length = 419
FEATURE                  Location/Qualifiers
source                   1..419
                         mol_type = protein
                         organism = Chlamydia trachomatis
SEQUENCE: 47
AISMRVGYYG DFVFDRVLKT DVNKEFQMGA KPTTDTGNSA APSTLTAREN PAYGRHMQDE     60
WQASLALSYR LNMFTPYIGV KWSRASFDAD TIRIAQPKSA TAIFDTTTLN PTIAGAGDVK    120
TGAEGQLGDT MQIVSLQLNA ISMRMGYYGD FVFDRVLKTD VNKEFQMGDK PTSTTGNATA    180
PTTLTARENP AYGRHMQDEW QASLALSYRL NMFTPYIGVK WSRASFDADT IRIAQPKSAT    240
AIFDTTTLNP TIAGAGDVKA SAEGQLGDTM QIVSLQLNAI SMRMGYYGDF VFDRVLKTDV    300
NKEFEMGEAL AGASGNTTST LSKLVERTNP AYGKHMQDEW QASLSLSYRL NMFTPYIGVK    360
WSRASFDSDT IRIAQPRLVT PVVDITTLNP TIAGSGSVAG ANTEGQISDT MQIVSLQLN    419

SEQ ID NO: 48            moltype = AA   length = 844
FEATURE                  Location/Qualifiers
source                   1..844
                         mol_type = protein
                         organism = Chlamydia trachomatis
SEQUENCE: 48
AISMRVGYYG DFVFDRVLKT DVNKEFQMGA KPTTDTGNSA APSTLTAREN PAYGRHMQDE     60
WQASLALSYR LNMFTPYIGV KWSRASFDAD TIRIAQPKSA TAIFDTTTLN PTIAGAGDVK    120
TGAEGQLGDT MQIVSLQLNA ISMRMGYYGD FVFDRVLKTD VNKEFQMGDK PTSTTGNATA    180
PTTLTARENP AYGRHMQDEW QASLALSYRL NMFTPYIGVK WSRASFDADT IRIAQPKSAT    240
AIFDTTTLNP TIAGAGDVKA SAEGQLGDTM QIVSLQLNAI SMRMGYYGDF VFDRVLKTDV    300
NKEFEMGEAL AGASGNTTST LSKLVERTNP AYGKHMQDEW QASLSLSYRL NMFTPYIGVK    360
WSRASFDSDT IRIAQPRLVT PVVDITTLNP TIAGSGSVAG ANTEGQISDT MQIVSLQLNA    420
ISMRMGYYGD FVFDRVLKTD VNKEFEMGEA LAGASGNTTS TLSKLVERTN PAYGKHMQDE    480
WQASLSLSYR LNMFTPYIGV KWSRASFDSN TIRIAQPKLA KPVVDITTLN PTIAGSGSVV    540
AANSEGQISD TMQIVSLQLN AISMRMGYYG DFVFDRVLKT DVNKEFQMGA APTTKDIAGL    600
ENDPTTNVAR PNPAYGKHMQ DEWQASLALS YRLNMFTPYI GVKWSRVSFD ADTIRIAQPK    660
LAEAILDVTT LNPTIAGKGT VVASGSDNDL ADTMQIVSLQ LNAISMRMGY YGDFVFDRVL    720
KTDVNKEFQM GAAPTTSDVA GLQNDPTTNV ARPNPAYGKH MQDEWQASLA LSYRLNMFTP    780
YIGVKWSRVS FDADTIRIAQ PKLAEAILDV TTLNPTIAGK GTVVASGSEN DLADTMQIVS    840
LQLN                                                               844

SEQ ID NO: 49            moltype = AA   length = 205
FEATURE                  Location/Qualifiers
source                   1..205
```

-continued

```
                         mol_type = protein
                         organism = Chlamydia trachomatis
SEQUENCE: 49
NMFTPYIGVK WSRASFDADT IRIAQPKSAT AIFDTTTLNP TIAGAGDVKT GAEGQLGDTM    60
QIVSLQLNNM FTPYIGVKWS RASFDADTIR IAQPKSATAI FDTTTLNPTI AGAGDVKASA   120
EGQLGDTMQI VSLQLNNMFT PYIGVKWSRA SFDSDTIRIA QPRLVTPVVD ITTLNPTIAG   180
SGSVAGANTE GQISDTMQIV SLQLN                                        205

SEQ ID NO: 50           moltype = AA   length = 75
FEATURE                 Location/Qualifiers
source                  1..75
                        mol_type = protein
                        organism = Chlamydia trachomatis
SEQUENCE: 50
MHHHHHHNMF TPYIGVKWSR ASFDADTIRI AQPKSATAIF DTTTLNPTIA GAGDVKASAE    60
GQLGDTMQIV SLQLN                                                    75

SEQ ID NO: 51           moltype = AA   length = 69
FEATURE                 Location/Qualifiers
source                  1..69
                        mol_type = protein
                        organism = Chlamydia trachomatis
SEQUENCE: 51
NMFTPYIGVK WSRASFDSDT IRIAQPRLVT PVVDITTLNP TIAGCGSVAG ANTEGQISDT    60
MQIVSLQLN                                                           69

SEQ ID NO: 52           moltype = AA   length = 76
FEATURE                 Location/Qualifiers
source                  1..76
                        mol_type = protein
                        organism = Chlamydia trachomatis
SEQUENCE: 52
MHHHHHHNMF TPYIGVKWSR ASFDSDTIRI AQPRLVTPVV DITTLNPTIA GCGSVAGANT    60
EGQISDTMQI VSLQLN                                                   76

SEQ ID NO: 53           moltype = AA   length = 274
FEATURE                 Location/Qualifiers
source                  1..274
                        mol_type = protein
                        organism = Chlamydia trachomatis
SEQUENCE: 53
NMFTPYIGVK WSRASFDADT IRIAQPKSAT AIFDTTTLNP TIAGAGDVKT GAEGQLGDTM    60
QIVSLQLNNM FTPYIGVKWS RASFDADTIR IAQPKSATAI FDTTTLNPTI AGAGDVKASA   120
EGQLGDTMQI VSLQLNNMFT PYIGVKWSRA SFDSDTIRIA QPRLVTPVVD ITTLNPTIAG   180
SGSVAGANTE GQISDTMQIV SLQLNNMFTP YIGVKWSRAS FDSNTIRIAQ PKLAKPVVDI   240
TTLNPTIAGS GSVVAANSEG QISDTMQIVS LQLN                              274

SEQ ID NO: 54           moltype = AA   length = 322
FEATURE                 Location/Qualifiers
source                  1..322
                        mol_type = protein
                        organism = Chlamydia trachomatis
SEQUENCE: 54
EWQASLALSY RLNMFTPYIG VKWSRASFDA DTIRIAQPKS ATAIFDTTTL NPTIAGAGDV    60
KTGAEGQLGD TMQIVSLQLN EWQASLALSY RLNMFTPYIG VKWSRASFDA DTIRIAQPKS   120
ATAIFDTTTL NPTIAGAGDV KASAEGQLGD TMQIVSLQLN EWQASLSLSY RLNMFTPYIG   180
VKWSRASFDS DTIRIAQPRL VTPVVDITTL NPTIAGSGSV AGANTEGQIS DTMQIVSLQL   240
NEWQASLSLS YRLNMFTPYI GVKWSRASFD SNTIRIAQPK LAKPVVDITT LNPTIAGSGS   300
VVAANSEGQI SDTMQIVSLQ LN                                           322

SEQ ID NO: 55           moltype = AA   length = 484
FEATURE                 Location/Qualifiers
source                  1..484
                        mol_type = protein
                        organism = Chlamydia trachomatis
SEQUENCE: 55
EWQASLALSY RLNMFTPYIG VKWSRASFDA DTIRIAQPKS ATAIFDTTTL NPTIAGAGDV    60
KTGAEGQLGD TMQIVSLQLN EWQASLALSY RLNMFTPYIG VKWSRASFDA DTIRIAQPKS   120
ATAIFDTTTL NPTIAGAGDV KASAEGQLGD TMQIVSLQLN EWQASLSLSY RLNMFTPYIG   180
VKWSRASFDS DTIRIAQPRL VTPVVDITTL NPTIAGSGSV AGANTEGQIS DTMQIVSLQL   240
NEWQASLSLS YRLNMFTPYI GVKWSRASFD SNTIRIAQPK LAKPVVDITT LNPTIAGSGS   300
VVAANSEGQI SDTMQIVSLQ LNEWQASLAL SYRLNMFTPY IGVKWSRVSF DADTIRIAQP   360
KLAEAILDVT TLNPTIAGKG TVVASGSDND LADTMQIVSL QLNEWQASLA LSYRLNMFTP   420
YIGVKWSRVS FDADTIRIAQ PKLAEAILDV TTLNPTIAGK GTVVASGSEN DLADTMQIVS   480
LQLN                                                              484

SEQ ID NO: 56           moltype = AA   length = 276
FEATURE                 Location/Qualifiers
source                  1..276
```

-continued

```
                         mol_type = protein
                         organism = Chlamydia trachomatis
SEQUENCE: 56
NMFTPYIGVK WSRASFDSDT IRIAQPRLVT PVVDITTLNP TIAGSGSVAG ANTEGQISDT   60
MQIVSLQLNN MFTPYIGVKW SRASFDSDTI RIAQPRLVTP VVDITTLNP IAGSGSVAGA   120
NTEGQISDTM QIVSLQLNNM FTPYIGVKWS RASFDSDTIR IAQPRLVTPV VDITTLNPTI   180
AGSGSVAGAN TEGQISDTMQ IVSLQLNNMF TPYIGVKWSR ASFDSDTIRI AQPRLVTPVV   240
DITTLNPTIA GSGSVAGANT EGQISDTMQI VSLQLN                            276

SEQ ID NO: 57            moltype = AA   length = 544
FEATURE                  Location/Qualifiers
source                   1..544
                         mol_type = protein
                         organism = Chlamydia trachomatis
SEQUENCE: 57
NMFTPYIGVK WSRASFDADT IRIAQPKSAT AIFDTTTLNP TIAGAGDVKA SAEGQLGDTM   60
QIVSLQLNNM FTPYIGVKWS RASFDADTIR IAQPKSATAI FDTTTLNPTI AGAGDVKASA   120
EGQLGDTMQI VSLQLNNMFT PYIGVKWSRA SFDADTIRIA QPKSATAIFD TTTLNPTIAG   180
AGDVKASAEG QLGDTMQIVS LQLNNMFTPY IGVKWSRASF DADTIRIAQP KSATAIFDTT   240
TLNPTIAGAG DVKASAEGQL GDTMQIVSLQ LNNMFTPYIG VKWSRASFDA DTIRIAQPKS   300
ATAIFDTTTL NPTIAGAGDV KASAEGQLGD TMQIVSLQLN NMFTPYIGVK WSRASFDADT   360
IRIAQPKSAT AIFDTTTLNP TIAGAGDVKA SAEGQLGDTM QIVSLQLNNM FTPYIGVKWS   420
RASFDADTIR IAQPKSATAI FDTTTLNPTI AGAGDVKASA EGQLGDTMQI VSLQLNNMFT   480
PYIGVKWSRA SFDADTIRIA QPKSATAIFD TTTLNPTIAG AGDVKASAEG QLGDTMQIVS   540
LQLN                                                              544

SEQ ID NO: 58            moltype = AA   length = 272
FEATURE                  Location/Qualifiers
source                   1..272
                         mol_type = protein
                         organism = Chlamydia trachomatis
SEQUENCE: 58
NMFTPYIGVK WSRASFDADT IRIAQPKSAT AIFDTTTLNP TIAGAGDVKA SAEGQLGDTM   60
QIVSLQLNNM FTPYIGVKWS RASFDADTIR IAQPKSATAI FDTTTLNPTI AGAGDVKASA   120
EGQLGDTMQI VSLQLNNMFT PYIGVKWSRA SFDADTIRIA QPKSATAIFD TTTLNPTIAG   180
AGDVKASAEG QLGDTMQIVS LQLNNMFTPY IGVKWSRASF DADTIRIAQP KSATAIFDTT   240
TLNPTIAGAG DVKASAEGQL GDTMQIVSLQ LN                                272

SEQ ID NO: 59            moltype = AA   length = 276
FEATURE                  Location/Qualifiers
source                   1..276
                         mol_type = protein
                         organism = Chlamydia trachomatis
SEQUENCE: 59
NMFTPYIGVK WSRASFDSDT IRIAQPRLVT PVVDITTLNP TIAGCGSVAG ANTEGQISDT   60
MQIVSLQLNN MFTPYIGVKW SRASFDSDTI RIAQPRLVTP VVDITTLNPT IAGCGSVAGA   120
NTEGQISDTM QIVSLQLNNM FTPYIGVKWS RASFDSDTIR IAQPRLVTPV VDITTLNPTI   180
AGCGSVAGAN TEGQISDTMQ IVSLQLNNMF TPYIGVKWSR ASFDSDTIRI AQPRLVTPVV   240
DITTLNPTIA GCGSVAGANT EGQISDTMQI VSLQLN                            276

SEQ ID NO: 60            moltype = AA   length = 785
FEATURE                  Location/Qualifiers
source                   1..785
                         mol_type = protein
                         organism = Chlamydia trachomatis
SEQUENCE: 60
SRQNAEENLK NFAKELKLPD VAFDQNNTCI LFVDGEFSLH LTYEEHSDRL YVYAPLLDGL   60
PDNPQRRLAL YEKLLEGSML GGQMAGGGVG VATKEQLILM HCVLDMKYAE TNLLKAFAQL   120
FIETVVKWRT VCSDISAGRE PTVDTMPQMP QGGGGGIQPP PAGIRATVKA IVESTPEAPE   180
EIPPVEGEES TATEDPNSNT EGSSANTNLE GSQGDTADTG TGDVNNESQD TSDTGNAESE   240
EQLQDSTQSN EENTLPNSNI DQSNENTDES SDSHTEEITD ESVSSSSESG SSTPQDGGAA   300
SSGAPSGDQS ISANACLAKS YAASTDSSPV SNSSGSEEPV TSSSDSDVTA SSDNPDSSSS   360
GDSAGDSEEP TEPEAGSTTE TLTLIGGGAI YGETVKIENF SGAISMRVGY YGDFVFDRVL   420
KTDVNKEFQM GAKPTTDTGN SAAPSTLTAR ENPAYGRHMQ DNMFTPYIGV KWSRASFDAD   480
TIRIAQPKSA TAIFDTTTLN PTIAGAGDVK TGAEGQLGDT MQIVSLQLNA ISMRMGYYGD   540
FVFDRVLKTD VNKEFQMGDK PTSTTGNATA PTTLTARENP AYGRHMQDNM FTPYIGVKWS   600
RASFDADTIR IAQPKSATAI FDTTTLNPTI AGAGDVKASA EGQLGDTMQI VSLQLNAISM   660
RMGYYGDFVF DRVLKTDVNK EFEMGEALAG ASGNTTSTLS KLVERTNPAY GKHMQDNMFT   720
PYIGVKWSRA SFDSDTIRIA QPRLVTPVVD ITTLNPTIAG SGSVAGANTE GQISDTMQIV   780
SLQLN                                                             785

SEQ ID NO: 61            moltype = AA   length = 740
FEATURE                  Location/Qualifiers
source                   1..740
                         mol_type = protein
                         organism = Chlamydia trachomatis
SEQUENCE: 61
SRQNAEENLK NFAKELKLPD VAFDQNNTCI LFVDGEFSLH LTYEEHSDRL YVYAPLLDGL   60
PDNPQRRLAL YEKLLEGSML GGQMAGGGVG VATKEQLILM HCVLDMKYAE TNLLKAFAQL   120
```

```
FIETVVKWRT VCSDISAGRE PTVDTMPQMP QGGGGGIQPP PAGIRATVKA IVESTPEAPE  180
EIPPVEGEES TATEDPNSNT EGSSANTNLE GSQGDTADTG TGDVNNESQD TSDTGNAESE  240
EQLQDSTQSN EENTLPNSNI DQSNENTDES SDSHTEEITD ESVSSSSESG SSTPQDGGAA  300
SSGAPSGDQS ISANACLAKS YAASTDSSPV SNSSGSEEPV TSSSDSDVTA SSDNPDSSSS  360
GDSAGDSEEP TEPEAGSTTE TLTLIGGGAI YGETVKIENF SGDAISMRVG YYGDFVFDRV  420
LKTDVNKEFQ MGAKPTTDTG NSAAPSTLTA RENPAYGRHM QDAEMFTNAA SMALNIWDRF  480
DVFSTLGATS GYLKGNSASF NLVGLFGDNE NQKTVKAESV PNMSFDQSVV ELYTDTTFAW  540
SVGARAALWE SGSATLGASF QYAQSKPKVE ELNVLSNAAE FTINKPKGYV GKEFPLDLTA  600
GTDAATGTKD ASIDYHEWQA SLALSYRLNM FTPYIGVKWS RASFDADTIR IAQPKSATAI  660
FDTTTLNPTI AGAGDVKTGA EGQLGDTMQI VSLQLNKMKS RKSSGIAVGT TIVDADKYAV  720
TVETRLIDER AAHVNAQFRF                                              740

SEQ ID NO: 62           moltype = AA  length = 294
FEATURE                 Location/Qualifiers
source                  1..294
                        mol_type = protein
                        organism = Chlamydia trachomatis
SEQUENCE: 62
DAISMRVGYY GDFVFDRVLK TDVNKEFQMG AKPTTDTGNS AAPSTLTARE NPAYGRHMQD  60
AEMFTNAACM ALNIWDRFDV FCTLGATSGY LKGNSASFNL VGLFGDNENQ KTVKAESVPN  120
MSFDQSVVEL YTDTTFAWSV GARAALWECG CATLGASFQY AQSKPKVEEL NVLCNAAEFT  180
INKPKGYVGK EFPLDLTAGT DAATGTKDAS IDYHEWQASL ALSYRLNMFT PYIGVKWSRA  240
SFDADTIRIA QPKSATAIFD TTTLNPTIAG AGDVKTGAEG QLGDTMQIVS LQLN         294

SEQ ID NO: 63           moltype = AA  length = 294
FEATURE                 Location/Qualifiers
source                  1..294
                        mol_type = protein
                        organism = Chlamydia trachomatis
SEQUENCE: 63
DAISMRVGYY GDFVFDRVLK TDVNKEFQMG AKPTTDTGNS AAPSTLTARE NPAYGRHMQD  60
AEMFTNAASM ALNIWDRFDV FSTLGATSGY LKGNSASFNL VGLFGDNENQ KTVKAESVPN  120
MSFDQSVVEL YTDTTFAWSV GARAALWESG SATLGASFQY AQSKPKVEEL NVLSNAAEFT  180
INKPKGYVGK EFPLDLTAGT DAATGTKDAS IDYHEWQASL ALSYRLNMFT PYIGVKWSRA  240
SFDADTIRIA QPKSATAIFD TTTLNPTIAG AGDVKTGAEG QLGDTMQIVS LQLN         294

SEQ ID NO: 64           moltype = AA  length = 500
FEATURE                 Location/Qualifiers
source                  1..500
                        mol_type = protein
                        organism = Chlamydia trachomatis
SEQUENCE: 64
DAISMRVGYY GDFVFDRVLK TDVNKEFQMG AKPTTDTGNS AAPSTLTARE NPAYGRHMQD  60
AEMFTNAASM ALNIWDRFDV FSTLGATSGY LKGNSASFNL VGLFGDNENQ KTVKAESVPN  120
MSFDQSVVEL YTDTTFAWSV GARAALWESG SATLGASFQY AQSKPKVEEL NVLSNAAEFT  180
INKPKGYVGK EFPLDLTAGT DAATGTKDAS IDYHEWQASL ALSYRLNMFT PYIGVKWSRA  240
SFDADTIRIA QPKSATAIFD TTTLNPTIAG AGDVKTGAEG QLGDTMQIVS LQLNNMFTPY  300
IGVKWSRASF DADTIRIAQP KSATAIFDTT TLNPTIAGAG DVKASAEGQL GDTMQIVSLQ  360
LNNMFTPYIG VKWSRASFDS DTIRIAQPRL VTPVVDITTL NPTIAGSGSV AGANTEGQIS  420
DTMQIVSLQL NNMFTPYIGV KWSRASFDSN TIRIAQPKLA KPVVDITTLN PTIAGSGSVV  480
AANSEGQISD TMQIVSLQLN                                              500

SEQ ID NO: 65           moltype = AA  length = 1068
FEATURE                 Location/Qualifiers
source                  1..1068
                        mol_type = protein
                        organism = Chlamydia trachomatis
SEQUENCE: 65
TVKAIVESTP EAPEEIPPVE GEESTATEDP NSNTEGSSAN TNLEGSQGDT ADTGTGDVNN  60
ESQDTSDTGN AESEEQLQDS TQSNEENTLP NSNIDQSNEN TDESSDSHTE EITDESVSSS  120
SESGSSTPQD GGAASSGAPS GDQSISANAC LAKSYAASTD SSPVSNSSGS EEPVTSSSDS  180
DVTASSDNPD SSSSGDSAGD SEEPTEPEAG STTETLTLIG GGAIYGETVK IENFSGSRQN  240
AEENLKNFAK ELKLPDVAFD QNNTCILFVD GEFSLHLTYE EHSDRLYVYA PLLDGLPDNP  300
QRRLALYEKL LEGSMLGGQM AGGGVGVATK EQLILMHCVL DMKYAETNLL KAFAQLFIET  360
VVKWRTVCSD ISAGREPTVD TMPQMPQGGG GIQPPPAGI RASRQNAEEN LKNFAKELKL  420
PDVAFDQNNT CILFVDGEFS LHLTYEEHSD RLYVYAPLLD GLPDNPQRRL ALYEKLLEGS  480
MLGGQMAGGG VGVATKEQLI LMHCVLDMKY AETNLLKAFA QLFIETVVKW RTVCSDISAG  540
REPTVDTMPQ MPQGGGGGIQ PPPAGIRADA ISMRVGYYY FVFDRVLKTD VNKEFQMGAK  600
PTTDTGNSAA PSTLTARENP AYGRHMQDAE MFTNAASMAL NIWDRFDVFS TLGATSGYLK  660
GNSASFNLVG LFGDNENQKT VKAESVPNMS FDQSVVELYT DTTFAWSVGA RAALWESGSA  720
TLGASFQYAQ SKPKVEELNV LSNAAEFTIN KPKGYVGKEF PLDLTAGTDA ATGTKDASID  780
YHEWQASLAL SYRLNMFTPY IGVKWSRASF DADTIRIAQP KSATAIFDTT TLNPTIAGAG  840
DVKTGAEGQL GDTMQIVSLQ LNNMFTPYIG VKWSRASFDA DTIRIAQPKS ATAIFDTTTL  900
NPTIAGAGDV KASAEGQLGD TMQIVSLQLN NMFTPYIGVK WSRASFDSNTI IRIAQPRLVT  960
PVVDITTLNP TIAGSGSVAG ANTEGQISDT MQIVSLQLNN MFTPYIGVKW SRASFDSNTI  1020
RIAQPKLAKP VVDITTLNPT IAGSGSVVAA NSEGQISDTM QIVSLQLN              1068

SEQ ID NO: 66           moltype = AA  length = 606
FEATURE                 Location/Qualifiers
```

```
source                        1..606
                              mol_type = protein
                              organism = Chlamydia trachomatis
SEQUENCE: 66
SRQNAEENLK NFAKELKLPD VAFDQNNTCI LFVDGEFSLH LTYEEHSDRL YVYAPLLDGL    60
PDNPQRRLAL YEKLLEGSML GGQMAGGGVG VATKEQLILM HCVLDMKYAE TNLLKAFAQL   120
FIETVVKWRT VCSDISAGRE PTVDTMPQMP QGGGGGIQPP PAGIRASRQN AEENLKNFAK   180
ELKLPDVAFD QNNTCILFVD GEFSLHLTYE EHSDRLYVYA PLLDGLPDNP QRRLALYEKL   240
LEGSMLGGQM AGGGVGVATK EQLILMHCVL DMKYAETNLL KAFAQLFIET VVKWRTVCSD   300
ISAGREPTVD TMPQMPQGGG GGIQPPPAGI RANMFTPYIG VKWSRASFDA DTIRIAQPKS   360
ATAIFDTTTL NPTIAGAGDV KTGAEGQLGD TMQIVSLQLN NMFTPYIGVK WSRASFDADT   420
IRIAQPKSAT AIFDTTTLNP TIAGAGDVKA SAEGQLGDTM QIVSLQLNNM FTPYIGVKWS   480
RASFDSDTIR IAQPRLVTPV VDITTLNPTI AGSGSVAGAN TEGQISDTMQ IVSLQLNNMF   540
TPYIGVKWSR ASFDSNTIRI AQPKLAKPVV DITTLNPTIA GSGSVVAANS EGQISDTMQI   600
VSLQLN                                                             606

SEQ ID NO: 67               moltype = AA  length = 1093
FEATURE                     Location/Qualifiers
source                      1..1093
                            mol_type = protein
                            organism = Chlamydia trachomatis
SEQUENCE: 67
SRQNAEENLK NFAKELKLPD VAFDQNNTCI LFVDGEFSLH LTYEEHSDRL YVYAPLLDGL    60
PDNPQRRLAL YEKLLEGSML GGQMAGGGVG VATKEQLILM HCVLDMKYAE TNLLKAFAQL   120
FIETVVKWRT VCSDISAGRE PTVDTMPQMP QGGGGGIQPP PAGIRASRQN AEENLKNFAK   180
ELKLPDVAFD QNNTCILFVD GEFSLHLTYE EHSDRLYVYA PLLDGLPDNP QRRLALYEKL   240
LEGSMLGGQM AGGGVGVATK EQLILMHCVL DMKYAETNLL KAFAQLFIET VVKWRTVCSD   300
ISAGREPTVD TMPQMPQGGG GGIQPPPAGI RAGIAHTEWE SVIGLEVHVE LNTESKLFSP   360
ARNHFGDEPN TNISPVCTGM PGSLPVLNKD AVRKAVLFGC AVEGDVALFS RFDRKSYFYP   420
DSPRNFQITQ YEHPIVRGGC IRAVVEGEEK TFELAQTHLG DDAGMLKHFG DFAGVDYNRA   480
GVPLIEIVSK PCMFSAEDAV AYANALVSIL GYIGISDCNM EEGSIRFDVN ISVRPRGSRE   540
LRNKVEIKNM NSFTFMAQAL EAEKRRQIEE YLSYPNEDPK KVVPAATYRW DPEKKKTVLM   600
RLKERAEDYM YFVEPDLPVL QITETYIDEV RQTLPELPHS KYMRYITDFD IAEDLAMILV   660
GDRHTAHFFE TATMSCKNYR ALSNWITVEF AGRCKARGKT LPPTGILPEW VAQLVNFIDR   720
GVITGKIAKE IADRMVSSFG ESPEDILRRH PSLLPMTDDH ALRAIVKEVV AQNTASVADY   780
KNGKAKALGF LVGQIMKRTE GKAPPKRVNE LLLAAMRDMN MFTPYIGVKW SRASFDADTI   840
RIAQPKSATA IFDTTTLNPT IAGAGDVKTG AEGQLGDTMQ IVSLQLNNMF TPYIGVKWSR   900
ASFDADTIRI AQPKSATAIF DTTTLNPTIA GAGDVKASAE GQLGDTMQIV SLQLNNMFTP   960
YIGVKWSRAS FDSDTIRIAQ PRLVTPVVDI TTLNPTIAGS GSVAGANTEG QISDTMQIVS  1020
LQLNNMFTPY IGVKWSRASF DSNTIRIAQP KLAKPVVDIT TLNPTIAGSG SVVAANSEGQ  1080
ISDTMQIVSL QLN                                                    1093

SEQ ID NO: 68               moltype = AA  length = 393
FEATURE                     Location/Qualifiers
source                      1..393
                            mol_type = protein
                            organism = Chlamydia trachomatis
SEQUENCE: 68
MKKLLKSVLV FAALSSASSL QALPVGNPAE PSLMIDGILW EGFGGDPCDP CATWCDAISM    60
RVGYYGDFVF DRVLKTDVNK EFQMGAKPTT DTGNSAAPST LTARENPAYG RHMQDAEMFT   120
NAACMALNIW DRFDVFCTLG ATSGYLKGNS ASFNLVGLFG DNENQKTVKA ESVPNMSFDQ   180
SVVELYTDTT FAWSVGARAA LWECGCATLG ASFQYAQSKP KVEELNVLCN AAEFTINKPK   240
GYVGKEFPLD LTAGTDAATG TKDASIDYHE WQASLALSYR LNMFTPYIGV KWSRASFDAD   300
TIRIAQPKSA TAIFDTTTLN PTIAGAGDVK TGAEGQLGDT MQIVSLQLNK MKSRKSCGIA   360
VGTTIVDADK YAVTVETRLI DERAAHVNAQ FRF                                393

SEQ ID NO: 69               moltype = AA  length = 122
FEATURE                     Location/Qualifiers
source                      1..122
                            mol_type = protein
                            organism = Chlamydia trachomatis
SEQUENCE: 69
SATAIFDTTT LNPTIAGAGD VKTGAEGQLG SATAIFDTTT LNPTIAGAGD VKASAEGQLG    60
LVTPVVDITT LNPTIAGSGS VAGANTEGQI SLAKPVVDIT TLNPTIAGSG SVVAANSEGQ   120
IS                                                                 122

SEQ ID NO: 70               moltype = AA  length = 178
FEATURE                     Location/Qualifiers
source                      1..178
                            mol_type = protein
                            organism = Chlamydia trachomatis
SEQUENCE: 70
IRIAQPKSAT AIFDTTTLNP TIAGAGDVKT GAEGQLGDTM QIVSIRIAQP KSATAIFDTT    60
TLNPTIAGAG DVKASAEGQL GDTMQIVSIR IAQPRLVTPV VDITTLNPTI AGSGSVAGAN   120
TEGQISDTMQ IVSIRIAQPK LAKPVVDITT LNPTIAGSGS VVAANSEGQI SDTMQIVS     178

SEQ ID NO: 71               moltype = AA  length = 393
FEATURE                     Location/Qualifiers
source                      1..393
```

-continued

```
                        mol_type = protein
                        organism = Chlamydia trachomatis
SEQUENCE: 71
MKKLLKSVLV FAALSSASSL QALPVGNPAE PSLMIDGILW EGFGGDPCDP CTTWCDAISM   60
RMGYYGDFVF DRVLKTDVNK EFQMGDKPTS TTGNATAPTT LTARENPAYG RHMQDAEMFT  120
NAACMALNIW DRFDVFCTLG ASSGYLKGNS ASFNLVGLFG DNENQSTVKT NSVPNMSLDQ  180
SVVELYTDTA FSWSVGARAA LWECGCATLG ASFQYAQSKP KVEELNVLCN AAEFTINKPK  240
GYVGQEFPLA LIAGTDAATG TKDASIDYHE WQASLALSYR LNMFTPYIGV KWSRASFDAD  300
TIRIAQPKSA TAIFDTTTLN PTIAGAGDVK ASAEGQLGDT MQIVSLQLNK MKSRKSCGIA  360
VGTTIVDADK YAVTVETRLI DERAAHVNAQ FRF                               393

SEQ ID NO: 72            moltype = AA  length = 395
FEATURE                  Location/Qualifiers
source                   1..395
                         mol_type = protein
                         organism = Chlamydia trachomatis
SEQUENCE: 72
MKKLLKSVLV FAALSSASSL QALPVGNPAE PSLMIDGILW EGFGGDPCDP CTTWCDAISM   60
RMGYYGDFVF DRVLKTDVNK EFEMGEALAG ASGNTTSTLS KLVERTNPAY GKHMQDAEMF  120
TNAACMTLNI WDRFDVFCTL GATSGYLKGN SASFNLVGLF GDGVNATKPA ADSIPNVQLN  180
QSVVELYTDT TFAWSVGARA ALWECGCATL GASFQYAQSK PKIEELNVLC NAAEFTINKP  240
KGYVGKEFPL DLTAGTDAAT GTKDASIDYH EWQASLSLSY RLNMFTPYIG VKWSRASFDS  300
DTIRIAQPRL VTPVVDITTL NPTIAGCGSV AGANTEGQIS DTMQIVSLQL NKMKSRKSCG  360
IAVGTTIVDA DKYAVTVETR LIDERAAHVN AQFRF                             395

SEQ ID NO: 73            moltype = AA  length = 393
FEATURE                  Location/Qualifiers
source                   1..393
                         mol_type = protein
                         organism = Chlamydia trachomatis
SEQUENCE: 73
MKKLLKSVLV FAALSSASSL QALPVGNPAE PSLMIDGILW EGFGGDPCDP CTTWCDAISM   60
RMGYYGDFVF DRVLKTDVNK EFEMGEALAG ASGNTTSTLS KLVERTNPAY GKHMQDAEMF  120
TNAACMALNI WDRFDVFCTL GATSGYLRGN SASFNLVGLF GDSENATQPA ATSIPNVQLN  180
QSVVELYTDT AFAWSVGARA ALWECGCATL GASFQYAQSK PKVEELNVLC NAAEFTINKP  240
KGYVGQEFPL ALTAGTDAAT GTKDASIDYH EWQASLSLSY RLNMFTPYIG VKWSRASFDS  300
NTIRIAQPKL AKPVVDITTL NPTIAGCGSV VAANSEGQIS DTMQIVSLQL NKMKSRKSCG  360
IAVGTTIVDA DKYAVTVETR LIDERAAHVN AQF                               393

SEQ ID NO: 74            moltype = AA  length = 389
FEATURE                  Location/Qualifiers
source                   1..389
                         mol_type = protein
                         organism = Chlamydia trachomatis
SEQUENCE: 74
MKKLLKSVLV FAALSSASSL QALPVGNPAE PSLMIDGILW EGFGGDPCDP CTTWCDAISM   60
RMGYYGDFVF DRVLKTDVNK EFQMGAAPTT KDIAGLENDP TTNVARPNPA YGKHMQDAEM  120
FTNAAYMALN IWDRFDVFCT LGATTGYLKG NSASFNLVGL FGTKTQSSNF NTAKLIPNAA  180
LNQAVVELYT DTTFAWSVGA RAALWECGCA TLGASFQYAQ SKPKVEELNV LCNASEFTIN  240
KPKGYVGAEF PLDITAGTEA ATGTKDASID YHEWQASLAL SYRLNMFTPY IGVKWSRVSF  300
DADTIRIAQP KLAEAILDVT TLNPTIAGKG TVVASGSDND LADTMQIVSL QLNKMKSRKS  360
CGIAVGTTIV DADKYAVTVE TRLIDERAA                                    389

SEQ ID NO: 75            moltype = AA  length = 397
FEATURE                  Location/Qualifiers
source                   1..397
                         mol_type = protein
                         organism = Chlamydia trachomatis
SEQUENCE: 75
MKKLLKSVLV FAALSSASSL QALPVGNPAE PSLMIDGILW EGFGGDPCDP CTTWCDAISM   60
RMGYYGDFVF DRVLKTDVNK EFQMGAAPTT SDVAGLQNDP TTNVARPNPA YGKHMQDAEM  120
FTNAAYMALN IWDRFDVFCT LGATTGYLKG NSASFNLVGL FGTKTQASSF NTANLFPNTA  180
LNQAVVELYT DTTFAWSVGA RAALWECGCA TLGASFQYAQ SKPKVEELNV LCNASEFTIN  240
KPKGYVGAEF PLDITAGTEA ATGTKDASID YHEWQASLAL SYRLNMFTPY IGVKWSRVSF  300
DADTIRIAQP KLAEAILDVT TLNPTIAGKG TVVASGSEND LADTMQIVSL QLNKMKSRKS  360
CGIAVGTTIV DADKYAVTVE TRLIDERAAH VNAQFRF                           397

SEQ ID NO: 76            moltype = AA  length = 9
FEATURE                  Location/Qualifiers
source                   1..9
                         mol_type = protein
                         organism = Chlamydia trachomatis
SEQUENCE: 76
TTLNPTIAG                                                            9

SEQ ID NO: 77            moltype = AA  length = 27
FEATURE                  Location/Qualifiers
source                   1..27
                         mol_type = protein
```

-continued

```
                          organism = Chlamydia trachomatis
SEQUENCE: 77
SMRVGYYGDF VFDRVLKTDV NKEFQMG                                                27

SEQ ID NO: 78            moltype = AA   length = 26
FEATURE                  Location/Qualifiers
source                   1..26
                         mol_type = protein
                         organism = Chlamydia trachomatis
SEQUENCE: 78
NPAYGRHMQD AEMFTNAACM ALNIWD                                                 26

SEQ ID NO: 79            moltype = AA   length = 8
FEATURE                  Location/Qualifiers
source                   1..8
                         mol_type = protein
                         organism = Chlamydia trachomatis
SEQUENCE: 79
SATAIFDT                                                                     8

SEQ ID NO: 80            moltype = AA   length = 8
FEATURE                  Location/Qualifiers
source                   1..8
                         mol_type = protein
                         organism = Chlamydia trachomatis
SEQUENCE: 80
LVTPVVDI                                                                     8

SEQ ID NO: 81            moltype = AA   length = 8
FEATURE                  Location/Qualifiers
source                   1..8
                         mol_type = protein
                         organism = Chlamydia trachomatis
SEQUENCE: 81
LAKPVVDI                                                                     8

SEQ ID NO: 82            moltype = AA   length = 8
FEATURE                  Location/Qualifiers
source                   1..8
                         mol_type = protein
                         organism = Chlamydia trachomatis
SEQUENCE: 82
LAEAILDV                                                                     8

SEQ ID NO: 83            moltype = AA   length = 13
FEATURE                  Location/Qualifiers
source                   1..13
                         mol_type = protein
                         organism = Chlamydia trachomatis
SEQUENCE: 83
AGDVKTGAEG QLG                                                               13

SEQ ID NO: 84            moltype = AA   length = 13
FEATURE                  Location/Qualifiers
source                   1..13
                         mol_type = protein
                         organism = Chlamydia trachomatis
SEQUENCE: 84
AGDVKASAEG QLG                                                               13

SEQ ID NO: 85            moltype = AA   length = 14
FEATURE                  Location/Qualifiers
source                   1..14
                         mol_type = protein
                         organism = Chlamydia trachomatis
SEQUENCE: 85
CGSVAGANTE GQIS                                                              14

SEQ ID NO: 86            moltype = AA   length = 14
FEATURE                  Location/Qualifiers
source                   1..14
                         mol_type = protein
                         organism = Chlamydia trachomatis
SEQUENCE: 86
CGSVVAANSE GQIS                                                              14

SEQ ID NO: 87            moltype = AA   length = 13
FEATURE                  Location/Qualifiers
source                   1..13
```

```
                              mol_type = protein
                              organism = Chlamydia trachomatis
SEQUENCE: 87
KGTVVSSAEN ELA                                                    13

SEQ ID NO: 88                 moltype = AA  length = 14
FEATURE                       Location/Qualifiers
source                        1..14
                              mol_type = protein
                              organism = Chlamydia trachomatis
SEQUENCE: 88
KGTVVASGSE NDLA                                                   14

SEQ ID NO: 89                 moltype = AA  length = 20
FEATURE                       Location/Qualifiers
source                        1..20
                              mol_type = protein
                              organism = Chlamydia trachomatis
SEQUENCE: 89
DASIDYHEWQ ASLALSYRLN                                             20

SEQ ID NO: 90                 moltype = AA  length = 20
FEATURE                       Location/Qualifiers
source                        1..20
                              mol_type = protein
                              organism = Chlamydia trachomatis
SEQUENCE: 90
ASLALSYRLN MFTPYIGVKW                                             20

SEQ ID NO: 91                 moltype = AA  length = 20
FEATURE                       Location/Qualifiers
source                        1..20
                              mol_type = protein
                              organism = Chlamydia trachomatis
SEQUENCE: 91
MFTPYIGVKW SRASFDADTI                                             20

SEQ ID NO: 92                 moltype = AA  length = 20
FEATURE                       Location/Qualifiers
source                        1..20
                              mol_type = protein
                              organism = Chlamydia trachomatis
SEQUENCE: 92
SRASFDADTI RIAQPKSATA                                             20

SEQ ID NO: 93                 moltype = AA  length = 20
FEATURE                       Location/Qualifiers
source                        1..20
                              mol_type = protein
                              organism = Chlamydia trachomatis
SEQUENCE: 93
RIAQPKSATA IFDTTTLNPT                                             20

SEQ ID NO: 94                 moltype = AA  length = 20
FEATURE                       Location/Qualifiers
source                        1..20
                              mol_type = protein
                              organism = Chlamydia trachomatis
SEQUENCE: 94
IFDTTTLNPT IAGAGDVKAS                                             20

SEQ ID NO: 95                 moltype = AA  length = 20
FEATURE                       Location/Qualifiers
source                        1..20
                              mol_type = protein
                              organism = Chlamydia trachomatis
SEQUENCE: 95
IAGAGDVKAS AEGQLGDTMQ                                             20

SEQ ID NO: 96                 moltype = AA  length = 20
FEATURE                       Location/Qualifiers
source                        1..20
                              mol_type = protein
                              organism = Chlamydia trachomatis
SEQUENCE: 96
AEGQLGDTMQ IVSLQLNKMK                                             20

SEQ ID NO: 97                 moltype = AA  length = 20
FEATURE                       Location/Qualifiers
```

-continued

```
source                   1..20
                         mol_type = protein
                         organism = Chlamydia trachomatis
SEQUENCE: 97
DASIDYHEWQ ASLSLSYRLN                                                            20

SEQ ID NO: 98            moltype = AA  length = 20
FEATURE                  Location/Qualifiers
source                   1..20
                         mol_type = protein
                         organism = Chlamydia trachomatis
SEQUENCE: 98
ASLSLSYRLN MFTPYIGVKW                                                            20

SEQ ID NO: 99            moltype = AA  length = 20
FEATURE                  Location/Qualifiers
source                   1..20
                         mol_type = protein
                         organism = Chlamydia trachomatis
SEQUENCE: 99
MFTPYIGVKW SRASFDSDTI                                                            20

SEQ ID NO: 100           moltype = AA  length = 20
FEATURE                  Location/Qualifiers
source                   1..20
                         mol_type = protein
                         organism = Chlamydia trachomatis
SEQUENCE: 100
SRASFDSDTI RIAQPRLVTP                                                            20

SEQ ID NO: 101           moltype = AA  length = 20
FEATURE                  Location/Qualifiers
source                   1..20
                         mol_type = protein
                         organism = Chlamydia trachomatis
SEQUENCE: 101
RIAQPRLVTP VVDITTLNPT                                                            20

SEQ ID NO: 102           moltype = AA  length = 20
FEATURE                  Location/Qualifiers
source                   1..20
                         mol_type = protein
                         organism = Chlamydia trachomatis
SEQUENCE: 102
VVDITTLNPT IAGCGSVAGA                                                            20

SEQ ID NO: 103           moltype = AA  length = 21
FEATURE                  Location/Qualifiers
source                   1..21
                         mol_type = protein
                         organism = Chlamydia trachomatis
SEQUENCE: 103
IAGCGSVAGA NTEGQISDTM Q                                                          21

SEQ ID NO: 104           moltype = AA  length = 20
FEATURE                  Location/Qualifiers
source                   1..20
                         mol_type = protein
                         organism = Chlamydia trachomatis
SEQUENCE: 104
TEGQISDTMQ IVSLQLNKMK                                                            20

SEQ ID NO: 105           moltype = AA  length = 9
FEATURE                  Location/Qualifiers
source                   1..9
                         mol_type = protein
                         organism = Chlamydia trachomatis
SEQUENCE: 105
SRASFDADT                                                                        9

SEQ ID NO: 106           moltype = AA  length = 9
FEATURE                  Location/Qualifiers
source                   1..9
                         mol_type = protein
                         organism = Chlamydia trachomatis
SEQUENCE: 106
RASFDADTI                                                                        9

SEQ ID NO: 107           moltype = AA  length = 9
```

```
FEATURE                 Location/Qualifiers
source                  1..9
                        mol_type = protein
                        organism = Chlamydia trachomatis
SEQUENCE: 107
ASFDADTIR                                                                    9

SEQ ID NO: 108          moltype = AA   length = 9
FEATURE                 Location/Qualifiers
source                  1..9
                        mol_type = protein
                        organism = Chlamydia trachomatis
SEQUENCE: 108
SFDADTIRI                                                                    9

SEQ ID NO: 109          moltype = AA   length = 9
FEATURE                 Location/Qualifiers
source                  1..9
                        mol_type = protein
                        organism = Chlamydia trachomatis
SEQUENCE: 109
FDADTIRIA                                                                    9

SEQ ID NO: 110          moltype = AA   length = 9
FEATURE                 Location/Qualifiers
source                  1..9
                        mol_type = protein
                        organism = Chlamydia trachomatis
SEQUENCE: 110
DADTIRIAQ                                                                    9

SEQ ID NO: 111          moltype = AA   length = 9
FEATURE                 Location/Qualifiers
source                  1..9
                        mol_type = protein
                        organism = Chlamydia trachomatis
SEQUENCE: 111
ADTIRIAQP                                                                    9

SEQ ID NO: 112          moltype = AA   length = 9
FEATURE                 Location/Qualifiers
source                  1..9
                        mol_type = protein
                        organism = Chlamydia trachomatis
SEQUENCE: 112
DTIRIAQPK                                                                    9

SEQ ID NO: 113          moltype = AA   length = 9
FEATURE                 Location/Qualifiers
source                  1..9
                        mol_type = protein
                        organism = Chlamydia trachomatis
SEQUENCE: 113
TIRIAQPKS                                                                    9

SEQ ID NO: 114          moltype = AA   length = 9
FEATURE                 Location/Qualifiers
source                  1..9
                        mol_type = protein
                        organism = Chlamydia trachomatis
SEQUENCE: 114
IRIAQPKSA                                                                    9

SEQ ID NO: 115          moltype = AA   length = 9
FEATURE                 Location/Qualifiers
source                  1..9
                        mol_type = protein
                        organism = Chlamydia trachomatis
SEQUENCE: 115
RIAQPKSAT                                                                    9

SEQ ID NO: 116          moltype = AA   length = 9
FEATURE                 Location/Qualifiers
source                  1..9
                        mol_type = protein
                        organism = Chlamydia trachomatis
SEQUENCE: 116
IAQPKSATA                                                                    9
```

-continued

```
SEQ ID NO: 117          moltype = AA   length = 9
FEATURE                 Location/Qualifiers
source                  1..9
                        mol_type = protein
                        organism = Chlamydia trachomatis
SEQUENCE: 117
AQPKSATAI                                                               9

SEQ ID NO: 118          moltype = AA   length = 9
FEATURE                 Location/Qualifiers
source                  1..9
                        mol_type = protein
                        organism = Chlamydia trachomatis
SEQUENCE: 118
QPKSATAIF                                                               9

SEQ ID NO: 119          moltype = AA   length = 9
FEATURE                 Location/Qualifiers
source                  1..9
                        mol_type = protein
                        organism = Chlamydia trachomatis
SEQUENCE: 119
PKSATAIFD                                                               9

SEQ ID NO: 120          moltype = AA   length = 9
FEATURE                 Location/Qualifiers
source                  1..9
                        mol_type = protein
                        organism = Chlamydia trachomatis
SEQUENCE: 120
KSATAIFDT                                                               9

SEQ ID NO: 121          moltype = AA   length = 9
FEATURE                 Location/Qualifiers
source                  1..9
                        mol_type = protein
                        organism = Chlamydia trachomatis
SEQUENCE: 121
SATAIFDTT                                                               9

SEQ ID NO: 122          moltype = AA   length = 9
FEATURE                 Location/Qualifiers
source                  1..9
                        mol_type = protein
                        organism = Chlamydia trachomatis
SEQUENCE: 122
ATAIFDTTT                                                               9

SEQ ID NO: 123          moltype = AA   length = 9
FEATURE                 Location/Qualifiers
source                  1..9
                        mol_type = protein
                        organism = Chlamydia trachomatis
SEQUENCE: 123
TAIFDTTTL                                                               9

SEQ ID NO: 124          moltype = AA   length = 9
FEATURE                 Location/Qualifiers
source                  1..9
                        mol_type = protein
                        organism = Chlamydia trachomatis
SEQUENCE: 124
AIFDTTTLN                                                               9

SEQ ID NO: 125          moltype = AA   length = 9
FEATURE                 Location/Qualifiers
source                  1..9
                        mol_type = protein
                        organism = Chlamydia trachomatis
SEQUENCE: 125
IFDTTTLNP                                                               9

SEQ ID NO: 126          moltype = AA   length = 9
FEATURE                 Location/Qualifiers
source                  1..9
                        mol_type = protein
                        organism = Chlamydia trachomatis
SEQUENCE: 126
FDTTTLNPT                                                               9
```

-continued

```
SEQ ID NO: 127          moltype = AA   length = 9
FEATURE                 Location/Qualifiers
source                  1..9
                        mol_type = protein
                        organism = Chlamydia trachomatis
SEQUENCE: 127
DTTTLNPTI                                                        9

SEQ ID NO: 128          moltype = AA   length = 9
FEATURE                 Location/Qualifiers
source                  1..9
                        mol_type = protein
                        organism = Chlamydia trachomatis
SEQUENCE: 128
TTTLNPTIA                                                        9

SEQ ID NO: 129          moltype = AA   length = 9
FEATURE                 Location/Qualifiers
source                  1..9
                        mol_type = protein
                        organism = Chlamydia trachomatis
SEQUENCE: 129
TLNPTIAGA                                                        9

SEQ ID NO: 130          moltype = AA   length = 9
FEATURE                 Location/Qualifiers
source                  1..9
                        mol_type = protein
                        organism = Chlamydia trachomatis
SEQUENCE: 130
LNPTIAGAG                                                        9

SEQ ID NO: 131          moltype = AA   length = 9
FEATURE                 Location/Qualifiers
source                  1..9
                        mol_type = protein
                        organism = Chlamydia trachomatis
SEQUENCE: 131
NPTIAGAGD                                                        9

SEQ ID NO: 132          moltype = AA   length = 9
FEATURE                 Location/Qualifiers
source                  1..9
                        mol_type = protein
                        organism = Chlamydia trachomatis
SEQUENCE: 132
PTIAGAGDV                                                        9

SEQ ID NO: 133          moltype = AA   length = 9
FEATURE                 Location/Qualifiers
source                  1..9
                        mol_type = protein
                        organism = Chlamydia trachomatis
SEQUENCE: 133
TIAGAGDVK                                                        9

SEQ ID NO: 134          moltype = AA   length = 9
FEATURE                 Location/Qualifiers
source                  1..9
                        mol_type = protein
                        organism = Chlamydia trachomatis
SEQUENCE: 134
IAGAGDVKT                                                        9

SEQ ID NO: 135          moltype = AA   length = 9
FEATURE                 Location/Qualifiers
source                  1..9
                        mol_type = protein
                        organism = Chlamydia trachomatis
SEQUENCE: 135
AGAGDVKTG                                                        9

SEQ ID NO: 136          moltype = AA   length = 9
FEATURE                 Location/Qualifiers
source                  1..9
                        mol_type = protein
                        organism = Chlamydia trachomatis
SEQUENCE: 136
```

-continued

```
GAGDVKTGA                                                          9

SEQ ID NO: 137          moltype = AA   length = 9
FEATURE                 Location/Qualifiers
source                  1..9
                        mol_type = protein
                        organism = Chlamydia trachomatis
SEQUENCE: 137
AGDVKTGAE                                                          9

SEQ ID NO: 138          moltype = AA   length = 9
FEATURE                 Location/Qualifiers
source                  1..9
                        mol_type = protein
                        organism = Chlamydia trachomatis
SEQUENCE: 138
GDVKTGAEG                                                          9

SEQ ID NO: 139          moltype = AA   length = 9
FEATURE                 Location/Qualifiers
source                  1..9
                        mol_type = protein
                        organism = Chlamydia trachomatis
SEQUENCE: 139
DVKTGAEGQ                                                          9

SEQ ID NO: 140          moltype = AA   length = 9
FEATURE                 Location/Qualifiers
source                  1..9
                        mol_type = protein
                        organism = Chlamydia trachomatis
SEQUENCE: 140
VKTGAEGQL                                                          9

SEQ ID NO: 141          moltype = AA   length = 9
FEATURE                 Location/Qualifiers
source                  1..9
                        mol_type = protein
                        organism = Chlamydia trachomatis
SEQUENCE: 141
KTGAEGQLG                                                          9

SEQ ID NO: 142          moltype = AA   length = 9
FEATURE                 Location/Qualifiers
source                  1..9
                        mol_type = protein
                        organism = Chlamydia trachomatis
SEQUENCE: 142
TGAEGQLGD                                                          9

SEQ ID NO: 143          moltype = AA   length = 9
FEATURE                 Location/Qualifiers
source                  1..9
                        mol_type = protein
                        organism = Chlamydia trachomatis
SEQUENCE: 143
GAEGQLGDT                                                          9

SEQ ID NO: 144          moltype = AA   length = 9
FEATURE                 Location/Qualifiers
source                  1..9
                        mol_type = protein
                        organism = Chlamydia trachomatis
SEQUENCE: 144
AEGQLGDTM                                                          9

SEQ ID NO: 145          moltype = AA   length = 9
FEATURE                 Location/Qualifiers
source                  1..9
                        mol_type = protein
                        organism = Chlamydia trachomatis
SEQUENCE: 145
EGQLGDTMQ                                                          9

SEQ ID NO: 146          moltype = AA   length = 9
FEATURE                 Location/Qualifiers
source                  1..9
                        mol_type = protein
                        organism = Chlamydia trachomatis
```

-continued

```
SEQUENCE: 146
GQLGDTMQI                                                                    9

SEQ ID NO: 147          moltype = AA  length = 9
FEATURE                 Location/Qualifiers
source                  1..9
                        mol_type = protein
                        organism = Chlamydia trachomatis
SEQUENCE: 147
QLGDTMQIV                                                                    9

SEQ ID NO: 148          moltype = AA  length = 9
FEATURE                 Location/Qualifiers
source                  1..9
                        mol_type = protein
                        organism = Chlamydia trachomatis
SEQUENCE: 148
LGDTMQIVS                                                                    9

SEQ ID NO: 149          moltype = AA  length = 9
FEATURE                 Location/Qualifiers
source                  1..9
                        mol_type = protein
                        organism = Chlamydia trachomatis
SEQUENCE: 149
SRASFDSDT                                                                    9

SEQ ID NO: 150          moltype = AA  length = 9
FEATURE                 Location/Qualifiers
source                  1..9
                        mol_type = protein
                        organism = Chlamydia trachomatis
SEQUENCE: 150
RASFDSDTI                                                                    9

SEQ ID NO: 151          moltype = AA  length = 9
FEATURE                 Location/Qualifiers
source                  1..9
                        mol_type = protein
                        organism = Chlamydia trachomatis
SEQUENCE: 151
ASFDSDTIR                                                                    9

SEQ ID NO: 152          moltype = AA  length = 9
FEATURE                 Location/Qualifiers
source                  1..9
                        mol_type = protein
                        organism = Chlamydia trachomatis
SEQUENCE: 152
SFDSDTIRI                                                                    9

SEQ ID NO: 153          moltype = AA  length = 9
FEATURE                 Location/Qualifiers
source                  1..9
                        mol_type = protein
                        organism = Chlamydia trachomatis
SEQUENCE: 153
FDSDTIRIA                                                                    9

SEQ ID NO: 154          moltype = AA  length = 9
FEATURE                 Location/Qualifiers
source                  1..9
                        mol_type = protein
                        organism = Chlamydia trachomatis
SEQUENCE: 154
DSDTIRIAQ                                                                    9

SEQ ID NO: 155          moltype = AA  length = 9
FEATURE                 Location/Qualifiers
source                  1..9
                        mol_type = protein
                        organism = Chlamydia trachomatis
SEQUENCE: 155
SDTIRIAQP                                                                    9

SEQ ID NO: 156          moltype = AA  length = 9
FEATURE                 Location/Qualifiers
source                  1..9
                        mol_type = protein
```

```
                          organism = Chlamydia trachomatis
SEQUENCE: 156
DTIRIAQPR                                                                          9

SEQ ID NO: 157            moltype = AA  length = 9
FEATURE                   Location/Qualifiers
source                    1..9
                          mol_type = protein
                          organism = Chlamydia trachomatis
SEQUENCE: 157
TIRIAQPRL                                                                          9

SEQ ID NO: 158            moltype = AA  length = 9
FEATURE                   Location/Qualifiers
source                    1..9
                          mol_type = protein
                          organism = Chlamydia trachomatis
SEQUENCE: 158
IRIAQPRLV                                                                          9

SEQ ID NO: 159            moltype = AA  length = 9
FEATURE                   Location/Qualifiers
source                    1..9
                          mol_type = protein
                          organism = Chlamydia trachomatis
SEQUENCE: 159
RIAQPRLVT                                                                          9

SEQ ID NO: 160            moltype = AA  length = 9
FEATURE                   Location/Qualifiers
source                    1..9
                          mol_type = protein
                          organism = Chlamydia trachomatis
SEQUENCE: 160
IAQPRLVTP                                                                          9

SEQ ID NO: 161            moltype = AA  length = 9
FEATURE                   Location/Qualifiers
source                    1..9
                          mol_type = protein
                          organism = Chlamydia trachomatis
SEQUENCE: 161
AQPRLVTPV                                                                          9

SEQ ID NO: 162            moltype = AA  length = 9
FEATURE                   Location/Qualifiers
source                    1..9
                          mol_type = protein
                          organism = Chlamydia trachomatis
SEQUENCE: 162
QPRLVTPVV                                                                          9

SEQ ID NO: 163            moltype = AA  length = 9
FEATURE                   Location/Qualifiers
source                    1..9
                          mol_type = protein
                          organism = Chlamydia trachomatis
SEQUENCE: 163
PRLVTPVVD                                                                          9

SEQ ID NO: 164            moltype = AA  length = 9
FEATURE                   Location/Qualifiers
source                    1..9
                          mol_type = protein
                          organism = Chlamydia trachomatis
SEQUENCE: 164
RLVTPVVDI                                                                          9

SEQ ID NO: 165            moltype = AA  length = 9
FEATURE                   Location/Qualifiers
source                    1..9
                          mol_type = protein
                          organism = Chlamydia trachomatis
SEQUENCE: 165
LVTPVVDIT                                                                          9

SEQ ID NO: 166            moltype = AA  length = 9
FEATURE                   Location/Qualifiers
source                    1..9
```

```
                            mol_type = protein
                            organism = Chlamydia trachomatis
SEQUENCE: 166
VTPVVDITT                                                              9

SEQ ID NO: 167              moltype = AA   length = 9
FEATURE                    Location/Qualifiers
source                     1..9
                           mol_type = protein
                           organism = Chlamydia trachomatis
SEQUENCE: 167
TPVVDITTL                                                              9

SEQ ID NO: 168              moltype = AA   length = 9
FEATURE                    Location/Qualifiers
source                     1..9
                           mol_type = protein
                           organism = Chlamydia trachomatis
SEQUENCE: 168
PVVDITTLN                                                              9

SEQ ID NO: 169              moltype = AA   length = 9
FEATURE                    Location/Qualifiers
source                     1..9
                           mol_type = protein
                           organism = Chlamydia trachomatis
SEQUENCE: 169
VVDITTLNP                                                              9

SEQ ID NO: 170              moltype = AA   length = 9
FEATURE                    Location/Qualifiers
source                     1..9
                           mol_type = protein
                           organism = Chlamydia trachomatis
SEQUENCE: 170
VDITTLNPT                                                              9

SEQ ID NO: 171              moltype = AA   length = 9
FEATURE                    Location/Qualifiers
source                     1..9
                           mol_type = protein
                           organism = Chlamydia trachomatis
SEQUENCE: 171
DITTLNPTI                                                              9

SEQ ID NO: 172              moltype = AA   length = 9
FEATURE                    Location/Qualifiers
source                     1..9
                           mol_type = protein
                           organism = Chlamydia trachomatis
SEQUENCE: 172
ITTLNPTIA                                                              9

SEQ ID NO: 173              moltype = AA   length = 9
FEATURE                    Location/Qualifiers
source                     1..9
                           mol_type = protein
                           organism = Chlamydia trachomatis
SEQUENCE: 173
TLNPTIAGC                                                              9

SEQ ID NO: 174              moltype = AA   length = 9
FEATURE                    Location/Qualifiers
source                     1..9
                           mol_type = protein
                           organism = Chlamydia trachomatis
SEQUENCE: 174
LNPTIAGCG                                                              9

SEQ ID NO: 175              moltype = AA   length = 9
FEATURE                    Location/Qualifiers
source                     1..9
                           mol_type = protein
                           organism = Chlamydia trachomatis
SEQUENCE: 175
NPTIAGCGS                                                              9

SEQ ID NO: 176              moltype = AA   length = 9
FEATURE                    Location/Qualifiers
```

-continued

| | | |
|---|---|---|
| source | 1..9 | |
| | mol_type = protein | |
| | organism = Chlamydia trachomatis | |
| SEQUENCE: 176 | | |
| PTIAGCGSV | | 9 |
| | | |
| SEQ ID NO: 177 | moltype = AA  length = 9 | |
| FEATURE | Location/Qualifiers | |
| source | 1..9 | |
| | mol_type = protein | |
| | organism = Chlamydia trachomatis | |
| SEQUENCE: 177 | | |
| TIAGCGSVA | | 9 |
| | | |
| SEQ ID NO: 178 | moltype = AA  length = 9 | |
| FEATURE | Location/Qualifiers | |
| source | 1..9 | |
| | mol_type = protein | |
| | organism = Chlamydia trachomatis | |
| SEQUENCE: 178 | | |
| IAGCGSVAG | | 9 |
| | | |
| SEQ ID NO: 179 | moltype = AA  length = 9 | |
| FEATURE | Location/Qualifiers | |
| source | 1..9 | |
| | mol_type = protein | |
| | organism = Chlamydia trachomatis | |
| SEQUENCE: 179 | | |
| AGCGSVAGA | | 9 |
| | | |
| SEQ ID NO: 180 | moltype = AA  length = 9 | |
| FEATURE | Location/Qualifiers | |
| source | 1..9 | |
| | mol_type = protein | |
| | organism = Chlamydia trachomatis | |
| SEQUENCE: 180 | | |
| GCGSVAGAN | | 9 |
| | | |
| SEQ ID NO: 181 | moltype = AA  length = 9 | |
| FEATURE | Location/Qualifiers | |
| source | 1..9 | |
| | mol_type = protein | |
| | organism = Chlamydia trachomatis | |
| SEQUENCE: 181 | | |
| CGSVAGANT | | 9 |
| | | |
| SEQ ID NO: 182 | moltype = AA  length = 9 | |
| FEATURE | Location/Qualifiers | |
| source | 1..9 | |
| | mol_type = protein | |
| | organism = Chlamydia trachomatis | |
| SEQUENCE: 182 | | |
| GSVAGANTE | | 9 |
| | | |
| SEQ ID NO: 183 | moltype = AA  length = 9 | |
| FEATURE | Location/Qualifiers | |
| source | 1..9 | |
| | mol_type = protein | |
| | organism = Chlamydia trachomatis | |
| SEQUENCE: 183 | | |
| SVAGANTEG | | 9 |
| | | |
| SEQ ID NO: 184 | moltype = AA  length = 9 | |
| FEATURE | Location/Qualifiers | |
| source | 1..9 | |
| | mol_type = protein | |
| | organism = Chlamydia trachomatis | |
| SEQUENCE: 184 | | |
| VAGANTEGQ | | 9 |
| | | |
| SEQ ID NO: 185 | moltype = AA  length = 9 | |
| FEATURE | Location/Qualifiers | |
| source | 1..9 | |
| | mol_type = protein | |
| | organism = Chlamydia trachomatis | |
| SEQUENCE: 185 | | |
| AGANTEGQI | | 9 |
| | | |
| SEQ ID NO: 186 | moltype = AA  length = 9 | |

-continued

```
FEATURE                Location/Qualifiers
source                 1..9
                       mol_type = protein
                       organism = Chlamydia trachomatis
SEQUENCE: 186
GANTEGQIS                                                        9

SEQ ID NO: 187         moltype = AA  length = 9
FEATURE                Location/Qualifiers
source                 1..9
                       mol_type = protein
                       organism = Chlamydia trachomatis
SEQUENCE: 187
ANTEGQISD                                                        9

SEQ ID NO: 188         moltype = AA  length = 9
FEATURE                Location/Qualifiers
source                 1..9
                       mol_type = protein
                       organism = Chlamydia trachomatis
SEQUENCE: 188
NTEGQISDT                                                        9

SEQ ID NO: 189         moltype = AA  length = 9
FEATURE                Location/Qualifiers
source                 1..9
                       mol_type = protein
                       organism = Chlamydia trachomatis
SEQUENCE: 189
TEGQISDTM                                                        9

SEQ ID NO: 190         moltype = AA  length = 9
FEATURE                Location/Qualifiers
source                 1..9
                       mol_type = protein
                       organism = Chlamydia trachomatis
SEQUENCE: 190
EGQISDTMQ                                                        9

SEQ ID NO: 191         moltype = AA  length = 9
FEATURE                Location/Qualifiers
source                 1..9
                       mol_type = protein
                       organism = Chlamydia trachomatis
SEQUENCE: 191
GQISDTMQI                                                        9

SEQ ID NO: 192         moltype = AA  length = 9
FEATURE                Location/Qualifiers
source                 1..9
                       mol_type = protein
                       organism = Chlamydia trachomatis
SEQUENCE: 192
QISDTMQIV                                                        9

SEQ ID NO: 193         moltype = AA  length = 9
FEATURE                Location/Qualifiers
source                 1..9
                       mol_type = protein
                       organism = Chlamydia trachomatis
SEQUENCE: 193
ISDTMQIVS                                                        9

SEQ ID NO: 194         moltype = AA  length = 17
FEATURE                Location/Qualifiers
source                 1..17
                       mol_type = protein
                       organism = Chlamydia trachomatis
SEQUENCE: 194
FDTTTLNPTI AGAGDVK                                               17

SEQ ID NO: 195         moltype = AA  length = 9
FEATURE                Location/Qualifiers
source                 1..9
                       mol_type = protein
                       organism = Chlamydia trachomatis
SEQUENCE: 195
NMFTPYIGV                                                        9
```

SEQ ID NO: 196            moltype = AA   length = 9
FEATURE                   Location/Qualifiers
source                    1..9
                          mol_type = protein
                          organism = Chlamydia trachomatis
SEQUENCE: 196
MFTPYIGVK                                                                 9

SEQ ID NO: 197            moltype = AA   length = 9
FEATURE                   Location/Qualifiers
source                    1..9
                          mol_type = protein
                          organism = Chlamydia trachomatis
SEQUENCE: 197
FTPYIGVKW                                                                 9

SEQ ID NO: 198            moltype = AA   length = 9
FEATURE                   Location/Qualifiers
source                    1..9
                          mol_type = protein
                          organism = Chlamydia trachomatis
SEQUENCE: 198
TPYIGVKWS                                                                 9

SEQ ID NO: 199            moltype = AA   length = 9
FEATURE                   Location/Qualifiers
source                    1..9
                          mol_type = protein
                          organism = Chlamydia trachomatis
SEQUENCE: 199
PYIGVKWSR                                                                 9

SEQ ID NO: 200            moltype = AA   length = 9
FEATURE                   Location/Qualifiers
source                    1..9
                          mol_type = protein
                          organism = Chlamydia trachomatis
SEQUENCE: 200
YIGVKWSRA                                                                 9

SEQ ID NO: 201            moltype = AA   length = 9
FEATURE                   Location/Qualifiers
source                    1..9
                          mol_type = protein
                          organism = Chlamydia trachomatis
SEQUENCE: 201
IGVKWSRAS                                                                 9

SEQ ID NO: 202            moltype = AA   length = 9
FEATURE                   Location/Qualifiers
source                    1..9
                          mol_type = protein
                          organism = Chlamydia trachomatis
SEQUENCE: 202
GVKWSRASF                                                                 9

SEQ ID NO: 203            moltype = AA   length = 9
FEATURE                   Location/Qualifiers
source                    1..9
                          mol_type = protein
                          organism = Chlamydia trachomatis
SEQUENCE: 203
VKWSRASFD                                                                 9

SEQ ID NO: 204            moltype = AA   length = 9
FEATURE                   Location/Qualifiers
source                    1..9
                          mol_type = protein
                          organism = Chlamydia trachomatis
SEQUENCE: 204
KWSRASFDA                                                                 9

SEQ ID NO: 205            moltype = AA   length = 9
FEATURE                   Location/Qualifiers
source                    1..9
                          mol_type = protein
                          organism = Chlamydia trachomatis
SEQUENCE: 205
WSRASFDAD                                                                 9

```
SEQ ID NO: 206            moltype = AA   length = 9
FEATURE                   Location/Qualifiers
source                    1..9
                          mol_type = protein
                          organism = Chlamydia trachomatis
SEQUENCE: 206
SRASFDADT                                                              9

SEQ ID NO: 207            moltype = AA   length = 9
FEATURE                   Location/Qualifiers
source                    1..9
                          mol_type = protein
                          organism = Chlamydia trachomatis
SEQUENCE: 207
RASFDADTI                                                             9

SEQ ID NO: 208            moltype = AA   length = 9
FEATURE                   Location/Qualifiers
source                    1..9
                          mol_type = protein
                          organism = Chlamydia trachomatis
SEQUENCE: 208
ASFDADTIR                                                             9

SEQ ID NO: 209            moltype = AA   length = 9
FEATURE                   Location/Qualifiers
source                    1..9
                          mol_type = protein
                          organism = Chlamydia trachomatis
SEQUENCE: 209
SFDADTIRI                                                             9

SEQ ID NO: 210            moltype = AA   length = 9
FEATURE                   Location/Qualifiers
source                    1..9
                          mol_type = protein
                          organism = Chlamydia trachomatis
SEQUENCE: 210
FDADTIRIA                                                             9

SEQ ID NO: 211            moltype = AA   length = 9
FEATURE                   Location/Qualifiers
source                    1..9
                          mol_type = protein
                          organism = Chlamydia trachomatis
SEQUENCE: 211
DADTIRIAQ                                                             9

SEQ ID NO: 212            moltype = AA   length = 9
FEATURE                   Location/Qualifiers
source                    1..9
                          mol_type = protein
                          organism = Chlamydia trachomatis
SEQUENCE: 212
ADTIRIAQP                                                             9

SEQ ID NO: 213            moltype = AA   length = 9
FEATURE                   Location/Qualifiers
source                    1..9
                          mol_type = protein
                          organism = Chlamydia trachomatis
SEQUENCE: 213
DTIRIAQPK                                                             9

SEQ ID NO: 214            moltype = AA   length = 9
FEATURE                   Location/Qualifiers
source                    1..9
                          mol_type = protein
                          organism = Chlamydia trachomatis
SEQUENCE: 214
TIRIAQPKS                                                             9

SEQ ID NO: 215            moltype = AA   length = 9
FEATURE                   Location/Qualifiers
source                    1..9
                          mol_type = protein
                          organism = Chlamydia trachomatis
SEQUENCE: 215
```

-continued

```
IRIAQPKSA                                                                    9

SEQ ID NO: 216              moltype = AA   length = 9
FEATURE                     Location/Qualifiers
source                      1..9
                            mol_type = protein
                            organism = Chlamydia trachomatis
SEQUENCE: 216
RIAQPKSAT                                                                    9

SEQ ID NO: 217              moltype = AA   length = 9
FEATURE                     Location/Qualifiers
source                      1..9
                            mol_type = protein
                            organism = Chlamydia trachomatis
SEQUENCE: 217
IAQPKSATA                                                                    9

SEQ ID NO: 218              moltype = AA   length = 9
FEATURE                     Location/Qualifiers
source                      1..9
                            mol_type = protein
                            organism = Chlamydia trachomatis
SEQUENCE: 218
AQPKSATAI                                                                    9

SEQ ID NO: 219              moltype = AA   length = 9
FEATURE                     Location/Qualifiers
source                      1..9
                            mol_type = protein
                            organism = Chlamydia trachomatis
SEQUENCE: 219
QPKSATAIF                                                                    9

SEQ ID NO: 220              moltype = AA   length = 9
FEATURE                     Location/Qualifiers
source                      1..9
                            mol_type = protein
                            organism = Chlamydia trachomatis
SEQUENCE: 220
PKSATAIFD                                                                    9

SEQ ID NO: 221              moltype = AA   length = 9
FEATURE                     Location/Qualifiers
source                      1..9
                            mol_type = protein
                            organism = Chlamydia trachomatis
SEQUENCE: 221
KSATAIFDT                                                                    9

SEQ ID NO: 222              moltype = AA   length = 9
FEATURE                     Location/Qualifiers
source                      1..9
                            mol_type = protein
                            organism = Chlamydia trachomatis
SEQUENCE: 222
SATAIFDTT                                                                    9

SEQ ID NO: 223              moltype = AA   length = 9
FEATURE                     Location/Qualifiers
source                      1..9
                            mol_type = protein
                            organism = Chlamydia trachomatis
SEQUENCE: 223
ATAIFDTTT                                                                    9

SEQ ID NO: 224              moltype = AA   length = 9
FEATURE                     Location/Qualifiers
source                      1..9
                            mol_type = protein
                            organism = Chlamydia trachomatis
SEQUENCE: 224
TAIFDTTTL                                                                    9

SEQ ID NO: 225              moltype = AA   length = 9
FEATURE                     Location/Qualifiers
source                      1..9
                            mol_type = protein
                            organism = Chlamydia trachomatis
```

-continued

```
SEQUENCE: 225
AIFDTTTLN                                                                9

SEQ ID NO: 226           moltype = AA   length = 9
FEATURE                  Location/Qualifiers
source                   1..9
                         mol_type = protein
                         organism = Chlamydia trachomatis
SEQUENCE: 226
IFDTTTLNP                                                                9

SEQ ID NO: 227           moltype = AA   length = 9
FEATURE                  Location/Qualifiers
source                   1..9
                         mol_type = protein
                         organism = Chlamydia trachomatis
SEQUENCE: 227
FDTTTLNPT                                                                9

SEQ ID NO: 228           moltype = AA   length = 9
FEATURE                  Location/Qualifiers
source                   1..9
                         mol_type = protein
                         organism = Chlamydia trachomatis
SEQUENCE: 228
DTTTLNPTI                                                                9

SEQ ID NO: 229           moltype = AA   length = 9
FEATURE                  Location/Qualifiers
source                   1..9
                         mol_type = protein
                         organism = Chlamydia trachomatis
SEQUENCE: 229
TTTLNPTIA                                                                9

SEQ ID NO: 230           moltype = AA   length = 9
FEATURE                  Location/Qualifiers
source                   1..9
                         mol_type = protein
                         organism = Chlamydia trachomatis
SEQUENCE: 230
TTLNPTIAG                                                                9

SEQ ID NO: 231           moltype = AA   length = 9
FEATURE                  Location/Qualifiers
source                   1..9
                         mol_type = protein
                         organism = Chlamydia trachomatis
SEQUENCE: 231
TLNPTIAGA                                                                9

SEQ ID NO: 232           moltype = AA   length = 9
FEATURE                  Location/Qualifiers
source                   1..9
                         mol_type = protein
                         organism = Chlamydia trachomatis
SEQUENCE: 232
LNPTIAGAG                                                                9

SEQ ID NO: 233           moltype = AA   length = 9
FEATURE                  Location/Qualifiers
source                   1..9
                         mol_type = protein
                         organism = Chlamydia trachomatis
SEQUENCE: 233
NPTIAGAGD                                                                9

SEQ ID NO: 234           moltype = AA   length = 9
FEATURE                  Location/Qualifiers
source                   1..9
                         mol_type = protein
                         organism = Chlamydia trachomatis
SEQUENCE: 234
PTIAGAGDV                                                                9

SEQ ID NO: 235           moltype = AA   length = 9
FEATURE                  Location/Qualifiers
source                   1..9
                         mol_type = protein
```

-continued

```
                         organism = Chlamydia trachomatis
SEQUENCE: 235
TIAGAGDVK                                                                  9

SEQ ID NO: 236           moltype = AA   length = 9
FEATURE                  Location/Qualifiers
source                   1..9
                         mol_type = protein
                         organism = Chlamydia trachomatis
SEQUENCE: 236
IAGAGDVKT                                                                  9

SEQ ID NO: 237           moltype = AA   length = 9
FEATURE                  Location/Qualifiers
source                   1..9
                         mol_type = protein
                         organism = Chlamydia trachomatis
SEQUENCE: 237
AGAGDVKTG                                                                  9

SEQ ID NO: 238           moltype = AA   length = 9
FEATURE                  Location/Qualifiers
source                   1..9
                         mol_type = protein
                         organism = Chlamydia trachomatis
SEQUENCE: 238
GAGDVKTGA                                                                  9

SEQ ID NO: 239           moltype = AA   length = 9
FEATURE                  Location/Qualifiers
source                   1..9
                         mol_type = protein
                         organism = Chlamydia trachomatis
SEQUENCE: 239
AGDVKTGAE                                                                  9

SEQ ID NO: 240           moltype = AA   length = 9
FEATURE                  Location/Qualifiers
source                   1..9
                         mol_type = protein
                         organism = Chlamydia trachomatis
SEQUENCE: 240
GDVKTGAEG                                                                  9

SEQ ID NO: 241           moltype = AA   length = 9
FEATURE                  Location/Qualifiers
source                   1..9
                         mol_type = protein
                         organism = Chlamydia trachomatis
SEQUENCE: 241
DVKTGAEGQ                                                                  9

SEQ ID NO: 242           moltype = AA   length = 9
FEATURE                  Location/Qualifiers
source                   1..9
                         mol_type = protein
                         organism = Chlamydia trachomatis
SEQUENCE: 242
VKTGAEGQL                                                                  9

SEQ ID NO: 243           moltype = AA   length = 9
FEATURE                  Location/Qualifiers
source                   1..9
                         mol_type = protein
                         organism = Chlamydia trachomatis
SEQUENCE: 243
KTGAEGQLG                                                                  9

SEQ ID NO: 244           moltype = AA   length = 9
FEATURE                  Location/Qualifiers
source                   1..9
                         mol_type = protein
                         organism = Chlamydia trachomatis
SEQUENCE: 244
TGAEGQLGD                                                                  9

SEQ ID NO: 245           moltype = AA   length = 9
FEATURE                  Location/Qualifiers
source                   1..9
```

-continued

```
                          mol_type = protein
                          organism = Chlamydia trachomatis
SEQUENCE: 245
GAEGQLGDT                                                           9

SEQ ID NO: 246           moltype = AA   length = 9
FEATURE                  Location/Qualifiers
source                   1..9
                         mol_type = protein
                         organism = Chlamydia trachomatis
SEQUENCE: 246
AEGQLGDTM                                                           9

SEQ ID NO: 247           moltype = AA   length = 9
FEATURE                  Location/Qualifiers
source                   1..9
                         mol_type = protein
                         organism = Chlamydia trachomatis
SEQUENCE: 247
EGQLGDTMQ                                                           9

SEQ ID NO: 248           moltype = AA   length = 9
FEATURE                  Location/Qualifiers
source                   1..9
                         mol_type = protein
                         organism = Chlamydia trachomatis
SEQUENCE: 248
GQLGDLMQI                                                           9

SEQ ID NO: 249           moltype = AA   length = 9
FEATURE                  Location/Qualifiers
source                   1..9
                         mol_type = protein
                         organism = Chlamydia trachomatis
SEQUENCE: 249
QLGDTMQIV                                                           9

SEQ ID NO: 250           moltype = AA   length = 9
FEATURE                  Location/Qualifiers
source                   1..9
                         mol_type = protein
                         organism = Chlamydia trachomatis
SEQUENCE: 250
LGDTMQIVS                                                           9

SEQ ID NO: 251           moltype = AA   length = 9
FEATURE                  Location/Qualifiers
source                   1..9
                         mol_type = protein
                         organism = Chlamydia trachomatis
SEQUENCE: 251
GDTMQIVSL                                                           9

SEQ ID NO: 252           moltype = AA   length = 9
FEATURE                  Location/Qualifiers
source                   1..9
                         mol_type = protein
                         organism = Chlamydia trachomatis
SEQUENCE: 252
DTMQIVSLQ                                                           9

SEQ ID NO: 253           moltype = AA   length = 9
FEATURE                  Location/Qualifiers
source                   1..9
                         mol_type = protein
                         organism = Chlamydia trachomatis
SEQUENCE: 253
TMQIVSLQL                                                           9

SEQ ID NO: 254           moltype = AA   length = 9
FEATURE                  Location/Qualifiers
source                   1..9
                         mol_type = protein
                         organism = Chlamydia trachomatis
SEQUENCE: 254
MQIVSLQLN                                                           9

SEQ ID NO: 255           moltype = AA   length = 80
FEATURE                  Location/Qualifiers
```

-continued

```
source              1..80
                    mol_type = protein
                    organism = Chlamydia trachomatis
SEQUENCE: 255
EWQASLALSY RLNMFTPYIG VKWSRASFDA DTIRIAQPKS ATAIFDTTTL NPTIAGAGDV  60
KTGAEGQLGD TMQIVSLQLN                                               80
```

VACCINES AGAINST *CHLAMYDIA* SP

CROSS-REFERENCE OF RELATED APPLICATIONS

This divisional application claims priority to U.S. patent application Ser. No. 17/155,264 filed Apr. 18, 2018, now U.S. Pat. No. 10,925,954, which is a continuation U.S. patent application Ser. No. 14/216,403, filed Mar. 17, 2024 now abandoned, which in turn claims priority to U.S. Provisional Application No. 61/802,907 filed Mar. 18, 2013, Denmark PA 2013 00684 filed Dec. 11, 2013 and Denmark PA 2013 00155 filed Mar. 18, 2013, each of the aforementioned patents being incorporated herein by reference as though set forth in full.

INCORPORATION-BY-REFERENCE OF MATERIAL SUBMITTED IN ELECTRONIC FORM

The Contents of the electronic sequence listing (SSI-15049-US05.xml; Size: 236,007 bytes; and Date of Creation: Apr. 30, 2025 is herein incorporated by reference in its entirety.

FIELD OF INVENTION

The present invention relates to polypeptides of repetitive units of immunogenic fragments of surface exposed regions of outer membrane proteins of *Chlamydia* sp. and pharmaceutical compositions and vaccines comprising these fusion proteins.

BACKGROUND OF THE INVENTION

Chlamydiae are intracellular bacterial pathogens responsible for a variety of infections. *Chlamydia pneumoniae* is responsible for human acute respiratory infection and believed to play a role in coronary heart disease. *Chlamydia trachomatis* is the causative agent of human sexually transmitted disease and eye infections (Trachoma). Also in animals, several infections with *Chlamydia* sp. are known, e.g. *Chlamydia suis* infecting pigs, and *Chlamydiaphila abortus* which causes abortion in small ruminants (sheep and goats).

Worldwide, it is estimated that 92 million individuals become sexually infected with *Chlamydia trachomatis* (Ct) [1]. Urogenital infections with Ct are of public health concern because of its high prevalence and the fact that it's a risk factor for ectopic pregnancy and infertility[2]. In addition to this Ct infections have been shown to facilitate the transmission of HIV[3] and act as a co-factor in HPV-induced cervical carcinoma[4]. The duration of untreated genital Ct infection can be prolonged, and complete clearance is often not reached within the first 12 months[5]. From human studies it is known that some degree of protective immunity against genital re-infection develops, although it appears at best to be partial[6]. The infection is effectively controlled by antibiotic therapy; however the high prevalence of asymptomatic cases suggests that sustainable disease control can only be envisaged if an effective Chlamydia vaccine is developed.

A vaccine against Ct needs to elicit protective T-cell and B-cell immunity in the genital tract mucosa 7. Immune mechanisms of clearance of infection and resistance to re-infection have been described in numerous studies. A variety of animal models and chlamydial species have been used in attempts to identify protective and damaging immune responses. A general consensus has emerged that, in mice, CD4+ Th1 cell mediated immune responses plays a major role in the resolution of Ct infection[8, 9, 10], whereas the role of humoral immunity in protection has remained less well defined. In guinea pigs immunity to chlamydial infection is mediated at least partly by secretory IgA at the mucosal surface[11, 12] and also in the mouse model there is increasing evidence to support a role for antibodies in protective immunity[9]. Data from animal models that has emerged over the last years clearly demonstrate that if antibodies are formed after the infection is established they play a minimal role, whereas their presence at the time of infection (e.g. in a secondary response) promotes significant levels of protection, an effect that is however clearly amplified in the presence of *Chlamydia* specific CD4$^+$ cells[9, 13, 14]. A strong cell mediated immune (CMI) response without antibodies may on the other hand control bacterial replication but can in the worst case exacerbate the pathology associated with *Chlamydia* infection[15, 16]. The importance of this interplay between cell mediated immunity and antibodies is also becoming increasingly clear to support a preferential role of neutralizing antibodies in the initial phase of infection, whereas CD4$^+$ cells are the main effectors throughout the rest of the infection[17, 18, 19]. In summary balancing the immune effector mechanisms between antibodies and T cells seems to be crucial for disease outcome.

We and others have identified a range of chlamydial antigens recognized during a natural infection in either humans or animal models[20, 21, 22, 23, 24, 25, 26, 27]. Especially the publishing of the genome sequence in 1998 and modern high throughput techniques have led to the testing of almost the entire genome of 875 open reading frames[28]. Importantly, identifying proteins as antigenic during an infection do not necessarily mean they are protective as vaccines[29] and despite the characterization of such a large number of antigens only very few of these have been demonstrated to mediate protection as vaccines in animal models[30, 31, 32] Furthermore for the majority of the vaccines recently reported the partial protection observed is mediated by T cells with no neutralizing antibodies. Therefore there is a lack of vaccine candidates that generate neutralizing antibodies that can cope with the infection in the initial phase and creating a balanced immune response.

Until now there has only been convincing data on neutralizing antibodies with three surface exposed antigens; PorB, which localized in the chlamydial outer membrane and functions as a porin[33]. Antibodies against this has been shown to neutralize chlamydial infectivity[34], patent ref: U.S. Pat. No. 7,105,171. Another more recent antigen is PmpD. This protein has been shown to generate neutralizing antibodies in vitro, however the in vivo relevance of these antibodies have not yet been demonstrated[35].

MOMP is the classical target antigen for neutralizing antibodies and one of the first antigenic molecules described. It is a surface-exposed trans membrane protein which has structural (porin) properties[36, 37, 38]. MOMP is a 40 kDa protein making up roughly 60% of the protein in the Ct membrane and is a target for neutralizing antibodies with proven efficacy both in vitro and in vivo. MOMP consists of four variable surface exposed domains (VD-1 to VD-4) separated by five constant segments[36, 39] and it is the molecular basis of the serovar (~15) grouping of Chlamydia (FIG. 1). The in vitro and in vivo neutralizing antibody epitopes have been mapped to these VDs[40, 41, 42, 43, 44]. The distribution profile of Ct urogenital serovars has been described for regions worldwide, providing epidemiological data for the serovar coverage needed of a MOMP based vaccine. The most common serovar detected worldwide is E (22-49% of cases) followed by serovars F and D (17-22% and 9-19%, respectively)[45 46 47 48 49 50], meaning that a vaccine targeting serovars E, D and F would have a significant impact and cover more than 70% of the human population.

MOMP is highly immunogenic in humans and animals and has therefore been studied in great detail as a vaccine candidate, both as a natively purified protein, recombinantly and as DNA-vaccine. These vaccination attempts gave variable results[17, 51, 52, 53, 54, 55, 56, 57] The reason for the relative inconsistency of MOMP as a vaccine is not fully understood, but the fact that the synthetic MOMP immunogens do not mimic the native structure of the protein has been the major concern 54. In this regard, the structure of this membrane bound cysteine rich molecule and refolding various products to achieve native protein structure has been extremely challenging and is not suitable for large scale vaccine production[58]. Therefore, although clearly with vaccine potential, full size MOMP has so far not been a feasible vaccine candidate and several attempts have therefore been made to construct a vaccine based on selected epitopes (such as the highly conserved TTLNPTIAG (SEQ ID NO: 76) in VD4[36, 59]) or based on selected regions rich in neutralizing target epitopes (such as the VD's) from MOMP (WO9406827, U.S. Pat. No. 6,384,206)[60, 61 62, 63 64 51, 65 66].

There has been special focus on VD1, VD2 and VD4 because neutralizing monoclonal antibodies used for serotyping has been shown to map to these regions. These VD regions are targeted by antibodies during natural infection and in line with this, these regions have naturally been the focus of attempts to develop immuno-diagnostics. For example Mygind et al. constructed different polyantigens containing VD regions from different serovariants in the search for a diagnostic tool based on ELISA[67]. This analysis revealed that by increasing the number of serovariants and include the species specific TTLNPTIAG (SEQ ID NO: 76) into one recombinant polyantigen, it was possible to increase the specificity and sensitivity of the assay compared to an assay based on a single serovariant antigen.

Mainly VD4 has attracted interest as an immunogen because this region was shown to contain the highly conserved species-specific epitope TTLNPTIAG (SEQ ID NO: 76) embedded in the variable region. Importantly, this conserved epitope in the VD4 region can elicit a broadly cross-reactive immune response, which is able to neutralize multiple serovars, among them the most prevalent D, E and F (FIG. 2). Peptides representing the VD4 region or the conserved epitope derived from this region have been used for immunization either alone, as chimeric peptides fused to other regions such as VD1 or mixed with T cell epitopes to potentiate the antibody response[60, 68 51, 65 64 69]. All these constructs generated antibodies with some functional capabilities of neutralizing the infection in vitro but in general these strategies suffer from a low immunogenicity and the titres did not translate into in vivo protective efficacy against genital chlamydial challenge.

Reasons for the lack of protection when using these peptide based constructs can be numerous; including route of administration, type of immune response elicited, challenge dose, but most likely reflects that the vaccine molecule is not sufficiently immunogenic for use as a vaccine. The VD4 based strategy furthermore suffers from the limitation that with the exception of the TTLNPTIAG (SEQ ID NO: 76) epitope, these fragments as mentioned above are highly specific for one or two serovariants and a vaccine would accordingly have to be composed of several components to cover the most frequent serovariants causing human disease.

In WO2012172042 it has previously been disclosed that B-cell epitopes within the VD regions, combined with defined T cell (Th1 and Th2) epitopes from non-variable domains of MOMP, could function as a poly-epitope vaccine against *Chlamydia psitattci* serovar D in chickens; in the examples they describe the combination of up to three B-cell epitopes each derived from a VD region from different variable domains of the same serovariant together with several T-cell epitopes. The use of repeats of a variable domain of a surface exposed region of MOMP and using different serovariants is not suggested and thus high titers and a broad response against different serovariants is not obtained.

The object of the current invention is to prepare recombinant fusion molecules that are capable of generating a high titered neutralizing antibody response that is protective against various Ct serovars in vivo. Our invention furthermore describes the combination of these antibody promoting fragments with Ct antigens that are targets for T cells with the aim to provide a vaccine that activate both arms of the immune system.

SUMMARY OF THE INVENTION

The present invention discloses an efficient vaccine against a pathogen, e.g. *Chlamydia trachomatis* (Ct), that incorporates repeats of surface exposed fragments of Ct antigens (homologous immuno-repeats) for maximal antibody responses. In one embodiment of the invention, these surface exposed fragments are extended to cover the flanking region of the surface exposed fragments that may contain T cell epitopes. One example is a defined large fragment representing an extended version of the VD1 or VD4 region from the Ct MOMP antigen and in the immuno-repeat format provides high levels of surface binding and neutralizing antibodies against Ct. In another important embodiment the immuno-repeat technology is used to obtain high titers and a broad response against different serovariants by the fusion of fragments that contain variable B and T cell epitopes from different serovariants (heterologous immuno-repeats). In yet another embodiment of our invention these surface exposed repeats are recombinantly fused with fragments of other surface exposed antigens such as PMPs or OMPs. Finally our invention discloses combinations of these immuno-repeat constructs with strong T cell antigens, such as MOMP (CT681), CT043 or CT004 from Ct that together form a very efficient vaccine against the different infectious stages of Ct infection.

BRIEF DESCRIPTION OF THE SEVERAL VIEWS OF THE DRAWINGS

FIG. 2. Alignment of amino acid sequence of Ct MOMP VD4[ext] for serovars D, E, F, G, Ia and J. The serovar D sequence is used as prototype, and conserved amino acids in other serovars are shown as ".". The variable domain VD4 according to Baehr et al (PNAS, 1988) 36 is shaded in gray and the conserved epitope TTLNPTIAG (SEQ ID NO: 76) is boxed. S vD VD4[ext] (SEQ ID NO: 23), S vE VD4[ext] (SEQ ID NO: 24), S vF VD4[ext] (SEQ ID NO: 25), S vG VD4[ext] (SEQ ID NO: 26), S vI VD4[ext] (SEQ ID NO: 27), and S vJ VD4[ext] (SEQ ID NO: 26) are shown.

FIGS. 7A, 7B, 7C-A, 7C-A1, 7C-B, 7C-B1, 7C-C, 7C-C1, 7D-A, 7D-B, 7D-C. Fine specificity of the antibody responses after immunization with a heterologous immuno-repeat of the extended VD4 units from S vD, E, and F (CTH89) compared to constructs composed of a homologous immuno-repeat from (S vE$^{ext}$VD4)*4 and from (S vF$^{ext}$·VD4)*4. In FIGS. 7A-7B, the Serovar E sequence shown is SEQ ID NO: 24, and the Serovar F sequence shown is SEQ ID NO: 25. In FIGS. 7C-A through 7D-C, each set of overlapping peptides is NMFTPYIGV through MQI-VSLQLN, corresponding to SEQ ID NO: 195 through SEQ ID NO: 254, respectively. (See Example 3).

FIG. 9. In vivo neutralization with CTH89 specific serum.

FIGS. 11A-11C. Vaccination with heterologous immuno-repeats of VD1-VD4's regions from S vD, S vE and S vF (CTH88) compared to vaccination with a single VD1-VD4 unit from S vD (CTH87)

DETAILED DISCLOSURE OF THE INVENTION

Figure 1:
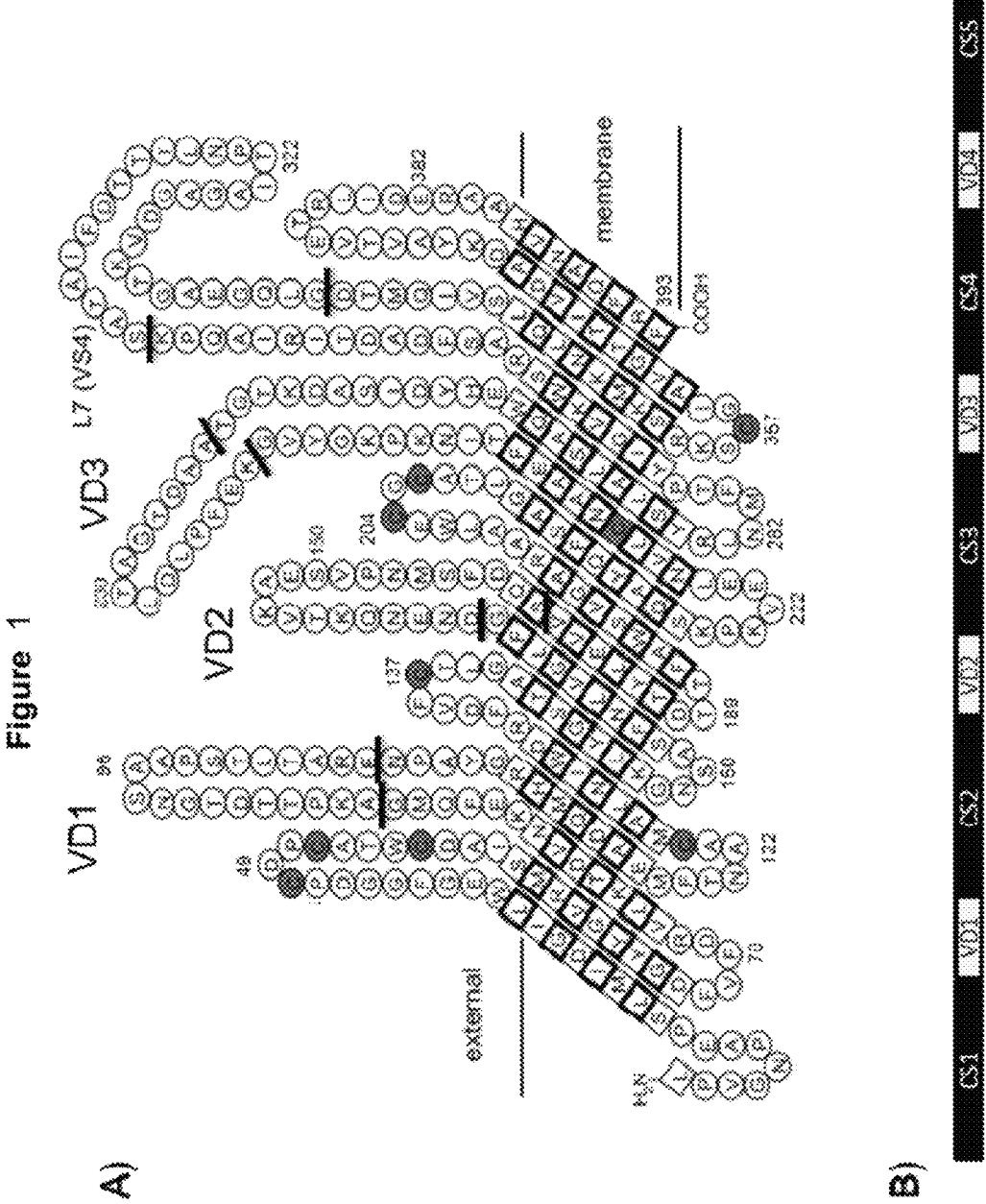
FIG. 1. Model of MOMP (Serovar D, strain: D/B-120) membrane topology adapted from Findlay et al[77]. The VD1, VD2, VD3 and VD4 are marked by black lines in the AA sequence (SEQ ID NO: 68) and in the linear model MOMP depicted interspaced with 5 constant segments (CS).

The invention discloses a polypeptide comprising
a) an amino acid sequence comprising one or more surface exposed fragments of the same outer membrane protein expressed in a serotype of *Chlamydia* sp.; and
b) two or more additional amino acid sequences which is either the same sequence as defined in a) or is the corresponding surface exposed fragments from a variant of said outer membrane protein expressed in a serotype of *Chlamydia* sp., which is different from the serotype in a).

The invention thus discloses polypeptides comprising immuno-repeats, which is 3 or more such as 4 or more repeats of an amino acid sequence comprising an immunogenic portion of a surface exposed region of an outer membrane protein of *Chlamydia* sp. Hence the invention can be described as a polypeptide comprising an amino acid sequence comprising one or more surface expose fragments of the same outer membrane protein expressed in a serotype of *Chlamydia* sp. and two or more such as three or more additional amino acid sequences which is either the same sequence as defined in a) or is the corresponding surface exposed fragments from a variant of said outer membrane protein expressed in a serotype of *Chlamydia* sp., which is different from the serotype in a).

In a preferred embodiment the polypeptide comprises 3 or more different amino acid sequences, where said amino acid sequences each comprises one or more surface exposed fragments from different variants or isotypes of the same outer membrane protein that varies in different *Chlamydia* sp. serotypes, said amino acid sequences derived from different *Chlamydia* sp. serotypes (heterologous immuno-repeats in our terminology), but the invention also discloses a polypeptide comprising 3 or more repetitions of an amino acid sequence, where said amino acid sequence comprises one or more surface exposed fragments of the same outer membrane protein that varies in different *Chlamydia* sp. serotypes, said amino acid sequences derived from the same *Chlamydia* sp. serotype (homologous immuno-repeats in our terminology).

The outer membrane protein is preferable the major outer membrane protein (MOMP) from any *Chlamydia* sp. serotype and the surface exposed fragment is chosen from variable domain 1 (VD1), variable domain 2 (VD2), variable domain 3 (VD3) or variable domain 4 (VD4) of MOMP. The surface exposed fragment can optionally be linearized by substitution of cysteine in the amino acid sequence to prevent disulfide bonds.

A preferred embodiment of the invention is polypeptides comprising immuno-repeats with 3 or more repeats of the variable domain 4 (VD4) of MOMP from any of serovars D, E, F, G, Ia and J of *Chlamydia trachomatis*, where each variable domain consists of an amino acid sequence, which corresponds to the position of amino acid residues Nos. 309-338 in the amino acid sequence of MOMP of *Chlamydia trachomatis* serovar D (S vD) (SEQ ID NO: 68) and where the variable domains in the immune-repeat is independently selected from the group consisting of the VD4 of serovar D, the VD4 of serovar E, the VD4 of serovar F, the VD4 of serovar G, the VD4 of serovar Ia and the VD4 of serovar J of *Chlamydia trachomatis* or has 80% sequence identity herewith.

The amino acid sequence of VD4 from serovar D, E, F, G, Ia and J corresponds to SEQ ID NO: 15-20 respectively. Each variable domain can additionally be flanked/extended on the N-terminal side by either
i) The amino acid sequence EWQASLAL-SYRLNMFTPYIGVKWSRASFDADTIRIAQPK (SEQ ID NO: 21) or ii) A subsequence of the amino acid sequence in i) said subsequence comprising 1 or more amino acid residues, On the C-terminal side the variable domain can additionally be flanked/extended by iii) The amino acid sequence DTMQI-VSLQLNKMKSRKSCGIAVGTTIVDA (SEQ ID NO: 22)

iv) A subsequence of the amino acid sequence in iv) said subsequence comprising 1 or more amino acid residues, or an amino acid sequence which has at least 80% sequence identity herewith.

Hence the preferred embodiment can be described as polypeptides comprising 2-8 different amino acid sequences each derived from MOMP from *Chlamydia trachomatis* which comprises an amino acid sequence defined in formula I:

$$xx_1\text{-VD4-}xx_2 \qquad \text{(Formula I)}$$

wherein

VD4 is independently selected from SEQ ID NO: 15-20 or an amino acid sequence which has at least 80% sequence identity herewith, and $xx_1$ consists of i) The amino acid sequence EWQASLAL-SYRLNMFTPYIGVKWSRASFDADTIRIAQPK (SEQ ID NO: 21) or ii) A subsequence of the amino acid sequence in i) said subsequence comprising 1-38 amino acid residues, starting with the C-terminal K in the amino acid sequence in i) and $xx_2$ consists of iii) The amino acid sequence DTMQI-VSLQLNKMKSRKSCGIAVGTTIVDA (SEQ ID NO: 22)

v) A subsequence of the amino acid sequence in iii) said subsequence comprising 1-29 amino acid residues, starting with the N-terminal D in the amino acid sequence in iii).

Examples of fusion proteins comprising immuno-repeats of VD4 of MOMP is indicated by SEQ ID NO: 49-59.

In another embodiment of the invention the polypeptide additionally comprises immuno-repeats of 3 or more variable domain 1 (VD1) of MOMP from any of serovars D, E, F, G, Ia and J of *Chlamydia trachomatis*, each variable domain consisting of an amino acid sequence, which corresponds to position of amino acid residues nos. 91-105 in the amino acid sequence of MOMP of *Chlamydia trachomatis* serovar D (S vD) (SEQ ID NO: 68) and is independently selected from the group consisting of the VD1 of serovar D, the VD1 of serovar E, the VD1 of serovar F, the VD1 of serovar G, the VD1 of serovar Ia and the VD1 of serovar J of *Chlamydia trachomatis* or has 80% sequence identity herewith.

The amino acid sequence of VD1 from serovar D, E, F, G, Ia and J corresponds to SEQ ID NO: 1-6 respectively. Each variable domain can additionally be flanked/extended on the N-terminal side by either vi) The amino acid sequence SMRVGYYGDFVFDRVLKTDVNKEFQMG (SEQ ID NO: 77)

vii) A subsequence of the amino acid sequence in v) said subsequence comprising 1 or more amino acid residues.

On the C-terminal side the variable domain can additionally be flanked/extended by viii) The amino acid sequence NPAYGRHMQDAEMFTNAACMALNIWD (SEQ ID NO: 78)

ix) A subsequence of the amino acid sequence in x) said subsequence comprising 1 or more amino acid residues;

Or an amino acid sequence which has at least 80% sequence identity herewith.

Hence another preferred embodiment can be described as polypeptides comprising 2-8 different amino acid sequences each derived from MOMP from *Chlamydia trachomatis* which comprises an amino acid sequence defined in formula I and additionally comprising an amino acid sequence defined in formula II:

$$yy_1\text{-VD1-}yy_2 \qquad \text{(Formula II)}$$

wherein

VD1 is independently selected from SEQ ID NO: 1-6 or an amino acid sequence which has at least 80% sequence identity herewith, and $yy_1$ consists of v) The amino acid sequence DAISMRVGYYGDFVFDRVLKTDVNKEFQMG (SEQ ID NO: 7) or vi) A subsequence of the amino acid sequence in v) said subsequence comprising 1-30 amino acid residues, starting with the C-terminal G in the amino acid sequence in v)

and $yy_2$ consists of vii) The amino acid sequence NPAYGRHMQDAEMFT-NAA (SEQ ID NO: 8) or viii) A subsequence of the amino acid sequence in vii) said subsequence comprising 1-18 amino acid residues, starting with the N-terminal N in the amino acid sequence in vii).

Examples of polypeptides comprising immuno-repeats of VD1 is indicated by SEQ ID NO: 9-14 and 45-48.

Further embodiments of the invention comprises additionally comprises a fragment comprising the variable domains 2 (VD2) and/or variable domains 3 (VD3) of MOMP respectively comprising an amino acid sequence defined in formula III and/or formula IV:

$$zz_1\text{-VD2-}zz_2 \qquad \text{(Formula III)}$$

$$qq1\text{-VD3-}qq2 \qquad \text{(Formula IV)}$$

wherein

VD2 is independently selected from SEQ ID NO: 29-34 or an amino acid sequence which has at least 80% sequence identity herewith, and $zz_1$ consists of ix) The amino acid sequence TLGATSGYLKGN-SASFNLVGLFG (SEQ ID NO: 35) or x) A subsequence of the amino acid sequence in ix) said subsequence comprising 1-23 amino acid residues, starting with the C-terminal G in the amino acid sequence in ix)

and $zz_2$ consists of xi) The amino acid sequence VVELYTDTTFAWSVGA-RAALWE (SEQ ID NO: 36) or xii) A subsequence of the amino acid sequence in xi) said subsequence comprising 1-22 amino acid residues, starting with the N-terminal V in the amino acid sequence in xi).

And wherein wherein

VD3 is independently selected from SEQ ID NO: 37-42 or an amino acid sequence which has at least 80% sequence identity herewith, and $qq_1$ consists of xiii) The amino acid sequence ATL-GASFQYAQSKPKVEELNVLCNAAEFT-INKPKGYVG (SEQ ID NO: 43) or xiv) A subsequence of the amino acid sequence in xiii) said subsequence comprising 1-22 amino acid residues, starting with the C-terminal G in the amino acid sequence in xiii) and $qq_2$ consists of xv) The amino acid sequence TGTKDASIDY-HEWQASLALSYRLNMFTPYIGVKWS (SEQ ID NO: 44) or xvi) A subsequence of the amino acid sequence in xv) said subsequence comprising 1-35 amino acid residues, starting with the N-terminal T in the amino acid sequence in xv).

The immuno-repeats can be heterologous, that is where the variable domain is derived from different serotypes or they can be homologous, that is where the variable domain is derived one serotype. The preferred number of repeats are 2, 3, 4, 5, 6, 7 or 8 repeats.

Furthermore the immuno-repeats in the polypeptides can be linearized, that is cysteine residues are replaced with serine.

The polypeptides comprising immuno-repeats can additionally comprise a moiety that facilitate export of the polypeptide whens produced recombinantly (e.g. signal peptides), a moiety that facilitate purification of the polypeptide (e.g. his-tags) and/or a moiety which enhance the immunogenicity (e.g. a T cell antigen). The T-cell target can be chosen from a Ct antigen such as CT043, CT004, CT414, CT681 or part hereof. Examples of such fusion proteins are indicated by SEQ ID NO 60-67.

A polypeptide according to the invention having the following functional abilities:

a) neutralize *C. trachomatis* serovar D in vitro with a 50% neutralization titer of $10^{-3}$ or less, when tested in an experimental set-up comprising the administering a heterologous immuno-repeats;

b) neutralize *C. trachomatis* serovar D in vivo in at least 50% of the mice at day 7 post infection when tested in a mouse model comprising administering a heterologous immuno-repeats c) broaden the immune response to multiple serovars of *C. trachomatis* in vitro when administering heterologous immuno-repeats.

The present invention also discloses nucleic acids encoding above described polypeptides.

The disclosed polypeptides or nucleic acids are used for the preparation of a pharmaceutical composition such as a vaccine. The vaccine can additionally comprise a pharmacologically acceptable carrier (virus like particles), excipient, adjuvant (e.g. DDA/TDB or alum) or immune modulator. The pharmaceutical composition can be used for prophylactic or therapeutic use against *Chlamydia* sp. Infections, including infections with *Chlamydia trachomatis* or *C. pneumoniae*.

A method for preventing, treating and/or reducing the incidence of *Chlamydia* sp. Infections, including infections with *Chlamydia trachomatis* or *C. pneumoniae*, by administering this pharmaceutical composition is also disclosed.

In the following the invention will be described in more detail and exemplified.

The preferred outer membrane protein is MOMP but may also include other surface exposed antigens from *Chlamydia* species that are targets for humoral responses.

The immuno-repeat from a surface exposed region can be from the same serotype (homologous immuno-repeats) or represent fragments that contain variable epitopes and are derived from different serotypes (heterologous immuno-repeat). In a preferred embodiment the immuno-repeats contain an extended fragment that contains both a variable and a conserved region known to be rich in T cell epitopes.

A preferred surface exposed region of an outer membrane protein is chosen from VD1, VD2, VD3 and VD4 from MOMP.

The amino acid sequences used for constructing the immuno-repeats described in the examples are chosen from table 1, 2 and 3.

The variable domain of VD4 of MOMP can be described as an amino acid sequences as defined as:

La1-Aa2-Aa1-Aa3-La2 wherein

Aa1 consists of the amino acid sequence TTLNPTIAG (SEQ ID NO: 76) (which is conserved for all serovars);

Aa2 is selected from the group consisting of: SATAIFDT (SEQ ID NO: 79) (from serovar D and E), LVTPVVDI (SEQ ID NO: 80) (from serovar F), LAKPVVDI (SEQ ID NO: 81) (from serovar G) and LAEAILDV (SEQ ID NO: 82) (from serovar Ia and J).

When Aa2 is the sequence from serovar D or E, then Aa3 is selected from the sequences set forth in AGDVKTGAE-GQLG (SEQ ID NO: 83) (from serovar D) and AGDVKA-SAEGQLG (SEQ ID NO: 84) (serovar E).

When Aa2 is the sequence from serovar F, then Aa3 is the sequence CGSVAGANTEGQIS (SEQ ID NO: 85) (from serovar F).

When Aa2 is the sequence from serovar G, then Aa3 is the sequence CGSVVAANSEGQIS (SEQ ID NO: 86) (from serovar G).

When Aa2 is the sequence from serovar Ia or J), then Aa3 is selected from KGTVVSSAENELA (SEQ ID NO: 87) (from serovar Ia) and KGTVVASGSENDLA (SEQ ID NO: 88) (from serovar J)

The variable domain VD4 of MOMP is depicted in FIG. 2. The immuno-repeats preferably additionally comprises extensions on either sides which are also depicted in FIG. 2.

The N-terminal side of a VD4 domain can be flanked or extended by one or more amino acids from the more conserved and T-cell epitope rich La1, where La1 is the part of VD4 of MOMP which is embedded in the membrane and has the amino acid sequence EWQASLAL-SYRLNMFTPYIGVKWSRASFDADTIRIAQPK (SEQ ID NO: 21) or an amino acid sequence having 80% sequence identity herewith.

The C-terminal side of a VD4 domain can correspondingly be flanked or extended by one or more amino acids from the more conserved and T-cell epitope rich La2, where La2 is the part of VD4 of MOMP which is embedded in the membrane on the C-terminal side and has the amino acid sequence DTMQIVSLQLNKMKSRKSCGIAVGTTIVDA (SEQ ID NO: 22) or an amino acid sequence having 80% sequence identity herewith.

A similar illustration (see FIG. 1) can describe immuno-repeats comprising the variable domain 1 (VD1) of MOMP with the variable domains (Aa2-Aa1-Aa3) of the various serovars are given by SEQ ID NO: 1-6 in table 1. The corresponding N-terminal and C-terminal extensions (La1 and La2) have the respective amino acid sequences SMRVGYYGDFVFDRVLKTDVNKEFQMG (SEQ ID NO: 77) (La1) and NPAYGRHMQDAEMFTNAACMAL-NIWD (SEQ ID NO: 78) (La2) which are given in table 2 by SEQ ID NO: 7-8.

Immuno-repeats comprising VD2 and VD3 can in a similar manner be deduced from FIG. 1 and table 1.

Hence above example Lal-Aa2-Aa1-Aa3-La2 defines one of the immune-repeat units. If additionally e.g. VD1 is added to a VD4 unit, this can be described as adding one more sequence to make up a larger immune-repeat unit. Hence the polypeptide of the invention comprises 2, 3, 4, 5, 6, 7 or 8 repeats of immune-repeat units.

Definitions

Outer Membrane Proteins

The outer membrane of *Chlamydia* sp. can be isolated by treating intact, purified elementary bodies with detergent such as 2% Sarkosyl followed by ultracentrigation (100,000 g for one hour) which will lead to a supernatant with cytosolic components and a pellet containing the outer membrane as previously described 70. Outer membrane proteins can then be identified by standard protein tech-niques, e.g. by mass spectrometry after SDS-PAGE.

Surface Exposed Fragments or Regions

Bacterial surface or membrane proteins comprises trans membrane proteins, secretory and lipoproteins, and anchor-less surface proteins. Surface exposed regions on intact bacteria are accessible to antibodies. Methods to identify surface exposed regions of proteins (the 'surfaceome' com-prise e.g. biotinylation of the membrane proteins in intact bacteria, followed by isolation of the biotin-labelled fraction using streptavidin. The isolated proteins can then be iden-tified by mass spectrometry. Another approach is to treat intact bacteria with a protease, e.g. trypsin ('shaving') to cleave surface exposed peptides, followed by collection of the released peptides for identification by mass spectrom-etry.

Variants

Variants of outer membrane proteins provided herein describes proteins encoded by the same gene from different serotypes of *Chlamydia* sp. A variant protein shares signifi-cant homology with a reference polypeptide.

An Isoform of Protein

In the context of the present application an "isoform" of protein is understood as any of several different forms of the same protein e.g. a protein that has the same function but which is encoded by a different gene and may have small differences in its sequence or arises from either single nucleotide polymorphisms, differential splicing of mR NA, or post-translational modifications. Different serotypes of bacteria may have different isoforms of certain proteins.

*Chlamydia* Species

By the term "*Chlamydia* species" is understood a bacte-rium capable of causing the *Chlamydia* infection in an animal or in a human being. Examples are *C. trachomatis, C. pneumoniae* and *C. muridarum*. Also in animals, several infections with *Chlamydia* sp. are known, e.g. *Chlamydia suis* infecting pigs, and *Chlamydiaphila abortus* which causes abortion in small ruminants (sheep and goats).

12

Serovariants, Serovars or Serotypes

Based on the reactivity of specific mono clonal antibodies against variable regions and detailed sequence analysis of the MOMP vari-able regions Ct can be divided into 15 different serovariants and of these serovariants A, B, Ba and C causes Trachoma, D-K causes sexually transmitted disease (STD), L1-L3 causes Lymphogranuloma venerum, and MoPn (*C. muri-darum*) infects mice. Serovariants are sometimes mentioned as serovars or serotypes with the same meaning.

Immuno-Repeats

By immuno-repeats is understood: repetitive units of one or more amino acid sequences comprising an immunogenic portion or fragment of an antigen. The units that are repeated can be described as one or more VD regions, that optionally can be extended as described above, that are repeated e.g. 4 examples with three repeats VD4-VD4-VD4, VD4-VD1-VD4-VD1-VD4-VD1, $VD4_D$-$VD4_D$-$VD4_D$, $VD4_D$-$VD4_F$-$VD4_G$, $VD4_D$-$VD3_E$-$VD4_D$-$VD3_E$. $VD4_D$-$VD3_E$.

Homologous Immuno-Repeat

Figure 4:
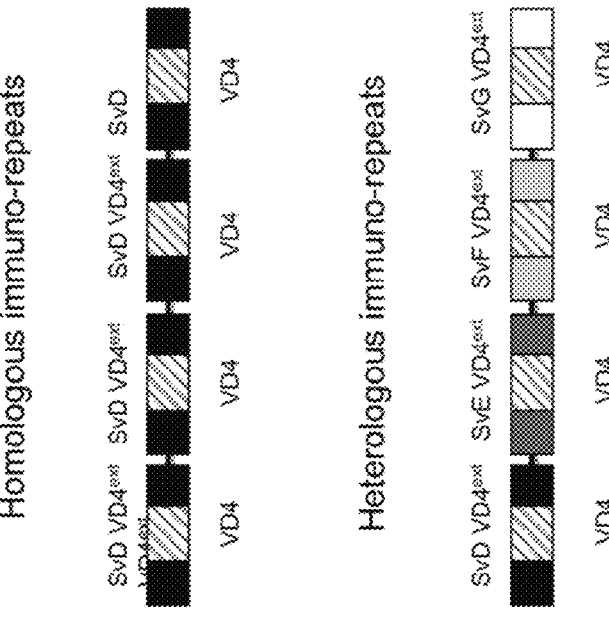
FIG. 4. Illustration of the design of homologous and heterologous immuno-repeats. The immuno-repeats are fusion proteins of e.g. four VD4$^{ext}$ regions, either from the same serovar, homologous immuno-repeats, or from different serovars, heterologous immuno-repeats. The variable VD4 region within each VD4$^{ext}$ region is illustrated as hatched.

Repetitive units of one or more amino acid sequences comprising an immunogenic portion or fragment of an antigen from one serovariant only (FIG. 4)

Heterologous Immuno-Repeat

Repetitive units of one or more amino acid sequences comprising an immunogenic portion or fragment encoding the same antigen derived from different serovariants (FIG. 4).

Heterologous Challenge

Refers to the situation where the protein used for vacci-nation is derived from a different bacterial serovariant than the serovariant used for challenge.

Homologous Challenge

Refers to the situation where the protein used for vacci-nation is derived from the same bacterial serovariant as the serovariant used for challenge.

MOMP

The Major Outer Membrane Protein (MOMP) of Ct, is expressed during all phases of the developmental life cycle of Ct and constitutes approximately 60% of the total protein content of the chlamydia outer membrane. MOMP can be divided into conserved domains interrupted by four highly variable domains (VD1-4 or VS1-4)[59] (FIG. 1)

VD1

Figure 3:
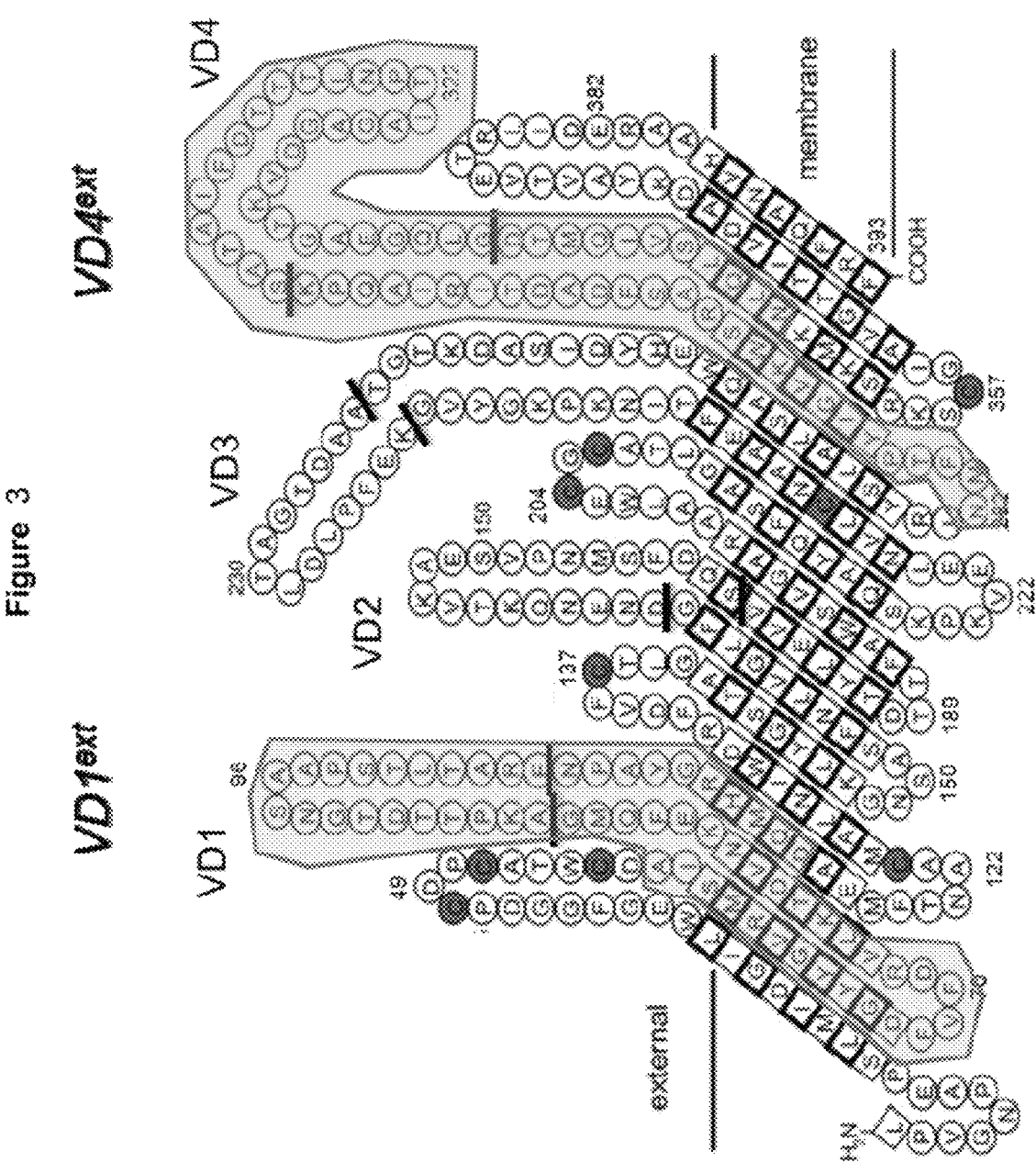
FIG. 3. Model of MOMP (Serovar D, strain: D/B-120) membrane topology adapted from Findlay et al. The VD1ext and VD4ext described in this invention are shown as shaded in the figure. Amino acid sequence shown is SEQ ID NO: 68.

Variable domain 1 (VD1) of MOMP as defined by Baehr et al (1988)[36] which corresponds to amino acids 91-105 and make up a highly variable region in MOMP from Ct (Seq no 1-6 VD1 from S vD, E, F, G, Ia and J respectively). The extended VD1 region (VD1$^{ext}$) corresponds to amino acids 57-115 and make-up said highly variable region flanked by highly conserved regions in MOMP from Ct (Seq no 9-14 VD1$^{ext}$ from S vD, E, F, G, Ia and J respectively) (FIG. 3).

VD4

Variable domain 4 of MOMP as defined by Baehr et al (1988)[36] which corresponds to amino acids 309-338 and make up a highly variable region in MOMP from Ct (Seq no 15-20 VD4 from S vD, E, F, G, Ia and J respectively). The extended VD4 region (VD4$^{ext}$) corresponds to amino acids 282-349 and make-up said highly variable region flanked by highly conserved regions in MOMP from Ct (Seq no 23-28 VD4$^{ext}$ from S vD, E F, G, Ia and J respectively).

Linearized

The word "linearized" in the present invention refers to an amino acid chain of any length, including a full-length protein, oligopeptides, short peptides and fragments thereof, wherein the amino acid cysteine has been substituted with serine in order to hinder the cysteine residues to form disulfide bonds.

Neutralizing Epitope

Neutralizing epitope as used herein is intended an amino acid sequence that defines an antigenic determinant which is bound by an antibody and, in the context of infection, reduces infectivity of a Chlamydial load, e.g. by blocking of the bacterial interaction with host cells, which is important in establishing bacterial infection and disease, facilitating bacterial clearance.

Neutralization

Neutralization is to encompass any biological activity of the bacteria, including reduction in the efficiency or ability of the bacterium to establish infection or cause disease or disease symptoms, inhibition of chlamydial E B formation.

Neutralizing Antibodies

Antibodies which bind a neutralizing epitope as described above.

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

IFN-$\gamma$

By the term "IFN-$\gamma$" is understood interferon-gamma. The measurement of IFN-$\gamma$ is used as an indication of an immunological T-cell response.

Comprise

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Immunogenic Portion or Fragment

In a preferred embodiment of the invention, the polypeptide comprises an immunogenic portion or fragment of the polypeptide, such as an epitope for a B-cell or T-cell.

The immunogenic portion or fragment of a polypeptide is a part of the polypeptide, which elicits an immune response in an animal or a human being, and/or in a biological sample determined by any of the biological assays described herein. The immunogenic portion or fragment of a polypeptide may be a T-cell epitope or a B-cell epitope. Immunogenic portions or fragments can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence[71].

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFN-$\gamma$ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFN-$\gamma$ assay as described herein) and some of these will give a positive response (and thereby be immunogenic) as evidence for the presence of a T cell epitope in the peptide. For the detection of MHC class I epitopes it is possible to predict peptides that will bind[72] and hereafter produce these peptides synthetic and test them in relevant biological assays e.g. the IFN-$\gamma$ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al[73].

Immunogenic

An immunogenic polypeptide is defined as a polypeptide that induces an immune response in a biological sample or an individual currently or previously infected with a chlamydia.

Fusion Proteins

By a fusion protein is understood two or more polypeptides linked together covalently. The fusion proteins can be produced with superior characteristics of the polypeptide. For instance, fusion partners that facilitate export of the fusion protein when produced recombinantly (e.g. signal peptides), fusion partners that facilitate purification of the fusion protein (e.g. his-tags), and fusion partners which enhance the immunogenicity of the fusion protein are all interesting possibilities. The fusion partner can, in order to enhance immunogenicity, be another polypeptide derived from *C. trachomatis*, such as a polypeptide, a polypeptide fragment or at least one T-cell epitope or B cell epitope.

Pharmaceutical Composition

A pharmaceutical composition is defined as any vaccine (both therapeutic and prophylactic) or any diagnostic reagent.

Vaccine, Protein

Another part of the invention pertains to a vaccine composition comprising a fusion protein or a nucleic acid encoding said fusion protein according to the invention. In order to ensure op-timum performance of such a vaccine composition it is preferred that it comprises an immunologically and pharmaceutically acceptable carrier, vehicle or adjuvant.

An effective vaccine, wherein a fusion protein of the invention is recognized by a mammal including a human being, will decrease bacterial load in target organs, prolong survival times and/or diminish weight loss after challenge with virulent chlamydial bacteria, compared to non-vaccinated individuals.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyl-dioctadecylammonium bromide (DDA), Quil A, poly I:C, aluminium hydroxide, Freund's incomplete adjuvant, IF N$\gamma$, IL-2, IL-12, monophosphoryl lipid A (MPL), Trehalose Dimycolate (TDM), Trehalose Dibephenate (TDB) and muramyl dipeptide (MDP), Monomycolyi glycerol (MMG) or a combination hereof. A preferred combination is a cationic liposome such as DDA combined with TDB and/or poly I:C.

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Therapeutic Vaccine.

The invention also relates to the use of a polypeptide or nucleic acid of the invention for use as therapeutic vaccines as have been described in the literature exemplified by D.

Lowry (Lowry et al 1999). Antigens with therapeutic properties may be identified based on their ability to diminish the severity of Ct infection in experimental animals or prevent reactivation of previous infection, when administered as a vaccine. The composition used for therapeutic vaccines can be prepared as described above for vaccines.

The present invention describes novel highly immunogenic vaccine antigens with broad antibody based neutralizing capacity that protects against different serovariants of *Chlamydia trachomatis*. We demonstrate that repetitive units of defined fragments from the MOMP antigen provide highly immunogenic molecules which we refer to as immuno-repeats. Vaccination with homologous immuno-repeats containing VD4 extended fragments (covers the VD4 variable domain of MOMP and the adjacent conserved flanking regions) in different adjuvants provides very high antibody titers and we demonstrate that these constructs are much more efficient than immunizing with single units of the VD4 extended fragment. The increased effect can be observed both as markedly increased titer, increased antibody targeting of the surface of the bacteria, increased neutralizing capacity, increased and broadened T cell response and increased protection against a challenge with the homologous strain. We furthermore demonstrate that the immuno-repeat technology can be utilized also to improve the protection against and neutralization of other serovariants by constructing heterologous immuno-repeats based on VD4 extended fragments from different serovariants such as serovar D, E, F and G (FIG. 3).

TABLE 1

Description of sequences used in constructing immuno-repeats

| SEQ ID NO | Variable domaines | Description |
|---|---|---|
| 1 | VD1_SvD | Serovar D variable domaine 1 of MOMP |
| 2 | VD1_SvE | Serovar E variable domaine 1 of MOMP |
| 3 | VD1_SvF | Serovar F variable domaine 1 of MOMP |
| 4 | VD1_SvG | Serovar G variable domaine 1 of MOMP |
| 5 | VD1_SvIa | Serovar Ia variable domaine 1 of MOMP |
| 6 | VD1_SvJ | Serovar J variable domaine 1 of MOMP |
| 7 | VD1 N-terminal | VD1 N-terminal extension |
| 8 | VD1 C-terminal | VD1 C-terminal extension |
| 9 | VD1ext_SvD | Serovar D extended VD1 of MOMP |
| 10 | VD1ext_SvE | Serovar E extended VD1 of MOMP |
| 11 | VD1ext_SvF | Serovar F extended VD1 of MOMP |
| 12 | VD1ext_SvG | Serovar G extended VD1 of MOMP |
| 13 | VD1ext_SvIa | Serovar Ia extended VD1 of MOMP |
| 14 | VD1ext_SvJ | Serovar J extended VD1 of MOMP |
| 15 | VD4_SvD | Serovar D variable domaine 4 of MOMP |
| 16 | VD4_SvE | Serovar E variable domaine 4 of MOMP |
| 17 | VD4_SvF | Serovar F variable domaine 4 of MOMP |
| 18 | VD4_SvG | Serovar G variable domaine 4 of MOMP |
| 19 | VD4_SvIa | Serovar Ia variable domaine 4 of MOMP |
| 20 | VD4_SvJ | Serovar J variable domaine 4 of MOMP |
| 21 | VD4 N-terminal | VD4 N-terminal extension |
| 22 | VD4 C-terminal | VD4 C-terminal extension |
| 23 | VD4ext_SvD | Serovar D extended VD4 of MOMP |
| 24 | VD4ext_SvE | Serovar E extended VD4 of MOMP |
| 25 | VD4ext_SvF | Serovar F extended VD4 of MOMP |
| 26 | VD4ext_SvG | Serovar G extended VD4 of MOMP |
| 27 | VD4ext_SvIa | Serovar Ia extended VD4 of MOMP |
| 28 | VD4ext_SvJ | Serovar J extended VD4 of MOMP |
| 29 | VD2_SvD | Serovar D variable domaine 2 of MOMP |
| 30 | VD2_SvE | Serovar E variable domaine 2 of MOMP |
| 31 | VD2_SvF | Serovar F variable domaine 2 of MOMP |
| 32 | VD2_SvG | Serovar G variable domaine 2 of MOMP |
| 33 | VD2_SvIa | Serovar Ia variable domaine 2 of MOMP |
| 34 | VD2_SvJ | Serovar J variable domaine 2 of MOMP |
| 35 | VD2 N-terminal | VD2 N-terminal extension |
| 36 | VD2 C-terminal | VD2 C-terminal extension |
| 37 | VD3_SvD | Serovar D variable domaine 3 of MOMP |

TABLE 1-continued

Description of sequences used in constructing immuno-repeats

| SEQ ID NO | Variable domaines | Description |
|---|---|---|
| 38 | VD3_SvE | Serovar E variable domaine 3 of MOMP |
| 39 | VD3_SvF | Serovar F variable domaine 3 of MOMP |
| 40 | VD3_SvG | Serovar G variable domaine 3 of MOMP |
| 41 | VD3_SvIa | Serovar Ia variable domaine 3 of MOMP |
| 42 | VD3_SvJ | Serovar J variable domaine 3 of MOMP |
| 43 | VD3 N-terminal | VD3 N-terminal extension |
| 44 | VD3 C-terminal | VD3 C-terminal extension |

Heterologous immuno-repeats were highly immunogenic but in addition increased the breadth of the antibody responses which was associated with a broader fine specificity of the antibody response (measured by peptide scans) that targets a more diverse repertoire of linear epitopes within the VD4 region than the homologous immuno-repeats. We also demonstrate that highly immunogenic heterologous immuno-repeats can be based on even larger fragments that incorporate fusions of VD1 and VD4 extended fragments and we confirm that in animal models protection promoted by these heterologous immuno-repeats are mediated predominantly by antibodies. As there is a generally recognized need for a strong CMI component (e.g. a T-cell epitope) in an efficient protective immune response against Ct, we have also demonstrated that by fully extending the VD4 region N-terminally to include a T cell rich region, we can generate immune-repeats that combine the ability to generate high tittered neutralizing antibodies with a strong T cell response clearing residual infection in one construct. We have also demonstrated that immune-repeats can be fused to or mixed with T-cell antigens with vaccine potential and that this combination provide both an early antibody mediated protection against Ct as well as an efficient CMI mediated clearance of residual organisms.

MOMP is an important protective antigen with a generally recognized potential in Ct vaccines. The MOMP antigen is however a very complicated antigen to target by vaccines because it has a complex structure with numerous internal disulfide bonds and where important neutralizing epitopes have been exceedingly difficult to expose in recombinant molecules. Adding to this, the MOMP antigen is highly variable and is the basis for the majority of the serovariance found in different strains causing human disease. Any vaccine based on intact MOMP would therefore have to incorporate a number of different versions of the molecule (at least 4-5) to cover the major strains giving rise to disease in humans. As described above the MOMP antigen contains 4 variable regions (VD1-4) of which in particular the VD1 and VD4 contain important neutralizing epitopes but vaccines based on fragments representing these regions have so far failed to induce sufficiently high titers of functional antibodies to have any in vivo effect in animal challenge studies[51][74].

The immuno-repeat technology of the present invention solves this problem: By repeating the important variable VD1 and/or VD4 regions flanked by conserved sequences from the MOMP antigen we have obtained immunogens that promote extraordinary levels of functional antibodies. Surprisingly we also demonstrate that the improved immunogenicity can even be achieved in heterologous immuno-repeat constructs that employs variable regions from different serovars interspaced between conserved fragments and that this strategy produces a broadly neutralizing antibody response that protect against different serovariants.

Furthermore, do the immuno-repeat technology provide a large number of relevant T cell epitopes that promote T cells with direct effector function as well as the ability to promote accelerated recall responses to the adjacent B cell epitopes.

Our invention therefore represents a breakthrough in developing efficient Ct vaccines with a broad response and the ability to neutralize different serovars.

It is well known that antigens with a large number of repeats and organized structure are optimal for the activation of the B-cell receptor (BCR), leading to an increased humoral response and a decreased dependence on T-cell help. This was originally reported with natural polysaccharide based antigens from various pathogens (Pneumococcal polysaccharide and *Salmonella* polymerized flagellin) where the repetitive nature of the antigen is assumed to trigger several BCR simultaneously thereby lowering the overall activation threshold which triggers antibody production from plasma B-cells without the need for prior T-cell help. Such antigens are referred to as type 2 T-cell independent B-cell antigens and in artificial systems have been shown to depend on a large number of repeats (typically a minimum of 12-16[75]), that constitute the minimal epitope and are closely located. This is clearly different from our repeat technology where large fragments (69 amino acids, Mw>7 kDa) are repeated and these fragments contain both B-cell and T-cell epitopes[76].

In contrast to previous observations[75], we observe an increase by just 4 repeats which is not further improved by 8 repeats. Importantly, the repetition of a conserved sequence with hypervariable domains inserted, amplify responses not only to the repeated conserved element but importantly to the variable inserts. The molecular mechanism behind this surprising amplification is not completely clear but it most likely relates to the fact that many of the important epitopes are located in the overlap between variable and conserved regions which therefore may allow simultaneous triggering of different BCR's that all share some recognition of the conserved part of the epitope. Although the mechanism is not completely clear the practical consequence is that the heterologous immune-repeat technology allows the synthesis of a multivalent immunogens that promote the generation of a diverse antibody response that targets different serovariants.

Our immuno-repeat constructs provide antigens of an extraordinary immunogenicity compared to previous attempts to use the variable domains from Ct MOMP. All previous vaccines based on VDs of MOMP did, in spite of generating antibodies with some functional capabilities, fail to generate titres that translated into in vivo protection against genital chlamydial challenge[51, 65 64]. In particular the heterologous immuno-repeat strategy solves a very fundamental problem seen for many pathogens and that is how to promote diverse antibody responses to diverse and variable antigens.

TABLE 2

| | Immuno-repeats | |
|---|---|---|
| SEQ ID NO | Polypeptide names | Description |
| 45 | CTH87 (CT681_VD1ext_VD4ext_SvD) | Fusion of VD1-VD4 of serovar D |
| 46 | CTH88 (CT681_lin_VD1ext_VD4ext_SvD_E_F) | Heterologous immune repeat of VD1-VD4 |
| 47 | CTH88ext = CTH69 (CT681_lin_VD1ext_VD4ext_SvD_E_F_ext) | Same as SEQ ID NO 46 with longer flanking region. |
| 48 | CTH72 (CT681_lin_VD1ext_VD4ext_SvD_E_F_G_Ia_J_ext) | Same as seq id no 47 additionally with VD1ext and VD4ext from SvG, SvIa and SvJ |
| 49 | CTH89 (CT681_lin_VD4ext_SvD_E_F) | Heterologous immune repeat of VD4 |
| 50 | CTH181 (CT681_VD4ext_SvE) | Same as SEQ ID NO 24 |
| 51 | CTH182 (CT681_lin_VD4ext_F) | Same as SEQ ID NO 25 linearized |
| 52 | CTH183 (CT681_VD4ext_F) | Same as SEQ ID NO 25 |
| 53 | CTH518 (CT681_Lin_VD4ext_D_E_F_G) | Heterologous immune repeat of VD4 |
| 54 | CTH518ext = CTH70 (CT681_lin_VD4ext_SvD_E_F_G_ext) | Same as SEQ ID NO 53 with longer flanking regions |
| 55 | CTH71 (CT681_lin_VD4ext_SvD_E_F_G_Ia_J_ext) | Same as seq id no 54 additionally with VD1ext and VD4ext from SvIa and SvJ |
| 56 | CTH524 (CT681_lin_4_VD4ext_F) | Same as SEQ ID NO 59 linearized |
| 57 | CTH526 (CT681_8_VD4ext_SvE) | Homologous immune repeat of VD4 (8x) |
| 58 | CTH527 (CT681_4_VD4ext_SvE) | Homologous immune repeat of VD4 (4x) |
| 59 | CTH529 (CT681_4_VD4ext_F) | Homologous immune repeat of VD4 (4x) |

TABLE 3

Examples of immuno-repeats fused with T-cell antigens

| SEQ ID NO | Fusions of immuno repeats with T-cell antigens (all his-tagged) |
|---|---|
| 60 | CTH91 (CT043-CT414p-CT681_lin_VD1ext_VD4ext_SvD_E_F) |
| 61 | CTH93 (CT043_CT414p_CT681_Lin_56-281_VD4ext_D) |
| 62 | CTH520 (CT681_56-281_VD4ext_D) |
| 63 | CTH521 (CT681_Lin_56-281_VD4ext_D) |
| 64 | CTH522 (CT681_lin_56-281_VD4ext_D_E_F_G) |
| 65 | CTH531 (CT414_CT043_CT043_681_lin_56-281_VD4ext_SvD_E_F_G) |
| 66 | CTH533 (CT043_CT043_CT681_lin_VD4ext_SvD_E_F_G) |
| 67 | CTH534 (CT043_CT043_CT004_CT681_lin_VD4ext_SvD_E_F_G) |
| 68 | CT681_SvD |
| 69 | CTH285 (VD4_lin_SvD, E, F, G) |
| 70 | CTH286 (VD4 classic + 7_lin_SvD, E, F, G) |

TABLE 4

Overlapping peptides of VD4 from serovar E

| VD4 serovar E peptides (20mers) | Amino acid sequence | SEQ ID NO |
|---|---|---|
| CT681_25_SvE | DASIDYHEWQASLALSYRLN | 89 |
| CT681_26_SvE | ASLALSYRLNMFTPYIGVKW | 90 |
| CT681_27_SvE | MFTPYIGVKWSRASFDADTI | 91 |
| CT681_28_SvE | SRASFDADTIRIAQPKSATA | 92 |
| CT681_29_SvE | RIAQPKSATAIFDTTTLNPT | 93 |
| CT681_30_SvE | IFDTTTLNPTIAGAGDVKAS | 94 |
| CT681_31_SvE | IAGAGDVKASAEGQLGDTMQ | 95 |
| CT681_32_SvE | AEGQLGDTMQIVSLQLNKMK | 96 |

TABLE 5

Overlapping peptides of VD4 from serovar F

| Serovar F peptides (20mers) | Amino acid sequence | SEQ ID NO |
|---|---|---|
| CT681_25_SvF | DASIDYHEWQASLSLSYRLN | 97 |
| CT681_26_SvF | ASLSLSYRLNMFTPYIGVKW | 98 |
| CT681_27_SvF | MFTPYIGVKWSRASFDSDTI | 99 |
| CT681_28_SvF | SRASFDSDTIRIAQPRLVTP | 100 |
| CT681_29_SvF | RIAQPRLVTPVVDITTLNPT | 101 |
| CT681_30_SvF | VVDITTLNPTIAGCGSVAGA | 102 |
| CT681_31_SvF | IAGCGSVAGANTEGQISDTMQ | 103 |
| CT681_32_SvF | TEGQISDTMQIVSLQLNKMK | 104 |

TABLE 6

Overlapping peptides of VD4 from serovar D

| VD4 serovar D peptides (9mers) | Amino acid sequence | SEQ ID NO |
|---|---|---|
| VD4_P1_SvD | SRASFDADT | 105 |
| VD4_P2_SvD | RASFDADTI | 106 |
| VD4_P3_SvD | ASFDADTIR | 107 |
| VD4_P4_SvD | SFDADTIRI | 108 |
| VD4_P5_SvD | FDADTIRIA | 109 |
| VD4_P6_SvD | DADTIRIAQ | 110 |
| VD4_P7_SvD | ADTIRIAQP | 111 |
| VD4_P8_SvD | DTIRIAQPK | 112 |
| VD4_P9_SvD | TIRIAQPKS | 113 |
| VD4_P10_SvD | IRIAQPKSA | 114 |
| VD4_P11_SvD | RIAQPKSAT | 115 |
| VD4_P12_SvD | IAQPKSATA | 116 |
| VD4_P13_SvD | AQPKSATAI | 117 |
| VD4_P14_SvD | QPKSATAIF | 118 |
| VD4_P15_SvD | PKSATAIFD | 119 |
| VD4_P16_SvD | KSATAIFDT | 120 |
| VD4_P17_SvD | SATAIFDTT | 121 |
| VD4_P18_SvD | ATAIFDTTT | 122 |
| VD4_P19_SvD | TAIFDTTTL | 123 |
| VD4_P20_SvD | AIFDTTTLN | 124 |
| VD4_P21_SvD | IFDTTTLNP | 125 |
| VD4_P22_SvD | FDTTTLNPT | 126 |
| VD4_P23_SvD | DTTTLNPTI | 127 |
| VD4_P24_SvD | TTTLNPTIA | 128 |
| VD4_P25_SvD | TTLNPTIAG | 76 |
| VD4_P26_SvD | TLNPTIAGA | 129 |
| VD4_P27_SvD | LNPTIAGAG | 130 |
| VD4_P28_SvD | NPTIAGAGD | 131 |
| VD4_P29_SvD | PTIAGAGDV | 132 |
| VD4_P30_SvD | TIAGAGDVK | 133 |
| VD4_P31_SvD | IAGAGDVKT | 134 |
| VD4_P32_SvD | AGAGDVKTG | 135 |
| VD4_P33_SvD | GAGDVKTGA | 136 |
| VD4_P34_SvD | AGDVKTGAE | 137 |
| VD4_P35_SvD | GDVKTGAEG | 138 |
| VD4_P36_SvD | DVKTGAEGQ | 139 |
| VD4_P37_SvD | VKTGAEGQL | 140 |
| VD4_P38_SvD | KTGAEGQLG | 141 |

TABLE 6-continued

Overlapping peptides of VD4 from serovar D

| VD4 serovar D peptides (9mers) | Amino acid sequence | SEQ ID NO |
|---|---|---|
| VD4_P39_SvD | TGAEGQLGD | 142 |
| VD4_P40_SvD | GAEGQLGDT | 143 |
| VD4_P41_SvD | AEGQLGDTM | 144 |
| VD4_P42_SvD | EGQLGDTMQ | 145 |
| VD4_P43_SvD | GQLGDTMQI | 146 |
| VD4_P44_SvD | QLGDTMQIV | 147 |
| VD4_P45_SvD | LGDTMQIVS | 148 |

TABLE 7

Overlapping peptides of VD4 from serovar F

| VD4 serovar F peptides (9mers) | Amino acid sequence | SEQ ID NO |
|---|---|---|
| VD4_P1_SvF | SRASFDSDT | 149 |
| VD4_P2_SvF | RASFDSDTI | 150 |
| VD4_P3_SvF | ASFDSDTIR | 151 |
| VD4_P4_SvF | SFDSDTIRI | 152 |
| VD4_P5_SvF | FDSDTIRIA | 153 |
| VD4_P6_SvF | DSDTIRIAQ | 154 |
| VD4_P7_SvF | SDTIRIAQP | 155 |
| VD4_P8_SvF | DTIRIAQPR | 156 |
| VD4_P9_SvF | TIRIAQPRL | 157 |
| VD4_P10_SvF | IRIAQPRLV | 158 |
| VD4_P11_SvF | RIAQPRLVT | 159 |
| VD4_P12_SvF | IAQPRLVTP | 160 |
| VD4_P13_SvF | AQPRLVTPV | 161 |
| VD4_P14_SvF | QPRLVTPVV | 162 |
| VD4_P15_SvF | PRLVTPVVD | 163 |
| VD4_P16_SvF | RLVTPVVDI | 164 |
| VD4_P17_SvF | LVTPVVDIT | 165 |
| VD4_P18_SvF | VTPVVDITT | 166 |
| VD4_P19_SvF | TPVVDITTL | 167 |
| VD4_P20_SvF | PVVDITTLN | 168 |
| VD4_P21_SvF | VVDITTLNP | 169 |
| VD4_P22_SvF | VDITTLNPT | 170 |
| VD4_P23_SvF | DITTLNPTI | 171 |
| VD4_P24_SvF | ITTLNPTIA | 172 |
| VD4_P25_SvF | TTLNPTIAG | 76 |

TABLE 7-continued

Overlapping peptides of VD4 from serovar F

| VD4 serovar F peptides (9mers) | Amino acid sequence | SEQ ID NO |
|---|---|---|
| VD4_P26_SvF | TLNPTIAGC | 173 |
| VD4_P27_SvF | LNPTIAGCG | 174 |
| VD4_P28_SvF | NPTIAGCGS | 175 |
| VD4_P29_SvF | PTIAGCGSV | 176 |
| VD4_P30_SvF | TIAGCGSVA | 177 |
| VD4_P31_SvF | IAGCGSVAG | 178 |
| VD4_P32_SvF | AGCGSVAGA | 179 |
| VD4_P33_SvF | GCGSVAGAN | 180 |
| VD4_P34_SvF | CGSVAGANT | 181 |
| VD4_P35_SvF | GSVAGANTE | 182 |
| VD4_P36_SvF | SVAGANTEG | 183 |
| VD4_P37_SvF | VAGANTEGQ | 184 |
| VD4_P38_SvF | AGANTEGQI | 185 |
| VD4_P39_SvF | GANTEGQIS | 186 |
| VD4_P40_SvF | ANTEGQISD | 187 |
| VD4_P41_SvF | NTEGQISDT | 188 |
| VD4_P42_SvF | TEGQISDTM | 189 |
| VD4_P43_SvF | EGQISDTMQ | 190 |
| VD4_P44_SvF | GQISDTMQI | 191 |
| VD4_P45_SvF | QISDTMQIV | 192 |
| VD4_P46_SvF | ISDTMQIVS | 193 |

TABLE 8

CT681 amino acid sequences

| SEQ ID NO | Amino acid sequences of MOMP (CT681) from different serovars |
|---|---|
| 68 | CT681_SvD |
| 71 | CT681_SvE |
| 72 | CT681_SvF |
| 73 | CT681_SvG |
| 74 | CT681_SvIa |
| 75 | CT681_SvJ |

The nucleic acid of the invention, that is nucleic acid encoding above mentioned fusion proteins, may be used for effecting in vivo expression of immunogenic polypeptides, i.e. the nucleic acid may be used in so-called DNA vaccines as reviewed in Ulmer et al 1993, which is included by reference.

In the construction and preparation of plasmid DNA encoding a fusion polypeptide to be used defined for DNA vaccination a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, CA, USA) including an endotoxin removal step. It is essential that plasmid DNA used for DNA vaccination is endotoxin free.

Hence, the invention also relates to a vaccine comprising a nucleic acid according to the invention, the vaccine effecting in vivo expression of the immunogenic polypeptide by an animal, including a human being, to whom the vaccine has been administered, the amount of expressed polypeptide being effective to confer substantially increased resistance to infections caused by virulent bacteria in an animal, including a human being.

The efficacy of such a DNA vaccine can possibly be enhanced by administering the gene encoding the expression product together with a DNA fragment encoding a polypeptide which has the capability of modulating an immune response.

One possibility for effectively activating a cellular immune response can be achieved by expressing the relevant immunogenic polypeptide in a non-pathogenic microorganism or virus. Well-known examples of such microorganisms are *Mycobacterium bovis* BCG, *Salmonella* and Pseudomona and examples of viruses are Vaccinia Virus and Adenovirus.

Therefore, another important aspect of the present invention is an improvement of the live BCG vaccine presently available, wherein one or more copies of a DNA sequence encoding one or more fusion polypeptides as defined above has been incorporated into the genome of the micro-organism in a manner allowing the micro-organism to express and secrete the fusion polypeptide. The incorporation of more than one copy of a nucleic acid sequence of the invention is contemplated to enhance the immune response.

Another possibility is to integrate the DNA encoding the fusion polypeptide according to the invention in an attenuated virus such as the Vaccinia virus or Adenovirus (Rolph et al 1997). The recombinant vaccinia virus is able to enter within the cytoplasma or nucleus of the infected host cell and the fusion polypeptide of interest can therefore induce an immune response, which is envisioned to induce protection against TB.

Although DNA vaccines were developed more than 16 years ago, clinical trials preceding stage I and II in humans are rare. Two veterinary DNA vaccines however, have been licensed; one for West Nile Virus (in horse) and a second for Infectious Hematopoetic Necrosis virus in Salmon. This demonstrates that DNA vaccines can have good protective effects and that new DNA vaccines are not limited by the size of the animal or species. The great success with DNA vaccines observed for the murine model for first generation DNA vaccines did not translate well to humans, nonetheless; researchers have recently demonstrated protective antibodies levels by a single dose of gene gun administrated HA DNA vaccine to humans.

"Nucleic acid immunization" or the commonly preferred name "DNA vaccines" are the inoculation of antigen encoding DNA or RNA as expression cassettes or expression vectors or incorporated into viral vectors with the purpose of inducing immunity to the gene product. Thus, in our definition of DNA vaccines we include all kinds of delivery systems for the antigen encoding DNA or RNA. The vaccine gene can be in form of circular plasmid or a linear expression cassette with just the key features necessary for expression (promotor, the vaccine gene and polyadenylation signal). Delivery systems may most often be naked DNA in buffer with or without adjuvant, DNA coupled to nanoparticles and/or formulated into adjuvant containing compounds or inserted into live viral or bacterial vectors such as Adenovirus, adeno associated virus, alphavirus, poxviruses, herpes virus etc. DNA vaccines hold great promise since they evoke both humoral and cell-mediated immunity, without the same dangers associated with live virus vaccines. In contrast to live attenuated virus vaccines DNA vaccines may be delivered to same or different tissue or cells than the live virus that has to bind to specific receptors. The production of antigens in their native forms improves the presentation of the antigens to the host immune system. Unlike live attenuated vaccines, DNA vaccines are not infectious and cannot revert to virulence.

DNA vaccines offer many advantages over conventional vaccines. It can be produced in high amounts in short time, abolishing the need for propagation in eggs, it is cost-effective, reproducible and the final product does not require cold storage conditions, because DNA is stable and resistant to the extremes of temperature. All currently licensed inactivated vaccines are efficient at inducing humoral antibody responses but only live attenuated virus vaccines efficiently induce a cytotoxic cellular response as well. DNA vaccines also have this ability and the induced response therefore may better mimic the natural response to viral infection than inactivated vaccines in respect to specificity and antibodies isotypes.

DNA vaccines induce an immune response which is comparable to the response acquired by natural virus infection by activating both humoral and cell-mediated immunity. The broad response to DNA vaccines is a result of the encoded genes being expressed by the transfected host cell, inducing both a Th1 and Th2 immune responses. The production of antigens in their native form improves the presentation of the antigens to the host immune system.

The two most common types of DNA vaccine administration are saline injection of naked DNA and gene gun DNA inoculations (DNA coated on solid gold beads administrated with helium pressure). Saline intra muscular injections of DNA preferentially generates a Th1 IgG2a response while gene gun delivery tends to initiate a more Th2 IgG1 response. Intramuscular injected plasmids are at risk of being degraded by extracellular deoxyribonucleases, however, the responses induced are often more long-lived than those induced by the gene gun method. Vaccination by gene gun delivery of DNA, to the epidermis, has proven to be the most effective method of immunization, probably because the skin contains all the necessary cells types, including professional antigen presenting cells (APC), for eliciting both humoral and cytotoxic cellular immune responses (Langerhans and dendritic cells). Complete protection from a lethal dose of influenza virus has been obtained with as little as 1 µg DNA in mice. The standard DNA vaccine vector consists of the gene of interest cloned into a bacterial plasmid engineered for optimal expression in eukaryotic cells. Essential features include; an origin of replication allowing for production in bacteria, a bacterial antibiotic resistance gene allowing for plasmid selection in bacterial culture, a strong constitutive promotor for optimal expression in mammalian cells (promoters derived from cytomegalovirus (CMV) or simian virus provide the highest gene expression), a polyadenylation sequence to stabilise the mRNA transcripts, such as bovine growth hormone (BHG) or simian virus polyadenylation, and a multiple cloning site for insertion of an antigen gene. An intron A sequence improves expression of genes remarkably. Many bacterial DNA vaccine vectors contain unmethylated cytidinephosphate-guanosine (CpG) dinucleotide motifs that may elicit strong innate immune responses in the host. In recent years there have been several approaches to enhance and customise the immune response to DNA vaccine constructs (2nd generation DNA vaccines). For instance dicistronic vectors or multiple geneexpressing plasmids have been used to express two genes simultaneously. Specific promoters have been engineered that restrict gene expression to certain tissues, and cytokine/antigen fusion genes have been constructed to enhance the immune response. Furthermore, genes may be codon optimised for optimal gene expression in the host and naïve leader sequences may be substituted with optimised leaders increasing translation efficiency.

The administration of DNA vaccine can be by saline or buffered saline injection of naked DNA or RNA, or injection of DNA plasmid or linear gene expressing DNA fragments coupled to particles, or inoculated by gene gun or delivered by a viral vector (virus like particle) such as Adenovirus, Modified vaccinia virus Ankara (MVA), Vaccinia, Adeno-associated virus (AAV), Alphavirus etc.

In one embodiment is a polypeptide comprising
a) an amino acid sequence comprising one or more surface exposed fragments of the same outer membrane protein expressed in a serotype of *Chlamydia* sp.; and
b) two or more additional amino acid sequences which is either the same sequence as defined in a) or is the corresponding surface exposed fragments from a variant of said outer membrane protein expressed in a serotype of *Chlamydia* sp., which is different from the serotype in a).

In a further embodiment is a polypeptide comprising 3 or more different amino acid sequences, where said amino acid sequences each comprises one or more surface exposed fragments from different variants of the same outer membrane protein that varies in different *Chlamydia* sp. serotypes, said amino acid sequences derived from different *Chlamydia* sp. serotypes.

In another further embodiment is a polypeptide comprising 3 or more repetitions of an amino acid sequence, where said amino acid sequence comprises one or more surface exposed fragments of the same outer membrane protein that varies in different *Chlamydia* sp. serotypes, said amino acid sequences derived from the same *Chlamydia* sp. serotype.

A polypeptide as described above is provided, wherein the outer membrane protein is MOMP from any serotype. The outer membrane protein may be MOMP from serotype D, E, F, G, Ia or J of *Chlamydia trachomatis* or *C. pneumoniae*. Still further, a polypeptide may comprise one or more of the variable domains 1, 2, 3, 4 of MOMP. These variable domain sequences may optionally be linearized. These variable domain sequences may comprise the variable domains 4 (VD4) of MOMP, and may be placed next to each other or be spaced with a linker. In an embodiment thereof is a polypeptide comprising an amino acid sequence defined in formula I:

$$xx_1\text{-VD4-}xx_2 \qquad \text{(Formula I)}$$

wherein
VD4 is independently selected from SEQ ID NO: 15-20 or an amino acid sequence which has at least 80% sequence identity herewith
and
$xx_1$ consists of
i) The amino acid sequence EWQASLAL-SYRLNMFTPYIGVKWSRASFDADTIRIAQPK (SEQ ID NO: 21) or
ii) A subsequence of the amino acid sequence in i) said subsequence comprising 1-38 amino acid residues, starting with the C-terminal K in the amino acid sequence in i)

and
$xx_2$ consists of
iii) The amino acid sequence DTMQI-VSLQLNKMKSRKSCGIAVGTTIVDA (SEQ ID NO: 22) or
iv) A subsequence of the amino acid sequence in iii) said subsequence comprising 1-29 amino acid residues, starting with the N-terminal D in the amino acid sequence in iii).
In these embodiments, the sequences may be chosen from SEQ ID NO: 23-28, 49-59.

Polypeptides according to any of the above embodiments are also provided additionally comprising a fragment comprising the variable domains 1 (VD1) of MOMP and wherein the amino acid sequences comprising VD1 of MOMP are placed next to each other or are spaced with a linker. In an embodiment thereof is a polypeptide comprising an amino acid sequence defined in formula II:

$$yy_1\text{-VD1-}yy_2 \qquad \text{(Formula II)}$$

wherein
VD1 is independently selected from SEQ ID NO: 1-6 or an amino acid sequence which has at least 80% sequence identity herewith and
$yy_1$ consists of
v) The amino acid sequence DAISMRVGYYGDFVFDRVLKTDVNKEFQMG SEQ ID NO: 7) or
vi) A subsequence of the amino acid sequence in v) said subsequence comprising 1-30 amino acid residues, starting with the C-terminal G in the amino acid sequence in v) and
$yy_2$ consists of
vii) The amino acid sequence NPAYGRHMQDAEMFT-NAA (SEQ ID NO: 8) or
viii) A subsequence of the amino acid sequence in vii) said subsequence comprising 1-18 amino acid residues, starting with the N-terminal N in the amino acid sequence in vii).
In these embodiments, the sequences may be chosen from SEQ ID NO: 9-14, 45-48.

Polypeptides according to any of the above embodiments are also provided comprising a fragment comprising the variable domains 2 (VD2) of MOMP and wherein the amino acid sequences comprising VD2 of MOMP are placed next to each other or are spaced with a linker. In an embodiment thereof is a polypeptide comprising an amino acid sequence defined in formula III:

$$zz_1\text{-VD2-}zz_2 \qquad \text{(Formula III)}$$

wherein
VD2 is independently selected from SEQ ID NO: 29-34 or an amino acid sequence which has at least 80% sequence identity herewith, and
$zz_1$ consists of
ix) The amino acid sequence TLGATSGYLKGN-SASFNLVGLFG (SEQ ID NO: 35) or
x) A subsequence of the amino acid sequence in ix) said subsequence comprising 1-23 amino acid residues, starting with the C-terminal G in the amino acid sequence in ix)
and
$xx_2$ consists of
xi) The amino acid sequence VVELYTDTTFAWSVGA-RAALWE (SEQ ID NO: 36) or xii) A subsequence of the amino acid sequence in xi) said subsequence comprising 1-22 amino acid residues, starting with the N-terminal V in the amino acid sequence in xi).

Polypeptides according to any of the above embodiments are also provided comprising a fragment comprising the variable domains 3 (VD3) of MOMP and wherein the amino acid sequences comprising VD3 of MOMP are placed next to each other or are spaced with a linker. In an embodiment thereof is a polypeptide comprising an amino acid sequence defined in formula IV:

$$qq_1\text{-VD3-}qq_2 \qquad \text{(Formula IV)}$$

wherein

VD3 is independently selected from SEQ ID NO: 37-42 or an amino acid sequence which has at least 80% sequence identity herewith, and $qq_1$ consists of xiii) The amino acid sequence ATL-GASFQYAQSKPKVEELNVLCNAAEFT-INKPKGYVG (SEQ ID NO: 43) or xiv) A subsequence of the amino acid sequence in xiii) said subsequence comprising 1-22 amino acid residues, starting with the C-terminal G in the amino acid sequence in xiii)

and $qq_2$ consists of xv) The amino acid sequence TGTKDASIDY-HEWQASLALSYRLNMFTPYIGVKWS (SEQ ID NO: 44) or xvi) A subsequence of the amino acid sequence in xv) said subsequence comprising 1-35 amino acid residues, starting with the N-terminal T in the amino acid sequence in xv).

Polypeptides according to any of the above embodiments are also provided comprising a moiety that facilitate export of the polypeptide when produced recombinantly (e.g. signal peptides), a moiety that facilitate purification of the fusion protein (e.g. his-tags) and/or a moiety which enhance the immunogenicity (e.g. a T cell antigen). In some embodiments, the enhancer of immunogenicity is an additional T-cell target which is chosen from a Ct antigen such as CT043, CT004, CT414, CT681 or part hereof. In these embodiments, said sequences may be chosen from SEQ ID NO: 60-68.

Still further provided are polypeptides according to any of the above embodiments, said polypeptide having the ability to a) neutralize *C. trachomatis* serovar D in vitro with a 50% neutralization titer of $10^{-3}$ or less, when tested in an experimental set-up comprising the administering heterologous immuno-repeats b) neutralize *C. trachomatis* serovar D in vivo in at least 50% of the mice at day 7 post infection when tested in a mouse model comprising administering heterologous immuno-repeats c) broaden the immune response to multiple serovars of *C. trachomatis* in vitro when administering a heterologous of immuno-repeats Still further provided are nucleic acids encoding a polypeptides according to any of the above embodiments.

Also provided are pharmaceutical compositions comprising a polypeptide according to any of the above embodiments or a nucleic acid according to any of the above embodiments. The pharmaceutical compositions may be vaccines. The pharmaceutical compositions may additionally comprise a pharmacologically acceptable carrier, excipient, adjuvant or immune modulator. The pharmaceutical compositions may include an adjuvant selected from DDA/TDB or alum. In further embodiments, pharmaceutical compositions may include a carrier that is a virus-like particle.

Still further provided are pharmaceutical compositions comprising a polypeptide according to any of the above embodiments or a nucleic acid according to any of the above embodiments for prophylactic or therapeutic use against *Chlamydia* sp. infections, including infections with *Chlamydia trachomatis* or *C. pneumoniae*.

Methods for preventing, treating and/or reducing the incidence of *Chlamydia* sp. infections, including infections with *Chlamydia trachomatis* and *C. pneumoniae*, said method comprising administering a pharmaceutical composition described herein are also provided.

Material and Methods

Cultivation of *C. trachomatis*

Ct serovar D, E and F was propagated in Hela 229 cells (ATCC, Rockville, MD, USA). The cells were cultivated in RP MI 1640 (Gibco BRL, Grand Island, NY, USA) media containing 5% fetal calf serum (Gibco BRL; heat inactivated), 1% v/v Hepes, 1% v/v L-glutamine, 1% v/v pyrovate and 10 µg/ml gentamycine. Semiconfluent monolayers of Hela 229 cells in 6 well-plates were infected with 1.5 inclusion forming unit per cell of Ct serovar E or F in 0.3 ml SPG-buffer/well. The plates were centrifuged 1 hour in a Heraeus Multifuge 3S at 750 g and incubated on a plate rocker for 2 h at 35° C. After 2 h 2 ml cultivation media supplemented with 5% glucose and 1 µg/ml cycloheximid were added pr. well and the cells were further incubated for 72 h at 37° C. in an atmosphere of 5% $CO_2$ in humidified air.

Harvesting of Ct

Chlamydiae were harvested 72 h post infection. The cells were dislodged from the wells with a cell scraper and centrifuged 30 minutes at 35.000 g and 4° C. The pellets were resuspended in HBSS, sonicated on ice and centrifuged at 500 g and 4° C. for 15 minutes. The supernatant was collected and saved on ice and the pellet was resuspended to same volume as before and sonication and centrifugation were repeated. The two supernatants were pooled and centrifuged 30 minutes at 30000 g and 4° C. and the pellet resuspended with a needle and syringe in a SPG buffer (3 ml/Plate). After a brief sonication the suspension was gently layered over a 30% Diatrizoate solution (50 g Meglumine diatrizoate, 7.7 g Sodium diatrizoate in 76 ml $H_2O$) and centrifuged at 40,000 g for 30 min. After centrifugation the pellet were resuspended in SP G buffer and stored at −70° C. The IFU of the batches were quantified by titration on McCoy cells and the concentration of the batches was determined by BCA.

Antigen and Fusion Preparation Methods

The genome of *C. trachomatis* serovar D, E, F and G are publicly available (NCBI-GenBank). Genes coding for *C. trachomatis* antigens and fusions where all obtained synthetically for cloning into *E. coli* bacterial protein expression system (DNA2.0). The pET411 vector was used for expression of the recombinant *C. trachomatis* protein in *E. coli* with a Histidine affinity tag. The bacterial host was BL21-STAR™. *E. coli* was grown at 37° C. to reach the logarithmic phase OD600 ~0.5 and protein expression was induced for 4 hours and cells were harvested by centrifugation (6,000 g for 15 min.). *E. coli* were lysed using Bugbuster (Novagen) containing Benzonase, rLysozyme and Protease inhibitor Cocktail I (C albiochem). Inclusion bodies were isolated by centrifugation (10,000 g for 10 min.) The pellet was dissolved in 50 mM NaH2PO4, 0.4M NaCl, 8M Urea, 10 mM Imidazole pH 7.5 and loaded onto HisTrap HP column (Amersham Biosciences) and bound proteins were eluted by applying a gradient of 50 to 500 mM imidazole. Depending on the antigen and fusions isoelectric point they were further purified by ion exchange chromatography. Protein concentrations was determined by BCA protein assay (Pierce).

Animals

Female B6C3F1 mice, 8-12 weeks of age, were obtained from Harlan Laboratories. Animals were housed under standard environmental conditions and provided standard food and water ad libitum. The use of mice is guided by the regulations set forward by the Danish Ministry of Justice (Lov om dyreforsøg, jvf lovbekendelser nr. 726 af 9. September 1993), and Animal protection committees. A detailed description of the experiments was submitted to and approved by the regional ethical review board (2012-15-2934-00100) held by the applicant Immunization Mice were immunized 3 times with 14 days between immunizations. The poly peptides were emulsified in CAF01 and administered simultaneously by the subcutanous (sc) and intranasal (i.n) route. The vaccines given by both routes consisted of 5 ug of peptide (see above) emulsified in 250 ug DDA and 100 ug TDB. As a negative control, DDA/TDB alone, without peptide was injected.

Chlamydia-Specific Cellular Responses

Blood lymfocytes or splenocytes were purified. Blood lymphocytes were pooled from 8 mice in each group and spenocytes were cultivated individually (n=4) and cultured in triplicate in round-bottomed microtiter plates (Nunc, Denmark) containing $2 \times 10^5$ cells/well in a volume of 200 µl RPMI-1640 supplemented with $5 \times 10^{-5}$ M 2-mercaptoethanol, 1 mM glutamine, 1% pyruvate, 1% penicillin-streptomycin, 1% HEPES and 10% fetal calf serum (FCS) (Invitrogen, Denmark). The cells were re-stimulated with individual antigens in 1-10 µg/ml or VD1 and VD4 peptide pools (2 µg/ml of each peptide). Stimulation with Concanavalin A (5 µg/ml) or media as positive control for cell viability and negative control, respectively. After 72 h of incubation at 37° C. in 5% $CO_2$, supernatants were harvested and stored at −20° C. before use. The amounts of secreted IFN-γ were determined by enzyme-linked immunosorbant assay (ELISA).

Serum Antibodies

At different time points post last vaccination the mice were bled and serum isolated by centrifugation. Serum was tested by ELISA for reactivity against the Ct surface (S vD, S vE and S vF), against the S vE VD4 monomer, and against peptides (Table 4&5) spanning the VD4 region of S vD, S vE and S vF. Briefly, plates were coated with antigen (1 to 10 ug/ml) at 4° C. in carbonate buffer overnight, blocked with BSA and washed. The plates were then incubated with pre-diluted samples at 4° C. overnight, washed and incubated with a peroxidase conjugated secondary antibody for 1 hr. Reactions were visualized by incubation with TMB substrate and the reaction stopped with sulphuric acid and read at 450 nm. When ELISA reactivity against a 9mer overlapping peptide panel spanning the VD4 region of S vD (S vE) (Table 6) and S vF (Table 7) was investigated minor changes were done. Briefly, plates were treated with streptavidin and coated with biotinylated peptides, blocked for 2 h at room temperature with skimmed-milk powder and washed. The plates were then incubated with pre-diluted (1:100) serum samples for 2 h at room temperature, washed and incubated with a peroxidase conjugated secondary antibody for 1 hr. Reactions were visualized by incubation with TMB substrate and the reaction stopped with sulphuric acid and read at 450 nm.

Neutralization Assay

Hak cells were grown to confluence in 96-well flat-bottom microtiter plates in RP MI 1640 media supplemented with 5% fetal calf serum (Gibco BRL; heat inactivated), 1% v/v Hepes, 1% v/v L-glutamine, 1% v/v pyrovate and 10 µg/ml gentamycine.

The Chlamydia stocks were previously titrated and diluted to $3 \times 10^6$ IFU/ml for S vE, $2 \times 10^6$ IF U/ml for S vD and $5 \times 10^6$ IFU/ml for S vF. Serum (pooled) isolated from vaccinated mice was heat inactivated at 56° C. for ½ h, diluted 2-4 times and 4-5 fold titrated. 80 µl of the bacteria suspension was mixed with 80 µl of serum (+/−20 µg/ml peptide) and incubated for 30 min. at 37° C. on a slowly rocking platform and 50 µl of the suspension were then inoculated onto the previously prepared Hak cells in dublicates. To do this, the media was removed from the Hak monolayers and 100 µl of the above media supplemented with 0.5% glucose and 10 µg/ml cyclohexamide was added followed by 50 µl of the serum/bacteria suspension. Plates were incubated at 35° C. on a slowly rocking platform, then inoculum was removed and 100 µl of the above media supplemented with 0.5% glucose and 10 µg/ml cyclohex-imide was added. The plates were then incubated for 24 h at 37° C. in an atmosphere of 5% $CO_2$ in humidified air. After incubation the medium was removed and the monolayers were fixed with 96% ethanol for 10 min. Inclusions were visualized by staining with polyclonal rabbit anti-CT755 serum made in our laboratory, followed by FITC-conjugated swine anti-rabbit immunoglobulin (Dako). Background staining was done with propidium iodide (Invitrogen)

Vaginal Challenge and Vaginal Chlamydial Load

Ten and 3 days before Ct serovar D challenge, the oestrus cycle was synchronized by injection of 2.5 mg Medroxy-progesteronacetat (Depo-Provera; Pfizer). Six weeks after the final vaccination the mice were challenged i.vag. with $4-8 \times 10^5$ IFU of Ct serovar D in 10 µl SPG buffer. Vaginal swabs were obtained at 3, 7, 10 and 14 days after infection. Swabs were vortexed with glass-beads in 0.6 ml SPG buffer and stored at −80 C until analysis. Infectious load was determined as described in 17. Briefly, McCoy cell monolayers were infected with a titrated volume of the swab suspension in duplicates. The plates were centrifuged at 750×g for 1 h at RT followed by incubation at 35 C for 2 h. Infection-media was then replaced with fresh media and the cells incubated at 37 C for 30 h. Inclusions were visualised by staining with polyclonal rabbit anti-CT681 serum made in our laboratory, followed by a FITC conjugated swine anti-rabbit Ig (DAKO, Glostrup, Denmark). Background staining was done with propidium iodide (Invitrogen, Taastrup, Denmark). Inclusions were enumerated by fluorescence microscopy observing at least 20 individual fields of vision for each well.

Depletion of CD4$^+$ and CD8$^+$ T-Cells

Monoclonal anti-mouse CD4 (clone GK1.5) and anti-mouse CD8 (clone YTS 156 and YTS 169 a gift from Stephen Cobbold)[78, 79] was purified from hybridoma supernatants made in our lab, using HiTrap protein G HP columns (GE-Healthcare Life Sciences, Denmark). The purified IgG was dialyzed against PBS, filtered through 0.22 µm filter and protein concentration was determined by OD 280 nm. Mice were depleted of CD4$^+$ or CD8$^+$ T-cells by 4 injections of 250-300 µg purified anti-CD4 or a mix of anti-CD8 antibodies at day −7, −4, −1 and +2 and +6 relative to the day of infection. The CD4$^+$ and CD8$^+$ T cell depletions were verified by FACS analysis on PBMCs at day 1 post infection using a FITC conjugated anti-CD4 antibody (clone RM4-4) and a PE-conjugated anti-CD8 antibody (clone 53-6) (BD Biosciences, Denmark).

In Vivo Depletion

The Chlamydia serovar D stock was previously titrated and diluted to 8×10⁴ IFU/μl, mixed 1:1 with serum isolated from mice immunized with a heterologous VD4 immuno-repeat S vD-S vE-S vF (CTH89). Ten and 3 days before Ct serovar D challenge, the oestrus cycle was synchronized by injection of 2.5 mg Medroxyprogesteronacetat (Depo-Provera; Pfizer). Mice were challenged i.vag. with 10 μl of the above mix (4×10⁵ IFU of Ct serovar D). Vaginal swabs were obtained at 3, 7 and 10 days after infection.

Statistical Analysis

Statistical analysis was done using GraphPad Prism 4. Medians of vaginal *Chlamydia* load were analyzed using Kruskall-Wallis followed by Dunn's post test or Mann-Whitney.

Example 1: Enhanced Immune Responses after Immunization with Homologous Immuno-Repeats of VD4$^{ext}$ Compared with a Monomeric VD4$^{ext}$ Unit Introduction Here we selected polypeptide units containing extended VD4 fragments of serovar E (for sequence see FIG. 2) (S vE VD4$^{ext}$). In order to potentiate the immune response against these domains we designed recombinant polypeptides were the SvEVD4$^{ext}$ unit was presented in a repetitive manner. To investigate if a repetitive form of the construct could enhance the antibody response compared to a monomeric form, we designed recombinant polypeptides where the units were presented either as a single unit or in a repetitive manner. For serovar E (S vE), a monomeric (S vE VD4$^{ext}$)*1 (CTH181), four immuno-repeats (S vE VD4$^{ext}$)*4 (CTH527) and eight immuno-repeats (S vE VD4$^{ext}$)*8 (CTH526) of the extended VD4 unit were constructed. These homologous immuno-repeat constructs were formulated in the adjuvant CAF01 and used to vaccinate mice; each mice was vaccinated with 2×5 μg peptide so the amount of VD4 was the same. Immunogenicity of the constructs was studied by ELISA against S vE VD4$^{ext}$, peptides covering S vE VD4$^{ext}$ and the bacterial surface of chlamydia.

Results

Figures 5A, 5B, 5C:
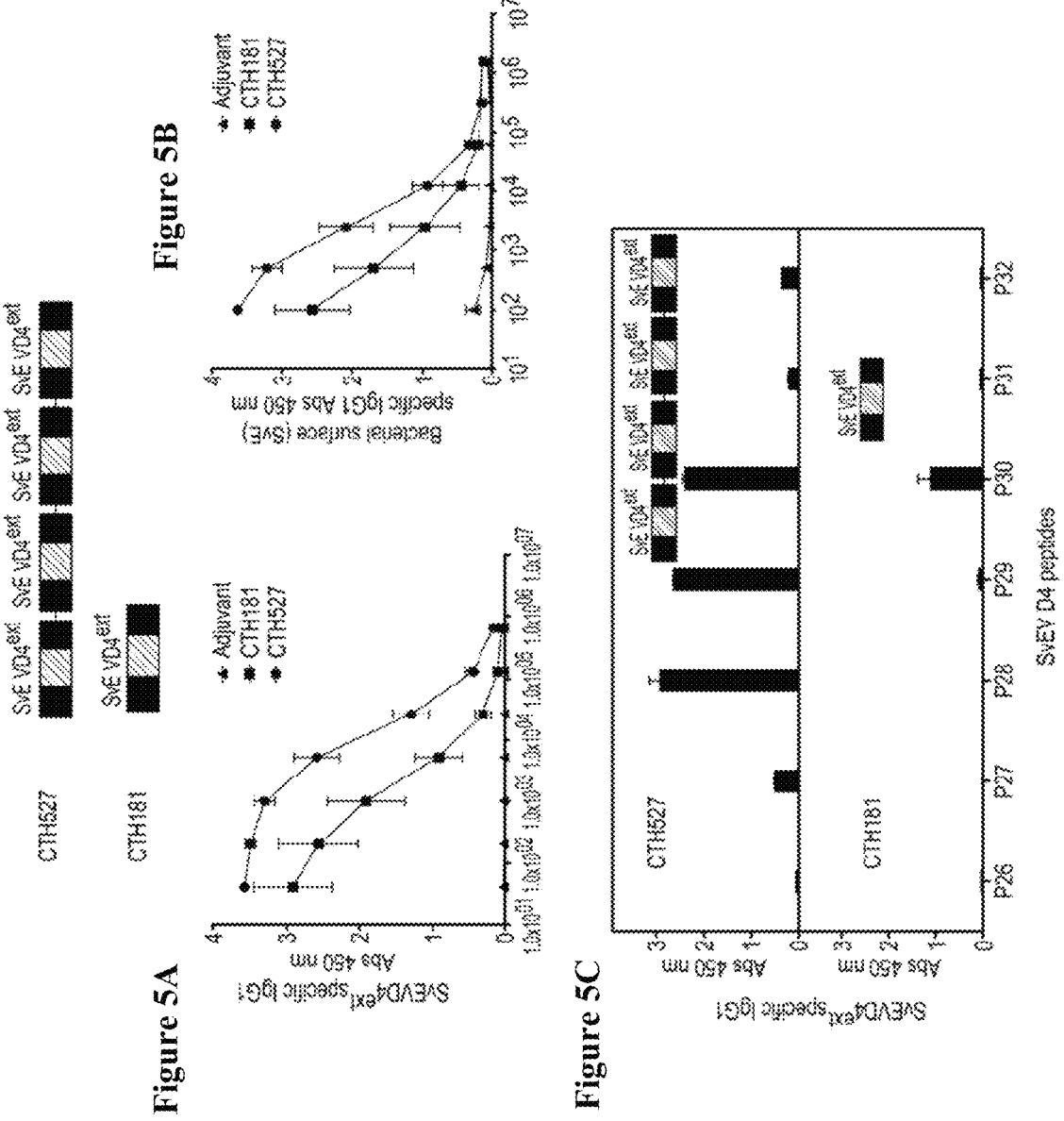
FIGS. 5A-5C. Enhanced and broadened immune responses after immunization with homologous immuno-repeats of VD4$^{ext}$ compared with a monomeric VD4$^{ext}$ unit.

Six mice/group were immunized 2 times with 14 days between immunizations. The vaccines (2×5 μg) were emulsified in CAF01 and administered simultaneously by the sc. and i.n routes. At certain time points post last vaccination blood was collected and antibody levels against the extended VD4 units from S vE and against the bacterial surface of S vE were measured by ELISA. Vaccination with a single VD4$^{ext}$ unit (monomeric VD4$^{ext}$, CTH181) induced lower levels of VD4$^{ext}$ specific antibodies compared to the level induced after immunization with homologous immuno-repeats composed of 4 VD4$^{ext}$ repeats of (S vE VD4$^{ext}$)*4 (FIG. 5A). The higher antibody response seen after immunizing with (S vE VD4$^{ext}$)*4 resulted in a stronger recognition of the bacterial surface compared to serum isolated from (VD4$^{ext}$)*1 immunized mice (FIG. 5B). The response to 20mer peptides with 10aa overlap spanning the extended VD4 region (Table 4) was also enhanced resulting in a broader epitope recognition pattern in the (VD4$^{ext}$)*4 homologous immuno-repeat groups compared to the group of mice immunized with a monomeric VD4$^{ext}$ unit when tested in a 1:500 serum dilution (FIG. 5C). In the group immunized with the monomeric construct the response was exclusively targeted to the central region containing the TTLNPTIAG (SEQ ID NO: 76) epitope whereas immunization with the homologous immuno-repeat exposed several B cell epitopes both up- and downstream of that epitope resulting in a diverse epitope recognition pattern of various epitopes. We continued by investigating if immuno-repeats of 8 (S vE VD4$^{ext}$)*8 (CTH526, seq no 30) were more immunogenic than immuno-repeats of 4 (S vE VD4$^{ext}$)*4. The two constructs induced similar levels of antibodies against the extended VD4 unit and against the bacterial surface of S vE.

Conclusion

We demonstrated that by immunizing with immuno-repeats of extended VD4 units from Serovar E we can greatly enhance antibody response both measured as the titer (FIGS. 5A&B) and the breadth of the response (FIG. 5C) directed against the extended VD4 unit resulting in a strong reactivity towards the bacterial surface. We did not find enhanced antibody titers and neutralization titers by increasing the number of repeats from 4 to 8.

Example 2: A Construct Composed of Heterologous Immuno-Repeats from S vD, E, F and G (CTH518) Induced a Stronger Response to Multiple Serovars Compared to Homologous Immuno-Repeats from S vF Introduction We investigated if immunization with at heterologous immuno-repeat composed of extended VD4 units from S vD, S vE, S vF and S vG (CTH518), maintained the strong immunogenicity and was able to induce a broader antibody response recognizing the surface of multiple serovars compared to immunization with a homologous immuno-repeat composed of extended VD4 units from S vF (S vF VD4$^{ext}$) *4, (CTH529). These immuno-repeat constructs were formulated in the adjuvant CAF01 and used to vaccinate mice. The immunogenicity of the constructs was studied by ELISA against the bacterial surface of Serovar D, E and F.

Results

Figure 6:
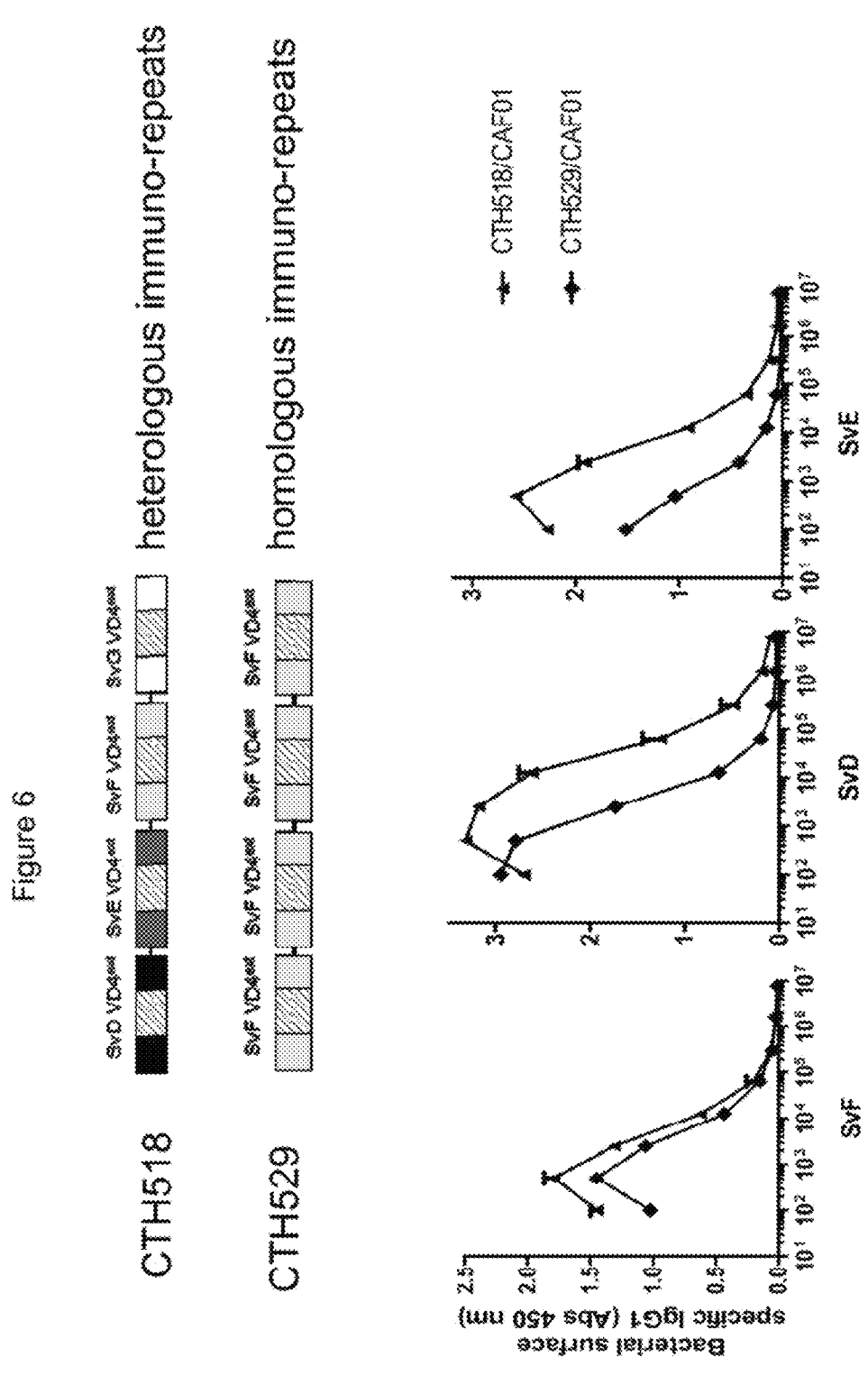
FIG. 6. A construct composed of heterologous immuno-repeats from S vD, E, F and G induced a stronger response to multiple serovars compared to homologous immuno-repeats from S vF.

Heterologous immuno-repeats promoted an antibody response that recognized the surface of the serovar F strain at the same high level as the response seen with a homologous immuno-repeat from S vF. However, by immunization with the heterologous immuno-repeat containing extended VD4 regions from the four serotypes (S vD, S vE, S vF, S vG) we observed a markedly increased titer to the D and E serovariants compared to the homologous immuno-repeat from the serovar F (FIG. 6).

Conclusion

Immunizing with the construct composed of immuno-repeats of heterologous extended VD4's induced a broader response recognizing the surface of multiple serovars (D, E and F) while maintaining the pronounced immunogenicity of the homologous immuno-repeat.

Example 3: The Specificity of the Antibody Responses after Immunization with a Heterologous Immuno-Repeat of the Extended VD4 Units from Serovar D, E, and F (CTH89) Compared to Constructs Composed of a Homologous Immuno-Repeat from (S vE$^{ext}$ VD4)*4, (S vF$^{ext.}$ VD4)*4 and a Previously Published A8-VD4 Peptide[65]

Introduction

We investigated the specificity of the immune response after immunization with a heterologous repeat of extended VD4 domains from S vD, S vE, S vF (CTH89) compared to immunization with homologous immuno-repeats composed of extended VD4 repeats from Serovar E (S vE$^{ext}$VD4)*4 (CTH527), S vF (S vF$^{ext}$VD4)*4 repeats (CTH524) and A8-VD4 peptide. These constructs were formulated in the adjuvant CAF01 and used to vaccinate mice. Immunogenicity of the constructs was studied by ELISA against a peptide panel (9 and 20 AA long) spanning the VD4 region of D, E and F (Tables 4-7). Serum (from 6 to 8 mice) was tested and a response above background but below OD=1.0 is indicated by an open box, responses above 1.0 are marked by a filled box. The length of the box indicates the area recognized by antibodies.

Results

Figure 7A:
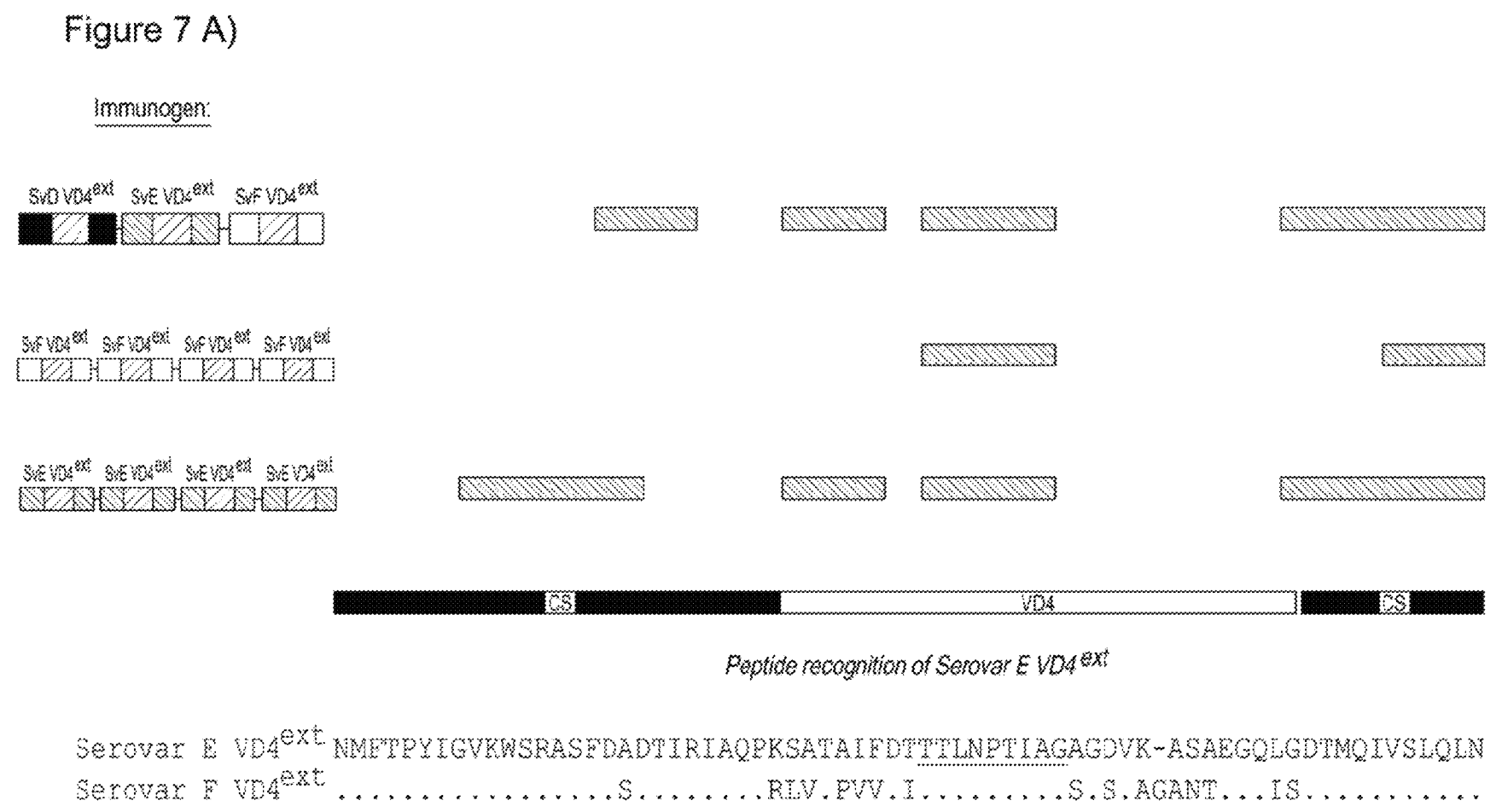
Figure 7:
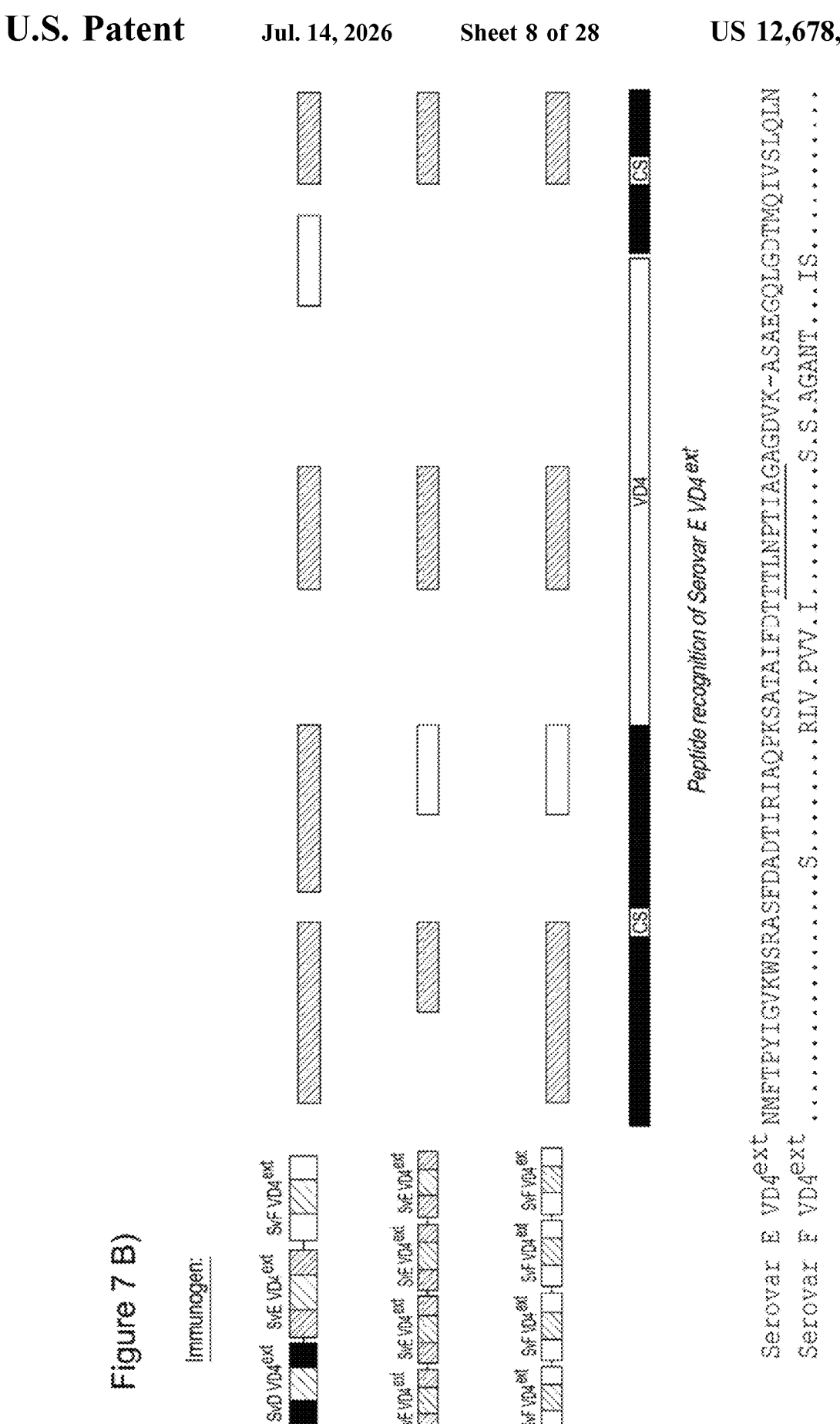

All constructs induced high antibody responses to the conserved TTLNPTIAG (SEQ ID NO: 76) part of the VD4$^{ext}$, located in the variable domain (VD). In general antibodies generated by homologous immuno-repeats were superior in recognizing their representative homologous VD4$^{ext}$ region, whereas it was evident that when these constructs were tested against peptides covering a VD4$^{ext}$ from a different serovar their epitope recognition repertoire was limited e.g. the recognition of serovar E VD4 region by serum from animals immunized with the construct (S vF$^{ext}$VD4)*4 (FIG. 7A and FIGS. 7C-A, 7C-B, and 7C-C) (and vice versa) (FIG. 7B and FIGS. 7C-A1, 7C-B1, and 7C-C1). Antibodies generated after immunization with the heterologous immuno-repeats (CTH89), recognized a much broader epitope repertoire than serum from animals immunized with the homologous immuno-repeats and the A8-VD4 (FIGS. 7A-7D-B). This construct was able to cover an epitope repertoire covering both serovar E and F at the level (or better) than achieved by immunizing with homologous immuno-repeats.

To demonstrate whether a 17 AA peptide representing a central VD4 peptide FDTTTLNPTIAGAGDVK (SEQ ID NO: 194) was able to compete with C. trachomatis organisms for CTH89 specific antibody binding, a competitive neutralization assay was performed. Different concentrations of CTH89 and A8-VD4 specific serum were mixed with the peptide in a concentration of 20 µg/ml (FIG. 7D-C). The results demonstrates that, in contrast to A8-VD4 specific serum, the peptide could not completely eliminate the neutralizing capacity of the CTH89 specific serum, suggesting that this serum targets a broader repertoire of neutralizing epitopes.

Conclusion

Immunizing with immuno-repeats of heterologous extended VD4's induced a broad response recognizing both conserved and serovar specific parts of the VD4 region, translating into a broader repertoire of neutralizing epitopes.

Example 4: Immunization with Heterologous Immuno-Repeats of Extended VD4's from S vD, S vE and S vF (CTH89) Generates Early T Cell Independent Protection after a S vD Challenge Introduction In order to study the effector mechanism responsible for the early protection seen after vaccination with the VD4 repetitive units, mice vaccinated with CTH89 were T cell depleted before challenge and the capacity to induce early protection was compared in depleted and non-depleted mice.

Results

Figures 8A, 8B, 8C, 8D, 8E:
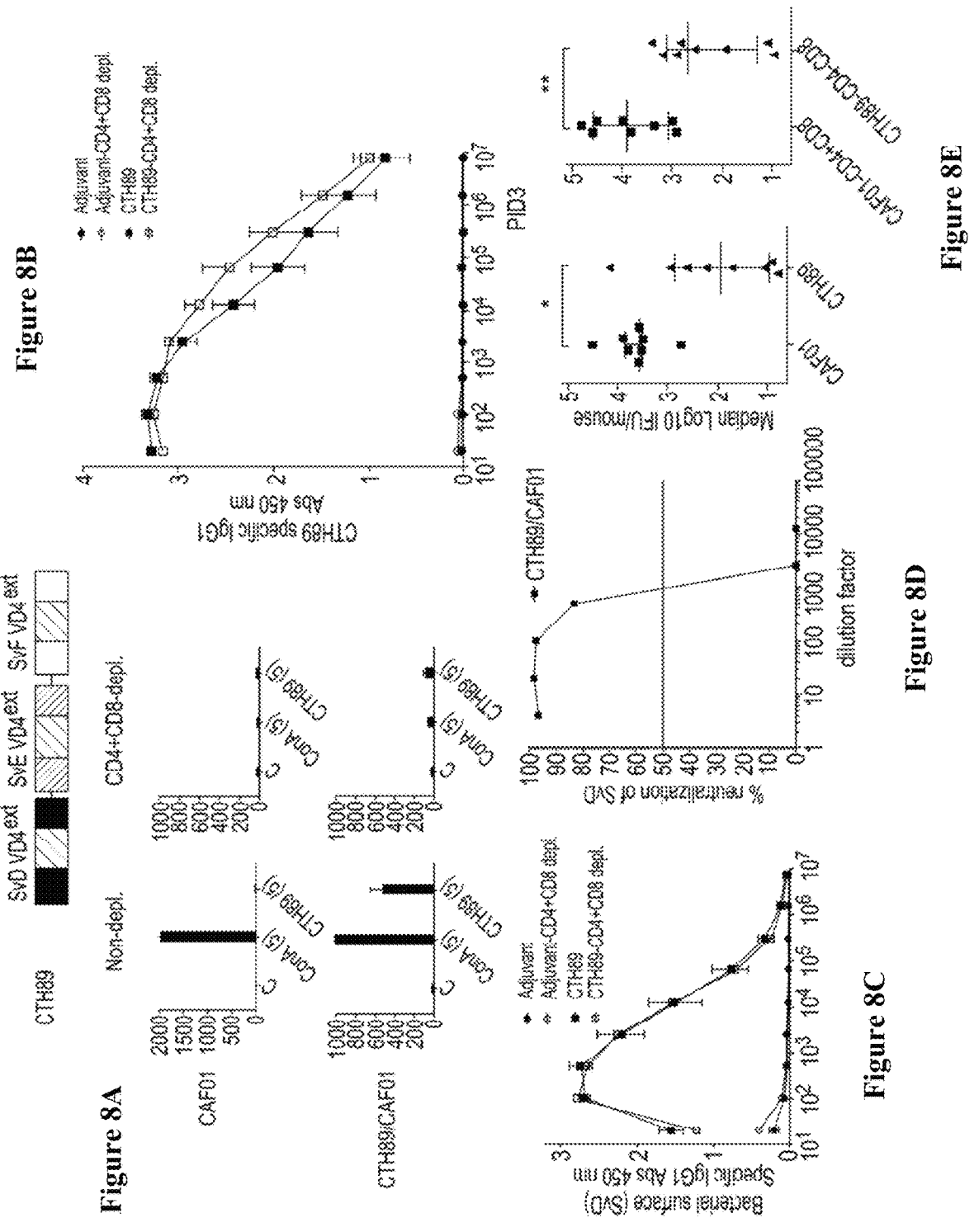
FIGS. 8A-8F. Immunization with heterologous immuno-repeats of extended VD4's from S vD, S vE and S vF (CTH89) generates early T cell independent protection after a S vD challenge.
Figure 8F:
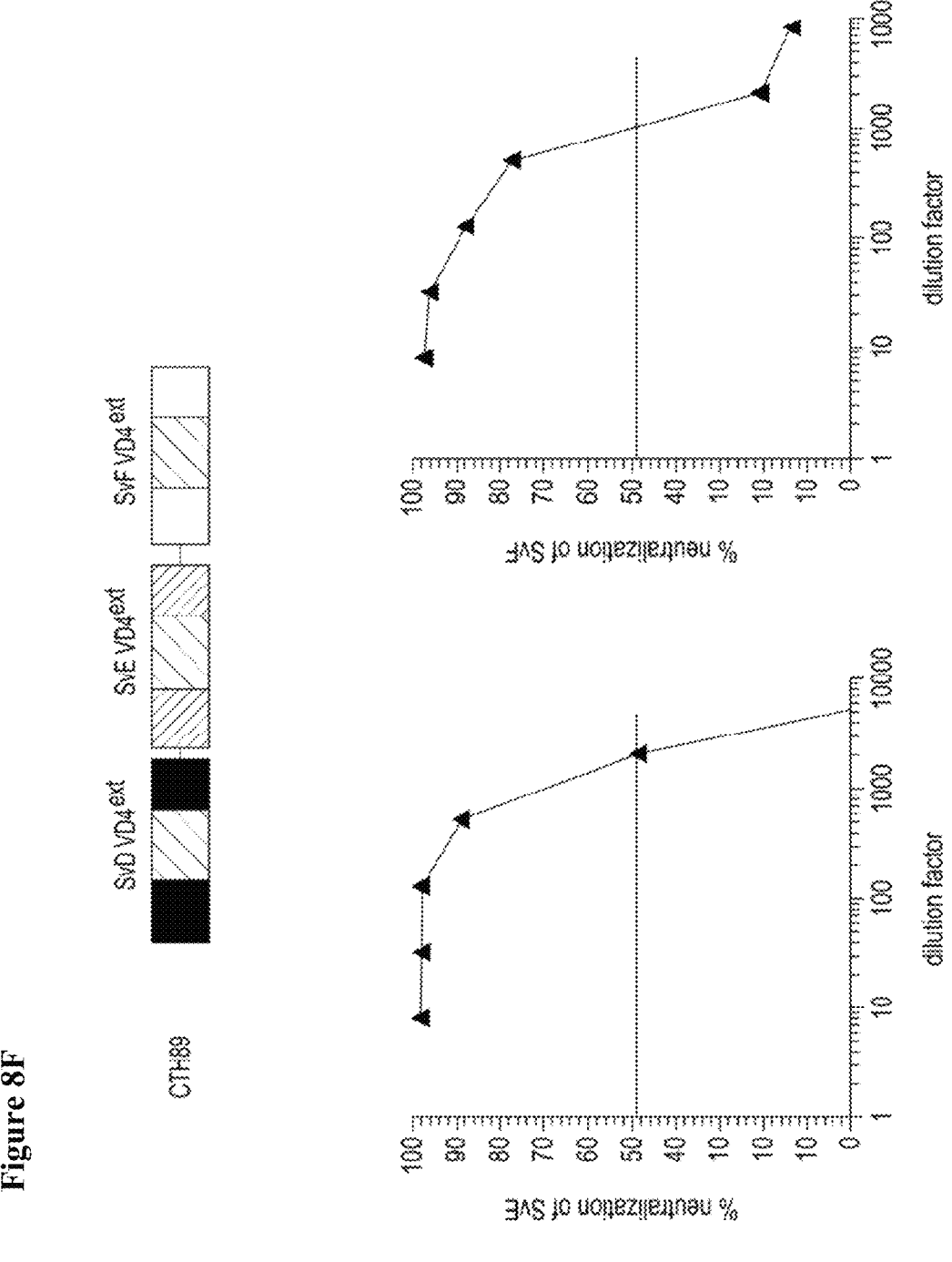

Eight mice/group were immunized 3 times with 14 days between immunizations. The vaccine (2×5 µg) was emulsified in CAF01 and administered simultaneously by the sc. and i.n routes. At certain time points post last vaccination the mice were bleed and antibody responses against chlamydia, the neutralization titer, and in vivo protection with and without T cell depletion were measured. Depletion of the T cell subset eliminated the T cell response to CTH89 (FIG. 8A). CTH89 induced a strong antibody response (FIG. 8B) that recognized the surface of serovar D (FIG. 8C) and was able to neutralize the bacteria in vitro with a 50% neutralization titer of around 1:10$^3$ (FIG. 8D). However, we still found significant protection at day 3 post challenge in the T cell depleted mice (FIG. 8E) suggesting an in vivo role for antibodies recognizing the VD4 unit in early protection against Chlamydia. Finally we demonstrated that CTH89 serum was also able to neutralize a S vE and S vF infection with very high 50% neutralization titers at the level of that obtained with S vD (FIG. 8F).

Conclusions

Immuno-repeat generates T cell independent early protection against vaginal challenge with Serovar D suggesting an in vivo role of VD4 specific antibodies.

Example 5: In Vivo Neutralization with CTH89 Specific Serum

Introduction

In order to investigate if the in vitro neutralization could be translated to a protective effect mediated by serum in vivo, we next investigated if S vD bacteria coated with antibodies generated after CTH89 immunization could neutralize/inhibit the infection in vivo compared to serum from naive mice.

Results

S vD bacteria were mixed with serum isolated from CTH89 immunized mice or serum isolated from naive mice. Depro-provera treated mice were then infected with 4×10$^5$ bacteria. Mice infected with S vD coated with CTH89 serum efficiently controlled bacterial replication compared to mice challenged with S vD coated with naive serum. Six out of 8 mice were cleared at day 7 and 10 compared to 2 and 3 respectively, in the control group (FIG. 9).

Conclusion

Figures 10A, 10B, 10C, 10D:
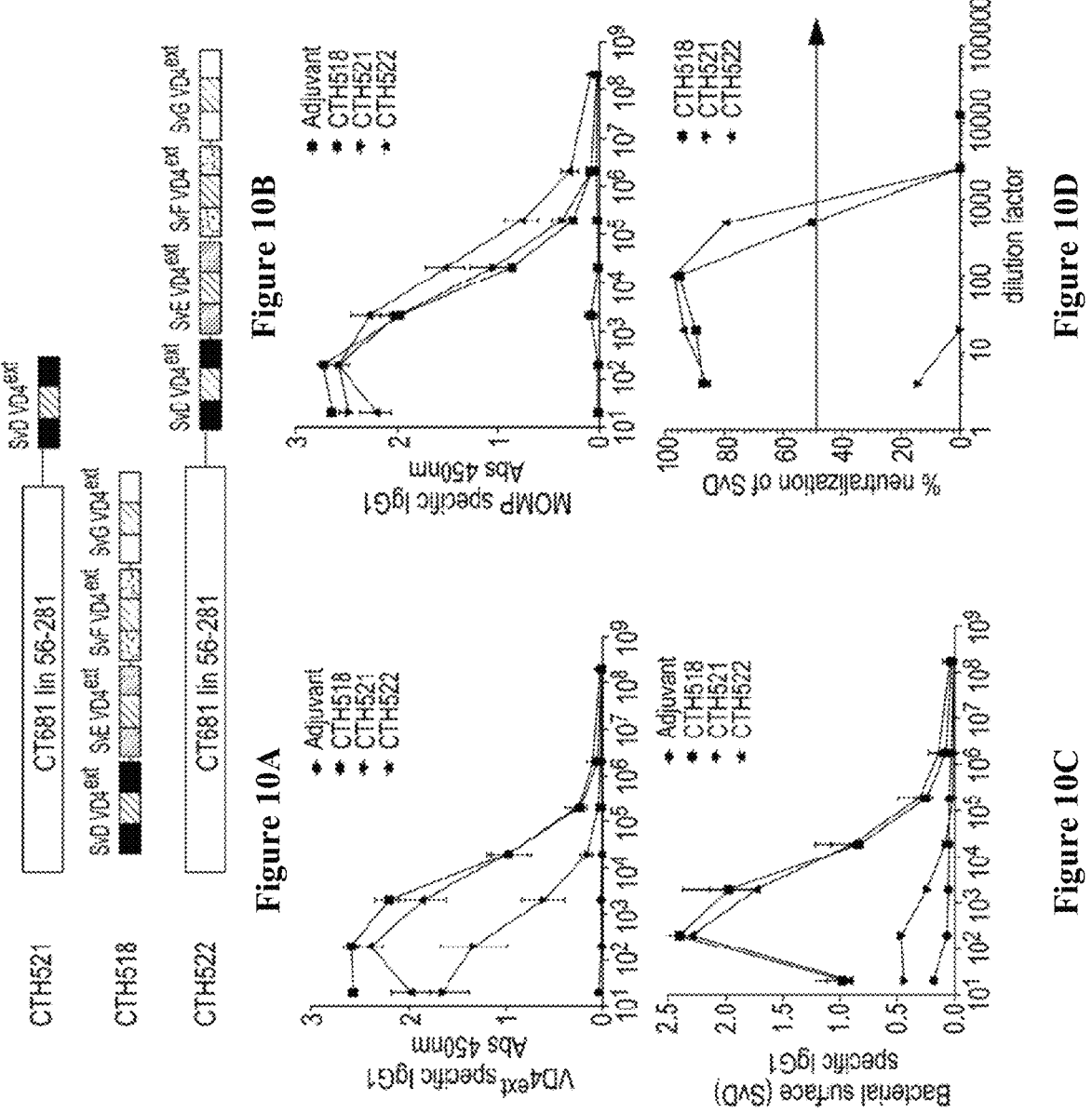
FIGS. 10A-10D. Coupling of heterologous immuno-repeats to recombinant MOMP.

Serum generated after immunization with heterologous VD4 immuno-repeat efficiently block infection of mice with S vD compared to serum isolated from naive mice Example 6. Fusion of Recombinant MOMP with Immuno-Repeats of Heterologous Extended VD4's Introduction MOMP is the target of both humoral and cellular immune-responses but despite the relative success of refolded native MOMP vaccines in generating neutralizing antibodies and protect against infection[54, 56], experimental vaccines based on recombinant MOMP (rMOMP) have failed. We designed a recombinant MOMP ranging from amino acid 56 to 349, including all variable domains (CTH521). We also selected polypeptide units containing extended VD4 fragments (covering the VD4 variable domain of MOMP and the adjacent conserved flanking regions) of serovar D, E, F and G (CT518) Finally a hybrid was constructed where CTH521 was fused to CTH518 (CT522) (FIG. 10).
Results Eight mice/group were immunized 3 times with 14 days between immunizations. The vaccines were emulsified in CAF01 and administered simultaneously by the sc. (5 µg) and i.n. (5 µg) routes. Post vaccination blood samples were collected and antibodies against the VD4$^{ext}$ unit, recombinant MOMP and against the bacterial surface were measured. Antibodies generated after immunization with CT522 and CT518 recognized the VD4 region (FIG. 10A) and the bacterial surface (FIG. 10C) at a much higher level compared to serum isolated after CT521 immunization. Furthermore antibodies form CTH518 and CTH522 were able to neutralize a S vD infection at the same level and much higher than CTH521 (FIG. 10D).
Conclusion Fusion of recombinant MOMP with immuno-repeats of heterologous extended VD4's results in a molecule that elicits the same functional antibody response as the immunerepeat alone.

Example 7: Vaccination with Heterologous Immuno-Repeats of VD1$^{ext}$-VD4$^{ext}$'s Regions from S vD, S vE and S vF (CTH88) Compared to Vaccination with a Single VD1-VD4 Unit from S vD (CTH87)

Introduction

We next investigated if it was possible to fuse another VD region to the extended VD4 region and still maintain the capacity to induce neutralizing antibodies. Therefore constructs were designed were an extended version of the VD1 region was coupled to the extended VD4 region. We produced both a homologous unit composed of an extended unit of VD1 and VD4 from S vD (CTH87) and a heterologous immuno-repeat composed of extended units of VD1 and VD4 from different serovars (D, E and F; CTH88).
Results 12 mice/group were immunized 3 times with 14 days between immunizations. The vaccines were emulsified in CAF01 and administered simultaneously by the sc. (5 µg) and i.n. (5 µg) routes Antibodies from mice immunized with CTH87 recognized the bacterial surface of both S vD, S vE and S vF (FIG. 11A); with the highest titers observed against the homologous S vD strain and the lowest titers against the most distant S vF. Immunizing with immuno-repeats of heterologous VD1$^{ext}$-VD4$^{ext}$ units resulted in significant higher levels of antibodies against the surface of the bacteria compared to the monomeric construct and broadened the response resulting in titers increasing 6-12 times against S vD and S vE and almost 25 times against S vF (FIG. 11A). The capacity of these antibodies to neutralize infection in an in vitro neutralizing assay was even more improved as serum from animals immunized with the monomeric VD1$^{ext}$-VD4$^{ext}$ construct from serovar D only had minimal neutralizing capacity compared to the heterologous VD1-VD4 immuno-repeat construct with a neutralization titer of 1:2000 (FIG. 11B). Finally did vaccination with the heterologous VD1$^{ext}$-VD4$^{ext}$ immuno-repeat construct very efficiently protect against a S vD challenge in a vaginal challenge model (FIG. 11C).
Conclusion We demonstrated that by immunizing with immuno-repeats of heterologous VD1$^{ext}$-VD4$^{ext}$ units from serovar D, E and F, we can greatly enhance the antibody response directed against the bacterial surface of all three serovariants. Importantly we also show that by vaccination with a heterologous immuno-repeat, we observe a selective higher increase in Serovar F surface recognition (25 times vs. 6-12 times for serovar D and E), suggesting that the heterologous immuno-repeats not only increase the antibody levels against shared epitopes but also against serovar F specific epitopes. We demonstrated that the antibodies induced with immuno-repeats of heterologous VD1-VD4 (CTH88) generated in vitro neutralizing titers that resulted in early in vivo protection compared to the single VD1-VD4 unit from S vD (CTH87) (FIG. 11C).

Example 8: Coupling of T Cell Antigens to Immuno-Repeats of VD4

Introduction

Figures 12A, 12B, 12C, 12D:
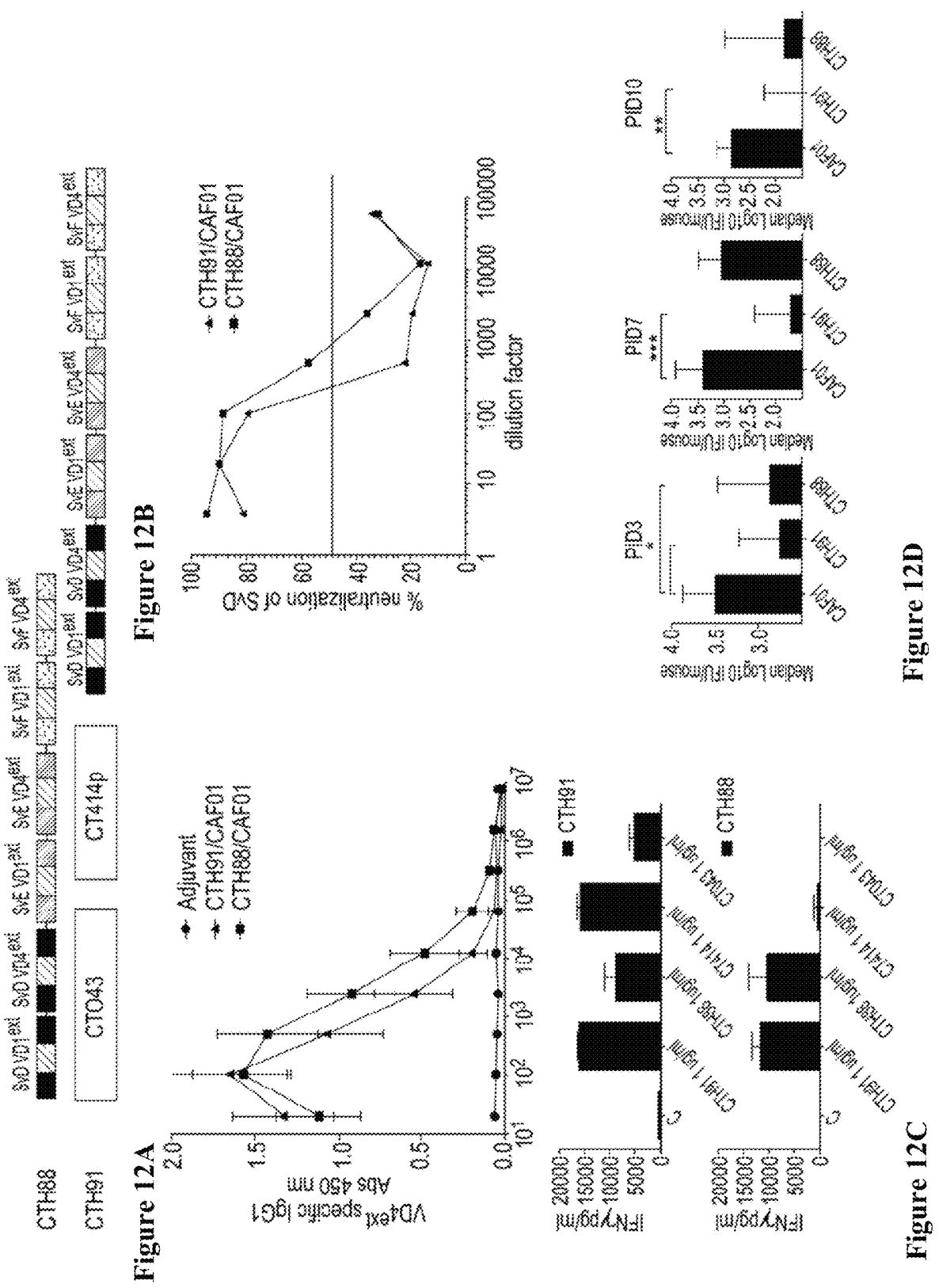
FIGS. 12A-12D. Coupling of T cell antigens to immuno-repeats of VD4

As there is a generally recognized need for a CMI component in an efficient protective immune response against *Chlamydia trachomatis*, we next investigated if the heterologous immuno-repeats can be fused to T cell antigens with vaccine potential. Our aim was to provide both an early antibody mediated protection against Ct as well as an efficient CMI mediated clearance of residual organisms. A constructs composed of CT043, and part of CT414 and CT681 was fused to immuno-repeats of heterologous VD1-VD4 (CTH91).
Results 12 mice/group were immunized 3 times with 14 days between immunizations. The vaccines (2×5 µg) were emulsified in CAF01 and administered by the sc. and i.n. routes. At various time points post last vaccination the mice were bleed and antibody responses and neutralization titers were measured. Antibodies generated after immunization with CTH91 and CTH88 recognized the VD4$^{ext}$ region at similar levels (FIG. 12A) and serum isolated from both groups were able to neutralize a S vD infection (FIG. 12B). Compared to CTH88 immunized mice the T cell response to CTH91 was stronger with recognition of both CT414 and CT043 (FIG. 12C). This T and B cell response resulted in significant protection at day 3 post infection for both groups, but at day 7 and 10 post infection the group vaccinated with a fused T and B cell target (CTH91) induced higher levels of protection compared to CTH88 (FIG. 12D).
Conclusion We were able to fuse T cell antigens with the repetitive VD regions and still maintain the capacity to induce early protection and moreover these constructs induced an efficient CMI mediated clearance of residual organisms leading to high levels of protection at day 7 post infection.

Example 9: Immunization with a Cocktail of a Heterologous VD4 Immuno-Repeat and a T Cell Antigen Fusion Molecule Introduction We next investigated if immuno-repeats can be mixed with T cell antigens with vaccine potential and still provide both an early antibody mediated protection against Ct as well as an efficient CMI mediated clearance of residual organisms. We therefore investigated if we could mix a strong T cell hybrid composed of CT043, part of CT414 and CT681 (CTH93) with CTH89 (FIG. 13A) and still maintain the capacity to neutralize the S vD bacteria in vitro and induce early protection against a vaginal challenge.

Figures 13A, 13B, 13C:
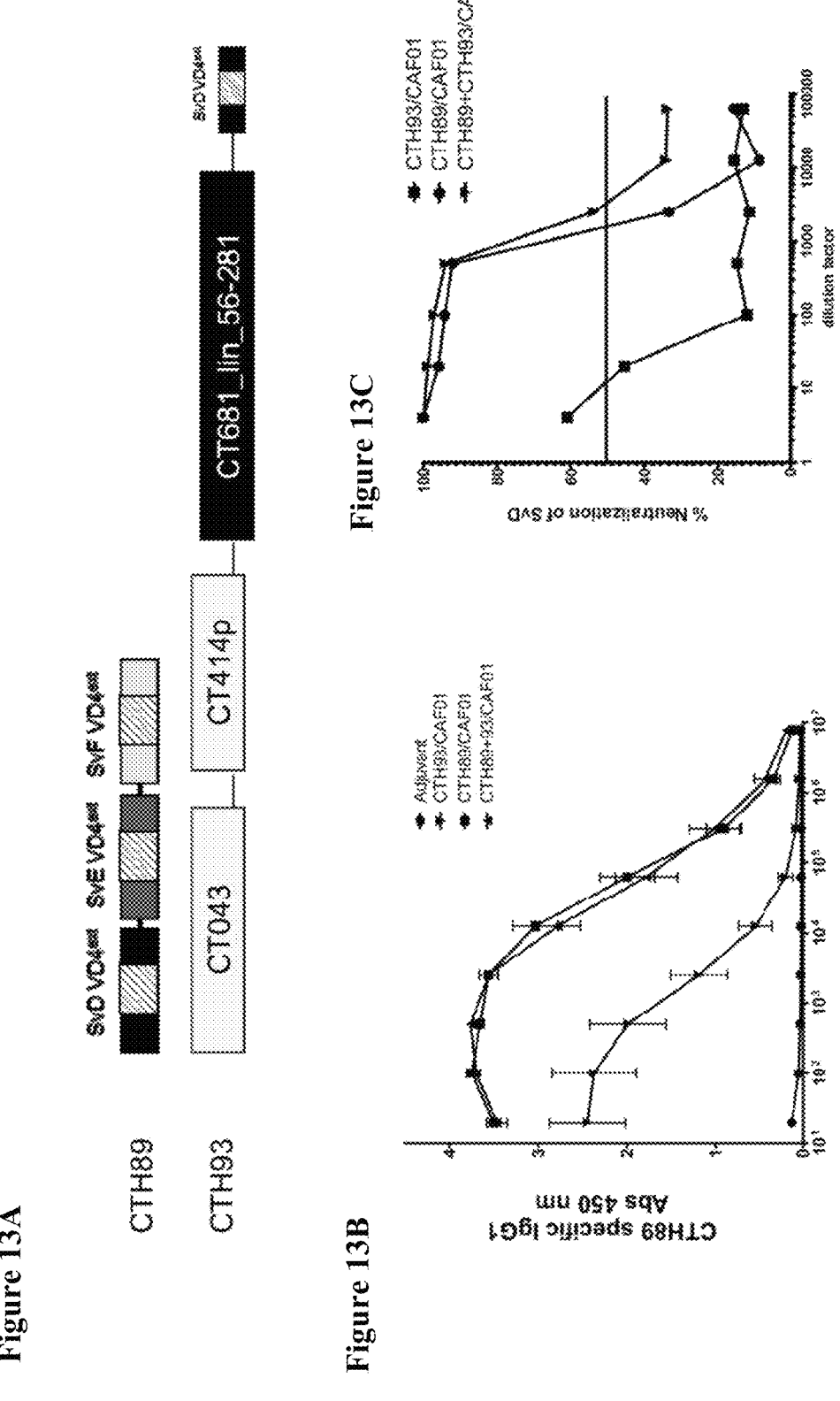
FIGS. 13A-13E. Immunization with a cocktail of a heterologous VD4 immuno-repeat and a T cell antigen fusion molecule FIGS. 14A-14B. Comparison of CAF01 and Alum as adjuvant delivery system.
Figures 13D, 13E:
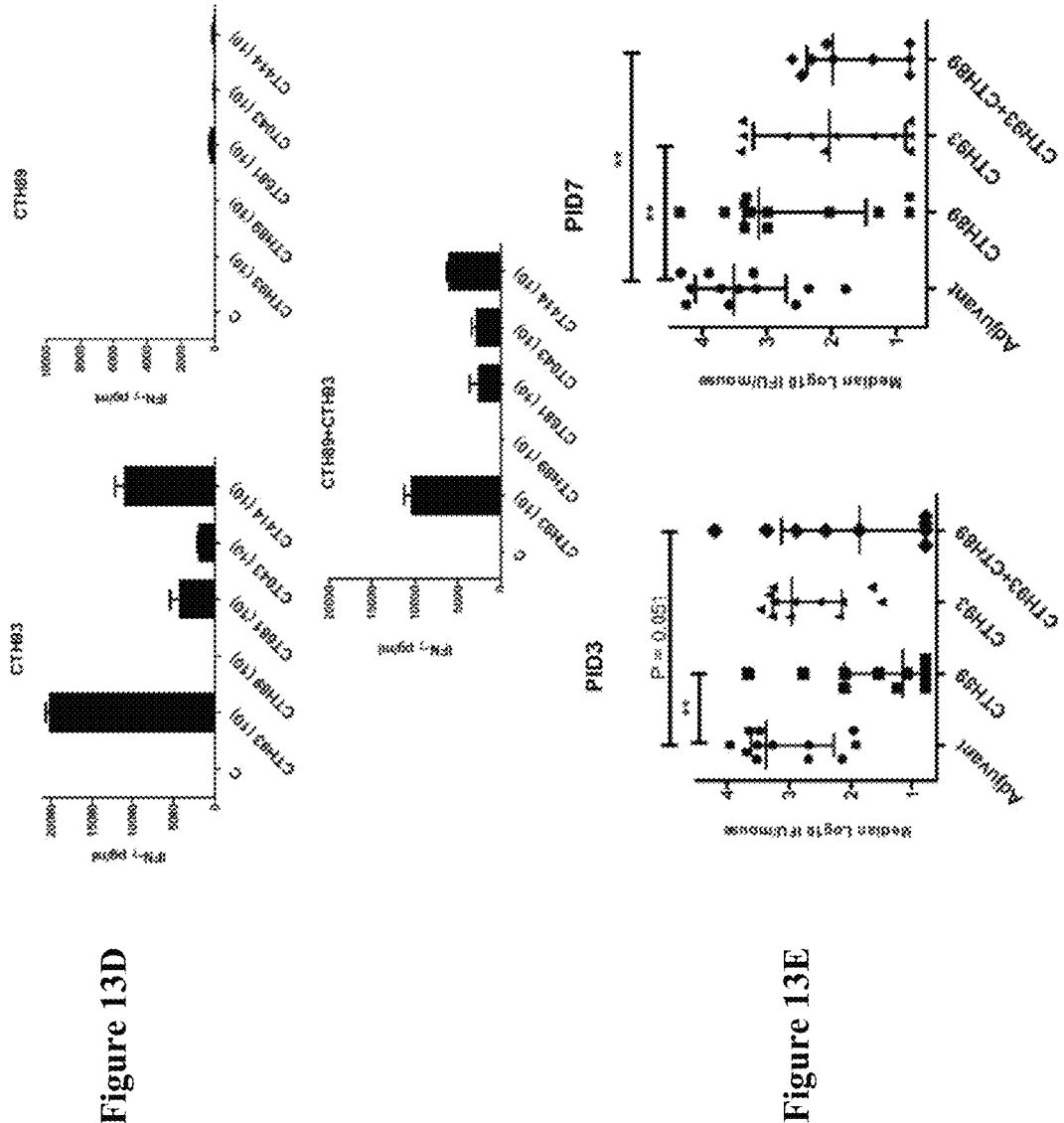

Results 12 mice/group were immunized 3 times with 14 days between immunizations. The vaccine (2×5 µg) were emulsified in CAF01 and administered simultaneously by the subcutaneous (sc) and intranasal (i.n) route (FIG. 13). Antibodies generated after immunization with CTH89 or the mixture of CTH89 and CTH93 strongly recognized the VD4 regions (FIG. 13B) and neutralized the bacteria with similar 50% neutralization titers (FIG. 13C). Much reduced levels of VD4 recognition and neutralization was seen after vaccination with the T cell antigen fusion (CTH93, FIG. 13D) although this molecules also contained MOMP (CT681) and therefore potentially the same neutralizing epitopes. This molecule also gave very low levels of recognition of the TTLNPTIAG (SEQ ID NO: 76) epitope (data not shown). This clearly emphasizes the limitation of full-size recombinant MOMP as a vaccine antigen for the induction of neutralizing antibodies as previously reported. Both the CTH89 and the cocktail of the CTH89 and CTH93 vaccines induced protection at day 3 post infection (FIG. 13E). This was in contrast to CTH93 vaccinated mice which induced no significant protection at day 3 post infection. At day 7 post infection both vaccines including the strong T cell target (CTH93) induced a significant level of protection (FIGS. 13D&E).

Conclusions

We were able to mix the heterologous VD4 repeats with strong T cell antigens without the loss of in vitro neutralization and early in vivo protection against a Serovar D challenge. Moreover, the mix of B and T cell targets induced an efficient CMI mediated clearance of residual organisms leading to high levels of protection at day 7 post infection.

Example 10: Testing the Effect of Different Adjuvant Systems

Introduction

In order to investigate if the high antibody response against heterologous immuno-repeats were only seen when the vaccine were administered in CAF01-we compared the antibody response and the neutralization titer after immunizing with CTH527 (S vE VD4$^{ext}$)*4 in CAF01 or Alum.

Results

Figures 14A, 14B:
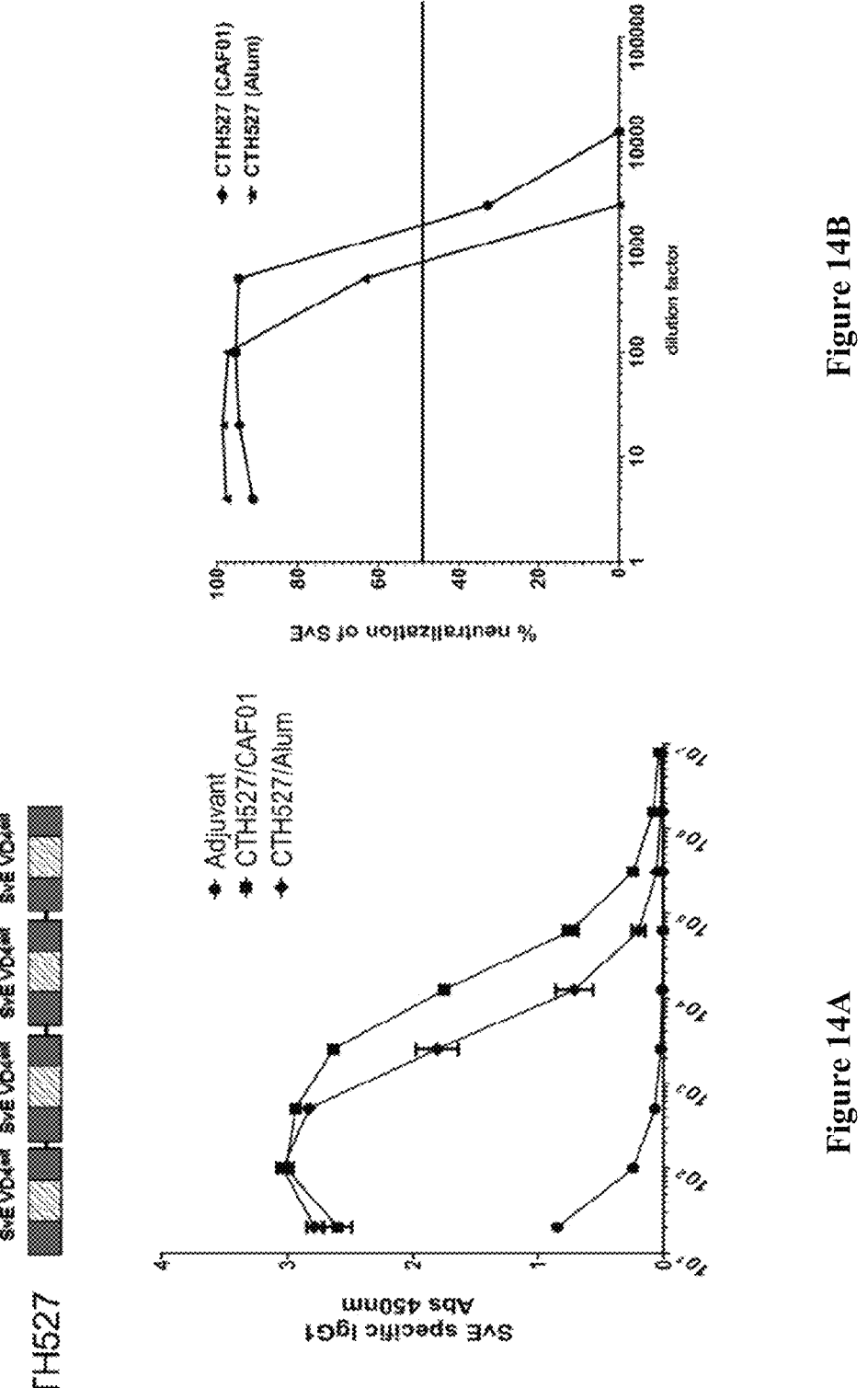

Both adjuvant systems induced a high antibody response against the surface of S vE when administered together with CTH527 (FIG. 14A), and the antibodies from both groups were able to neutralize S vE in vitro (FIG. 14B).

Figures 15A, 15B, 15C:
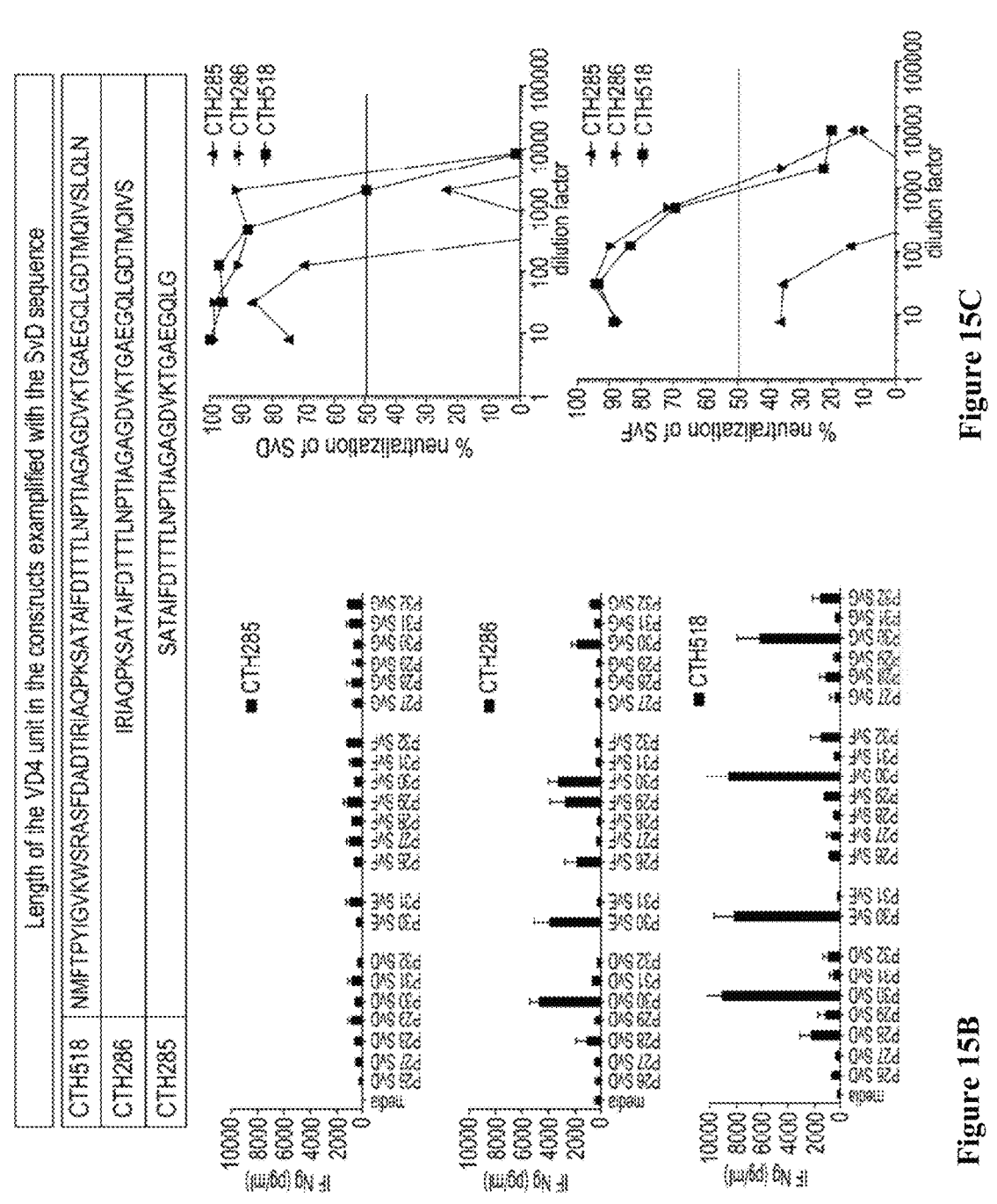
FIGS. 15A-15C. Vaccination with heterologous immuno-repeats composed of reduced length of the VD4$^{ext}$ regions from S vD, S vE, S vF and S vG. The CTH518 sequence shown is amino acids 1 through 68 of SEQ ID NO 53. The CTH286 sequence shown is amino acids 21 through 64 of SEQ ID NO 53. The CTH285 sequence shown is amino acids 28 through 57 of SEQ ID NO: 53.

Example 11: Vaccination with Heterologous Immuno-Repeats Composed of Reduced Length of the VD4$^{ext}$ Regions from S vD, S vE, S vF and S vG Introduction We next compared heterologous immuno-repeat constructs composed of reduced length of the VD4 region (CTH285 (SEQ ID NO: 69) and CTH286 (SEQ ID NO: 70)) compared to the CTH518 construct (CTH518 (SEQ ID NO: 53)) (FIG. 15A).

Results 4 mice/group were immunized 3 times with 14 days between immunizations. The vaccines were emulsified in CAF01 and administered simultaneously by the subcutaneous (sc, 5 µg) and intranasal (i.n, 5 µg) routes. Splenocytes from 4 mice/group were isolated and the T cell responses to overlapping peptides representing the VD4$^{ext}$ region (FIG. 15B) and the capacity of the serum to neutralize a serovar D and F infection (FIG. 15C) were investigated. Much reduced levels of VD4 T cell recognition, and neutralization was seen after vaccination with CTH285 where the VD4$^{ext}$ regions from the different serovars were reduced with 38 aa. CTH286 on the other hand (each VD4$^{ext}$ region reduced with 24 aa) induced similar levels of T cell responses and had the same capacity to neutralize a serovar D infection as CTH518.

Conclusion

We demonstrated that by reducing the length of the VD4$^{ext}$ regions with 38 aa we reduced both the T cell responses and the capacity to neutralize a serovar D and F infection.

Figures 16A, 16B, 16C, 16D:
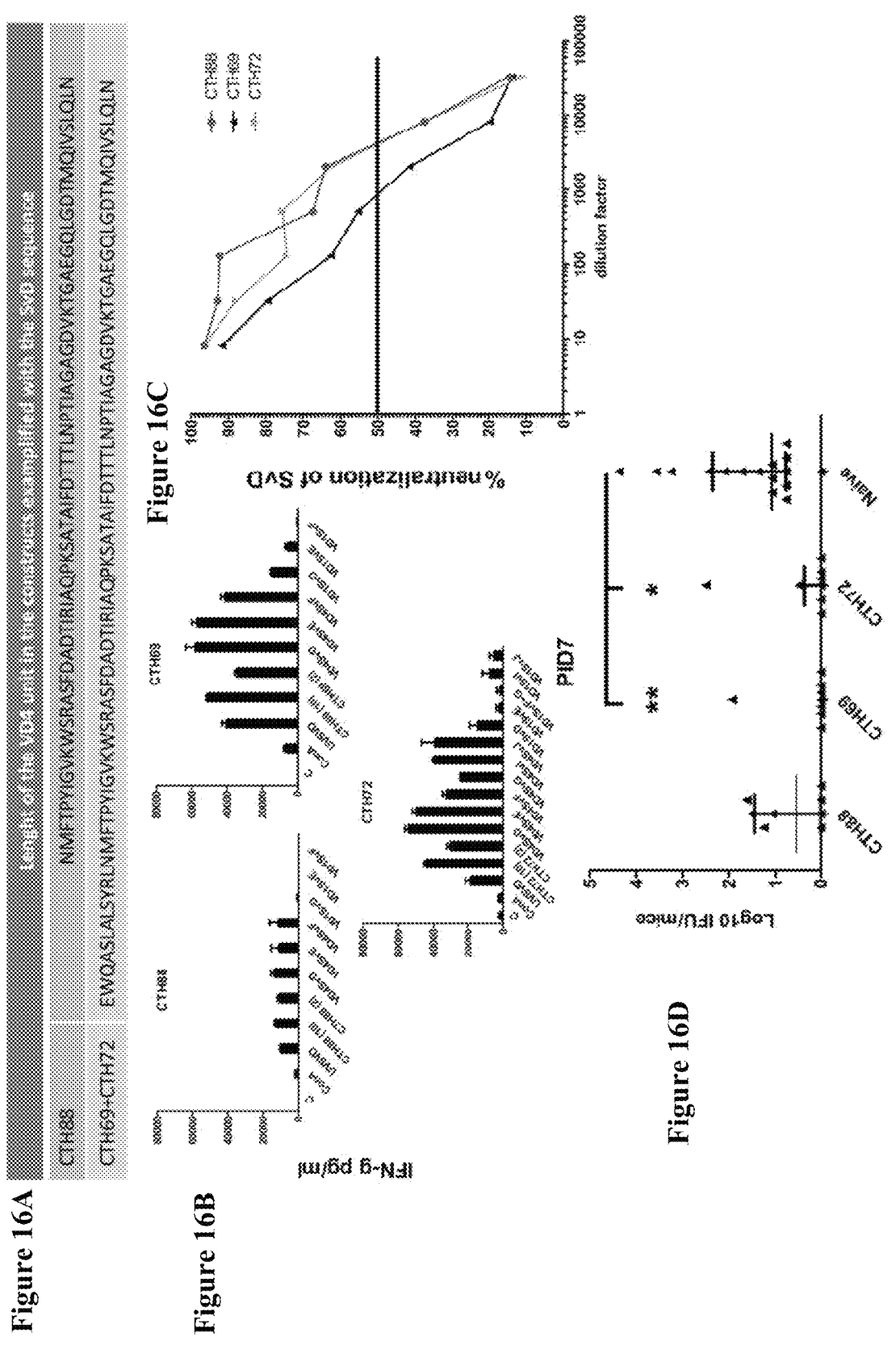
FIGS. 16A-16D. Vaccination with heterologous immuno-repeats composed of extended VD4$^{ext}$ regions from S vD, S vE, S vF, S vG, S vIa and S vJ. The CTH88 sequence shown is amino acids 60 through 127 of SEQ ID NO: 46. The CTH69+CTH72 sequence shown is SEQ ID NO: 255.

Example 12: Vaccination with Heterologous Immuno-Repeats Composed of Extended VD4$^{ext}$ Regions from S vD, S vE, S vF, S vG, S vIa and S vJ Introduction We next investigated if we by extending the length of the VD4$^{ext}$ region could enhance the T cell response to the immuno-repeat constructs. We designed two constructs CTH69 (SEQ ID NO: 47) and CTH72 (SEQ ID NO: 48) (FIG. 16A). CTH69 was similar to CTH88 but the VD4$^{ext}$ regions from S vD, S vE and S vF was extended by 12aa N-terminally (FIG. 16B). CTH72 also contained VD1 and VD4$^{ext}$ regions from S vG, S vIa and S vJ.

Results

Mice were immunized 3 times with 14 days between immunizations. The vaccines were emulsified in CAF01 and administered simultaneously by the subcutaneous (sc, 5 µg) and intranasal (i.n, 5 µg) routes. T cell responses to the antigen used for immunization and to peptide pools representing the VD1 and VD4 regions from the different serovars were investigated (FIGS. 16A-D). Extending the VD4$^{ext}$ regions induced a significant higher T cell response (>40.000 µg/ml) compared to the T cell response obtained with CTH88 (<20.000 pg/ml) (FIG. 16B). Importantly, both of the extended constructs were still able to neutralize a serovar D infection in vitro (FIG. 16C). Comparing the protective efficacy of the vaccines, CTH69 and CTH72 induced a significant level of protection at day 7 post infection which could possibly be explained by the stronger T cell response induced by these vaccines compared to CTH88 (FIG. 16D).

Conclusion

Extending the VD4$^{ext}$ region enhanced the T cell response compared to CTH88 which led to enhanced protection at day 7 post infection.

REFERENCES

1. WHO. Global Prevalence and Incidence of selected Curable Sexually Transmitted Infections: Overview and Estimates. *World Health Organization*, Geneva, Switzerland; 2001.
2. Paavonen J, Eggert-Kruse W. *Chlamydia trachomatis*: impact on human reproduction. *Hum Reprod Update* 1999, 5(5): 433-447.
3. Plummer F A, Simonsen J N, Cameron D W, Ndinya-Achola J O, Kreiss J K, Gakinya M N, et al. Cofactors in male-female sexual transmission of human immunodeficiency virus type 1. *J Infect Dis* 1991, 163(2): 233-239.

4. Anttila T, Saikku P, Koskela P, Bloigu A, Dillner J, Ikaheimo I, et al. Serotypes of *Chlamydia trachomatis* and risk for development of cervical squamous cell carcinoma. *Jama* 2001, 285(1): 47-51.

5. Golden M R, Schillinger J A, Markowitz L, St Louis M E. Duration of untreated genital infections with *Chlamydia trachomatis*: a review of the literature. *Sex Transm Dis* 2000, 27(6): 329-337.

6. Batteiger B E, Xu F, Johnson R E, Rekart M L. Protective immunity to *Chlamydia trachomatis* genital infection: evidence from human studies. *J Infect Dis,* 201 Suppl 2: S178-189.

7. Brunham R C, Rey-Ladino J. Immunology of Chlamydia infection: implications for a *Chlamydia trachomatis* vaccine. *Nat Rev Immunol* 2005, 5(2): 149-161.

8. Su H, Caldwell H D. CD4+ T cells play a significant role in adoptive immunity to *Chlamydia trachomatis* infection of the mouse genital tract. *Infect Immun* 1995, 63(9): 3302-3308.

9. Morrison S G, Su H, Caldwell H D, Morrison R P. Immunity to murine *Chlamydia trachomatis* genital tract reinfection involves B cells and CD4 (+) T cells but not CD8 (+) T cells. *Infect Immun* 2000, 68(12): 6979-6987.

10. Morrison R P, Caldwell H D. Immunity to murine chlamydial genital infection. *Infect Immun* 2002, 70(6): 2741-2751.

11. Rasmussen S J. Chlamydia immunology. *Curr Opin Infect Dis* 1998, 11(1): 37-41.

12. Rank R. In: Chlamydia Intracellular Biology, Pathogenesis and Immunity. Washington D C. *ASM Press* 1999: Pp. 239-296.

13. Morrison S G, Morrison R P. Resolution of secondary *Chlamydia trachomatis* genital tract infection in immune mice with depletion of both CD4+ and CD8+ T cells. *Infect Immun* 2001, 69(4): 2643-2649.

14. Moore T, Ekworomadu C O, Eko F O, MacMillan L, Ramey K, A nanaba G A, et al. Fc receptor-mediated antibody regulation of T cell immunity against intracellular pathogens. *J Infect Dis* 2003, 188(4): 617-624.

15. Pal S, Rangel J, Peterson E M, de la Maza L M. Immunogenic and protective ability of the two developmental forms of Chlamydiae in a mouse model of infertility. *Vaccine* 1999, 18(7-8): 752-761.

16. Darville T, Hiltke T J. Pathogenesis of genital tract disease due to *Chlamydia trachomatis*. *J Infect Dis* 2010, 201 Suppl 2: S114-125.

17. Hansen J, Jensen K T, Follmann F, Agger E M, Theisen M, Andersen P. Liposome Delivery of *Chlamydia muridarum* Major Outer Membrane Protein Primes a Th1 Response That Protects against Genital Chlamydial Infection in a Mouse Model. *J Infect Dis* 2008, 198(5): 758-767.

18. Olsen A W, Theisen M, Christensen D, Follmann F, Andersen P. Protection against Chlamydia promoted by a subunit vaccine (CTH1) compared with a primary intranasal infection in a mouse genital challenge model. *PLOS One,* 5(5): e10768.

19. Li W, Murthy A K, Guentzel M N, Chambers J P, Forsthuber T G, Seshu J, et al. Immunization with a combination of integral chlamydial antigens and a defined secreted protein induces robust immunity against genital chlamydial challenge. *Infect Immun* 2010, 78(9): 3942-3949.

20. Olsen A W, Follmann F, Hojrup P, Leah R, Sand C, Andersen P, et al. Identification of human T-cell targets recognized during the *Chlamydia trachomatis* genital infection. *J Infect Dis* 2007, 196:1546-1552.

21. Olsen A W, Follmann F, Jensen K, Hojrup P, Leah R, Sorensen H, et al. Identification of C T 521 as a frequent target of Th1 cells in patients with urogenital *Chlamydia trachomatis* infection. *J Infect Dis* 2006, 194(9): 1258-1266.

22. Follmann F, Olsen A W, Jensen K T, Hansen P R, Andersen P, Theisen M. Antigenic profiling of a *Chlamydia trachomatis* gene-expression library. *J Infect Dis* 2008, 197 897-905.

23. Sharma J, Zhong Y, Dong F, Piper J M, Wang G, Zhong G. Profiling of human antibody responses to *Chlamydia trachomatis* urogenital tract infection using microplates arrayed with 156 chlamydial fusion proteins. *Infect Immun* 2006, 74(3): 1490-1499.

24. Coler R N, Bhatia A, Maisonneuve J F, Probst P, Barth B, Ovendale P, et al. Identification and characterization of novel recombinant vaccine antigens for immunization against genital *Chlamydia trachomatis*. *FEMS Immunol Med Microbiol* 2009, 55(2): 258-270.

25. Karunakaran K P, Rey-Ladino J, Stoynov N, Berg K, Shen C, Jiang X, et al. Immunoproteomic discovery of novel T cell antigens from the obligate intracellular pathogen Chlamydia. *J Immunol* 2008, 180(4): 2459-2465.

26. Yu H, Jiang X, Shen C, Karunakaran K P, Brunham R C. Novel *Chlamydia muridarum* T cell antigens induce protective immunity against lung and genital tract infection in murine models. *J Immunol* 2009, 182(3): 1602-1608.

27. Molina D M, Pal S, Kayala M A, Teng A, Kim P J, Baldi P, et al. Identification of immunodominant antigens of *Chlamydia trachomatis* using proteome microarrays. *Vaccine* 2010, 28(17): 3014-3024.

28. Stephens R S, Kalman S, Lammel C, Fan J, Marathe R, Aravind L, et al. Genome sequence of an obligate intracellular pathogen of humans: *Chlamydia trachomatis*. *Science* 1998, 282(5389): 754-759.

29. Sette A, Rappuoli R. Reverse vaccinology: developing vaccines in the era of genomics. *Immunity* 2010, 33(4): 530-541.

30. Igietseme J U, Eko F O, Black C M. Chlamydia vaccines: recent developments and the role of adjuvants in future formulations. *Expert Rev Vaccines* 2011, 10(11): 1585-1596.

31. Rockey D D, Wang J, Lei L, Zhong G. Chlamydia vaccine candidates and tools for chlamydial antigen discovery. *Expert Rev Vaccines* 2009, 8(10): 1365-1377.

32. Farris C M, Morrison R P. Vaccination against *Chlamydia* genital infection utilizing the murine *C. muridarum* model. *Infect Immun* 2011, 79(3): 986-996.

33. Kubo A, Stephens R S. Characterization and functional analysis of PorB, a Chlamydia porin and neutralizing target. *Mol Microbiol* 2000, 38(4): 772-780.

34. Kawa D E, Schachter J, Stephens R S. Immune response to the *Chlamydia trachomatis* outer membrane protein PorB. *Vaccine* 2004, 22(31-32): 4282-4286.

35. Crane D D, Carlson J H, Fischer E R, Bavoil P, Hsia R C, Tan C, et al. *Chlamydia trachomatis* polymorphic membrane protein D is a species-common pan-neutralizing antigen. *Proc Natl Acad Sci USA* 2006, 103(6): 1894-1899.

36. Baehr W, Zhang Y X, Joseph T, Su H, Nano F E, Everett K D, et al. Mapping antigenic domains expressed by *Chlamydia trachomatis* major outer membrane protein genes. *Proc Natl Acad Sci USA* 1988, 85(11): 4000-4004.

37. Bavoil P, Ohlin A, Schachter J. Role of disulfide bonding in outer membrane structure and permeability in *Chlamydia trachomatis. Infect Immun* 1984, 44(2): 479-485.

38. Hatch T P, Allan I, Pearce J H. Structural and polypeptide differences between envelopes of infective and reproductive life cycle forms of *Chlamydia* spp.) *Bacteriol* 1984, 157(1): 13-20.

39. Stephens R S, Sanchez-Pescador R, Wagar E A, Inouye C, Urdea M S. Diversity of *Chlamydia trachomatis* major outer membrane protein genes. *J Bacteriol* 1987, 169(9): 3879-3885.

40. Caldwell H D, Perry L J. Neutralization of *Chlamydia trachomatis* infectivity with antibodies to the major outer membrane protein. *Infect Immun* 1982, 38(2): 745-754.

41. Peeling R, Maclean I W, Brunham R C. In vitro neutralization of *Chlamydia trachomatis* with monoclonal antibody to an epitope on the major outer membrane protein. *Infect Immun* 1984, 46(2): 484-488.

42. Zhang Y X, Stewart S, Joseph T, Taylor H R, Caldwell H D. Protective monoclonal antibodies recognize epitopes located on the major outer membrane protein of *Chlamydia trachomatis. J Immunol* 1987, 138(2): 575-581.

43. Zhang Y X, Stewart S J, Caldwell H D. Protective monoclonal antibodies to *Chlamydia trachomatis* serovar- and serogroup-specific major outer membrane protein determinants. *Infect Immun* 1989, 57(2): 636-638.

44. Cotter T W, Meng Q, Shen Z L, Zhang Y X, Su H, Caldwell H D. Protective efficacy of major outer membrane protein-specific immunoglobulin A (IgA) and IgG monoclonal antibodies in a murine model of *Chlamydia trachomatis* genital tract infection. *Infect Immun* 1995, 63(12): 4704-4714.

45. Bandea C I, Debattista J, Joseph K, Igietseme J, Timms P, Black C M. *Chlamydia trachomatis* serovars among strains isolated from members of rural indigenous communities and urban populations in Australia. *J Clin Microbiol* 2008, 46(1): 355-356.

46. Hsu M C, Tsai P Y, Chen K T, Li L H, Chiang C C, Tsai J J, et al. Genotyping of *Chlamydia trachomatis from clinical specimens in Taiwan. J Med Microbiol* 2006, 55 (Pt 3): 301-308.

47. Jonsdottir K, Kristjansson M, Hjaltalin Olafsson J, Steingrimsson O. The molecular epidemiology of genital *Chlamydia trachomatis* in the greater Reykjavik area, Iceland. *Sex Transm Dis* 2003, 30(3): 249-256.

48. Lysen M, Osterlund A, Rubin C J, Persson T, Persson I, Herrmann B. Characterization of ompA genotypes by sequence analysis of DNA from all detected cases of *Chlamydia trachomatis* infections during 1 year of contact tracing in a Swedish County. *J Clin Microbiol* 2004, 42(4): 1641-1647.

49. Millman K, Black C M, Johnson R E, Stamm W E, Jones R B, Hook E W, et al. Population-based genetic and evolutionary analysis of *Chlamydia trachomatis* urogenital strain variation in the United States. *J Bacteriol* 2004, 186(8): 2457-2465.

50. Millman K, Black C M, Stamm W E, Jones R B, Hook E W, 3rd, Martin D H, et al. Population-based genetic epidemiologic analysis of *Chlamydia trachomatis* serotypes and lack of association between ompA polymorphisms and clinical phenotypes. *Microbes Infect* 2006, 8(3): 604-611.

51. Su H, Parnell M, Caldwell H D. Protective efficacy of a parenterally administered MOM P-derived synthetic oligopeptide vaccine in a murine model of *Chlamydia trachomatis* genital tract infection: serum neutralizing IgG antibodies do not protect against chlamydial genital tract infection. *Vaccine* 1995, 13(11): 1023-1032.

52. Pal S, Barnhart K M, Wei Q, A bai A M, Peterson E M, de la Maza L M. Vaccination of mice with DNA plasmids coding for the *Chlamydia trachomatis* major outer membrane protein elicits an immune response but fails to protect against a genital challenge. *Vaccine* 1999, 17(5): 459-465.

53. Zhang D J, Yang X, Shen C, Brunham R C. Characterization of immune responses following intramuscular DNA immunization with the MOM P gene of *Chlamydia trachomatis* mouse pneumonitis strain. *Immunology* 1999, 96(2): 314-321.

54. Pal S, Theodor I, Peterson E M, de la Maza L M. Immunization with the *Chlamydia trachomatis* mouse pneumonitis major outer membrane protein can elicit a protective immune response against a genital challenge. *Infect Immun* 2001, 69(10): 6240-6247.

55. Shaw J, Grund V, Durling L, Crane D, Caldwell H D. Dendritic cells pulsed with a recombinant chlamydial major outer membrane protein antigen elicit a CD4 (+) type 2 rather than type 1 immune response that is not protective. *Infect Immun* 2002, 70(3): 1097-1105.

56. Kari L, Whitmire W M, Crane D D, Reveneau N, Carlson J H, Goheen M M, et al. *Chlamydia trachomatis* native major outer membrane protein induces partial protection in nonhuman primates: implication for a trachoma transmission-blocking vaccine. *J Immunol* 2009, 182(12): 8063-8070.

57. Carmichael J R, Pal S, Tifrea D, de la Maza L M. Induction of protection against vaginal shedding and infertility by a recombinant *Chlamydia* vaccine. *Vaccine* 2011, 29(32): 5276-5283.

58. Y en T Y, Pal S, de la Maza L M. Characterization of the disulfide bonds and free cysteine residues of the *Chlamydia trachomatis* mouse pneumonitis major outer membrane protein. *Biochemistry* 2005, 44(16): 6250-6256.

59. Stephens R S, Wagar E A, Schoolnik G K. High-resolution mapping of serovar-specific and common antigenic determinants of the major outer membrane protein of *Chlamydia trachomatis. J Exp Med* 1988, 167(3): 817-831.

60. Murdin A D, Su H, Klein M H, Caldwell H D. Poliovirus hybrids expressing neutralization epitopes from variable domains I and I V of the major outer membrane protein of *Chlamydia trachomatis* elicit broadly cross-reactive C. *trachomatis*-neutralizing antibodies. *Infect Immun* 1995, 63(3): 1116-1121.

61. Murdin A D, Su H, Manning D S, Klein M H, Parnell M J, Caldwell H D. A poliovirus hybrid expressing a neutralization epitope from the major outer membrane protein of *Chlamydia trachomatis* is highly immunogenic. *Infect Immun* 1993, 61(10): 4406-4414.

62. Villeneuve A, Brossay L, Paradis G, Hebert J. Determination of neutralizing epitopes in variable domains I and I V of the major outer-membrane protein from *Chlamydia trachomatis* serovar K. Microbiology 1994, 140 (Pt 9): 2481-2487.

63. Villeneuve A, B rossay L, Paradis G, Hebert J. Characterization of the humoral response induced by a synthetic peptide of the major outer membrane protein of *Chlamydia trachomatis* serovar B. *Infect Immun* 1994, 62(8): 3547-3549.

64. Motin V L, de la Maza L M, Peterson E M. Immunization with a peptide corresponding to chlamydial heat shock protein 60 increases the humoral immune response in C3H mice to a peptide representing variable domain 4 of the major outer membrane protein of *Chlamydia tra-chomatis. Clin Diagn Lab Immunol* 1999, 6(3): 356-363.

65. Su H, Caldwell H D. Immunogenicity of a synthetic oligopeptide corresponding to antigenically common T-helper and B-cell neutralizing epitopes of the major outer membrane protein of *Chlamydia trachomatis. Vaccine* 1993, 11(11): 1159-1166.

66. Toye B, Zhong G M, Peeling R, Brunham R C. Immunologic characterization of a cloned fragment containing the species-specific epitope from the major outer membrane protein of *Chlamydia trachomatis. Infect Immun* 1990, 58(12): 3909-3913.

67. Mygind P, Christiansen G, Persson K, Birkelund S. Detection of *Chlamydia trachomatis*-specific antibodies in human sera by recombinant major outer-membrane protein polyantigens. *J Med Microbiol* 2000, 49(5): 457-465.

68. Qu Z, Cheng X, de la Maza L M, Peterson E M. Analysis of the humoral response elicited in mice by a chimeric peptide representing variable segments I and I V of the major outer membrane protein of *Chlamydia trachomatis. Vaccine* 1994, 12(6): 557-564.

69. Peterson E M, Cheng X, Qu Z, de la Maza L M. The effect of orientation within a chimeric peptide on the immunogenicity of *Chlamydia trachomatis* epitopes. *Mol Immunol* 1996, 33(4-5): 335-339.

70. Caldwell H D, Kromhout J, Schachter J. Purification and partial characterization of the major outer membrane protein of *Chlamydia trachomatis. Infect Immun* 1981, 31(3): 1161-1176.

71. Ravn P, Demissie A, Eguale T, Wondwosson H, Lein D, A moudy H A, et al. Human T cell responses to the ESAT-6 antigen from *Mycobacterium tuberculosis. J Infect Dis* 1999, 179(3): 637-645.

72. Stryhn A, Pedersen L O, Romme T, Holm C B, Holm A, Buus S. Peptide binding specificity of major histocompatibility complex class I resolved into an array of apparently independent subspecificities: quantitation by peptide libraries and improved prediction of binding. *Eur J Immunol* 1996, 26(8): 1911-1918.

73. Harboe M, Oettinger T, Wiker H G, Rosenkrands I, Andersen P. Evidence for occurrence of the ESAT-6 protein in *Mycobacterium tuberculosis* and virulent *Mycobacterium bovis* and for its absence in *Mycobacterium bovis* BCG. *Infect Immun* 1996, 64(1): 16-22.

74. Volp K, Mathews S, Timms P, Hafner L. Peptide immunization of guinea pigs against *Chlamydia psittaci* (GPIC agent) infection induces good vaginal secretion antibody response, in vitro neutralization and partial protection against live challenge. *Immunol Cell Biol* 2001, 79(3): 245-250.

75. Hinton H J, Jegerlehner A, Bachmann M F. Pattern recognition by B cells: the role of antigen repetitiveness versus Toll-like receptors. *Current topics in microbiology and immunology* 2008, 319:1-15.

76. Kim S K, DeM ars R. Epitope clusters in the major outer membrane protein of *Chlamydia trachomatis. Curr Opin Immunol* 2001, 13(4): 429-436.

77. Findlay H E, McClafferty H, Ashley R H. Surface expression, single-channel analysis and membrane topology of recombinant *Chlamydia trachomatis* Major Outer Membrane Protein. *BMC Microbiol* 2005, 5:5.

78. Cobbold S P, Jayasuriya A, Nash A, Prospero T D, Waldmann H. Therapy with monoclonal antibodies by elimination of T-cell subsets in vivo. *Nature* 1984, 312 (5994): 548-551.

79. Qin S, Cobbold S, Tighe H, Benjamin R, Waldmann H. CD4 monoclonal antibody pairs for immunosuppression and tolerance induction. *Eur J Immunol* 1987, 17(8): 1159-1165.

U.S. patent application Ser. No. 15/956,731, filed Apr. 18, 2018, U.S. patent application Ser. No. 14/216,403, filed Mar. 17, 2014, U.S. Provisional Patent Application No. 61/802, 907, filed Mar. 18, 2013, Danish Patent Application Nos. PA 2013 00155, filed Mar. 18, 2013, and PA 2013 00684, Dec. 11, 2013, including sequence listings, are incorporated herein by reference in their entireties.

The invention claimed is:

1. A nucleic acid encoding a polypeptide comprising 3 or more immuno-repeat units of surface exposed fragments of a *Chlamydia* major outer membrane protein (MOMP), each of said immune-repeat units comprising an amino acid sequence from a variable domain 4 (VD4) region selected from:

VD4-SvD (SEQ ID NO: 15);
VD4-SvE (SEQ ID NO: 16);
VD4-SvF (SEQ ID NO: 17);
VD4-Svla (SEQ ID NO: 18);
VD4-SvG (SEQ ID NO: 19);
VD4-SvJ (SEQ ID NO: 20);
VD4$^{ext}$SvD (SEQ ID NO: 23);
VD4$^{ext}$SvE (SEQ ID NO: 24);
VD4$^{ext}$SvF (SEQ ID NO: 25);
VD4$^{ext}$SvG (SEQ ID NO: 26);
VD4$^{ext}$Svla (SEQ ID NO: 27);
VD4$^{ext}$SvJ (SEQ ID NO: 28), wherein each of said at least 3 or more immuno-repeat units is from a different serovar, wherein optionally the cysteine residue in SEQ ID Nos: 17-18, 25-26 is substituted with serine to prevent formation of a disulfide bond.

2. The nucleic acid according to claim 1, wherein said polypeptide further comprises at least one immuno-repeat amino acid sequence from a variable domain 1 (VD1) region selected from:

VD1-SvD (SEQ ID NO: 1);
VD1-SvE (SEQ ID NO: 2);
VD1-SvF (SEQ ID NO: 3);
VD1-Svla (SEQ ID NO: 4);
VD1-SvG (SEQ ID NO: 5);
VD1-SvJ (SEQ ID NO: 6);
VD1$^{ext}$SvD (SEQ ID NO:9);
VD1$^{ext}$SVE (SEQ ID NO: 10);
VD1$^{ext}$SvF (SEQ ID NO:11);
VD1$^{ext}$SvG (SEQ ID NO: 12):
VD1$^{ext}$Svla (SEQ ID NO: 13) and
VD1$^{ext}$SvJ (SEQ ID NO: 14).

3. The nucleic acid according to claim 2, wherein the encoded polypeptide comprises the at least 3 VD4 regions, and the at least one VD1 region of the MOMP placed next to each other.

4. The nucleic acid of claim 2, further comprising a linked nucleic acid encoding a moiety that facilitates export of the polypeptide when produced recombinantly, a moiety that facilitates purification of the encoded polypeptide, or a moiety which enhances immunogenicity, wherein said moiety which enhances immunogenicity is a T-cell target selected from *Chlamydia trachomatis* (Ct) antigens CT043, CT004, CT414, and CT681.

5. The nucleic acid according to claim 4, wherein said encoded polypeptide has an amino acid sequence of SEQ ID NO: 60.

6. A pharmaceutical composition comprising the nucleic acid of claim 5, and one or more of a pharmacologically acceptable carrier, excipient, adjuvant, and immune modulator, wherein said nucleic acid is DNA or RNA.

7. The nucleic acid according to claim 1, wherein the VD4 immuno-repeat units comprise at least serovars D, E and F.

8. The nucleic acid according to claim 1, wherein said encoded polypeptide comprises i) an N terminal sequence of SEQ ID NO: 21 or a subsequence thereof, said subsequence comprising 1-38 amino acid residues, starting with the C-terminal K in the amino acid sequence in SEQ ID NO: 21 and ii) a C-terminal sequence of SEQ ID NO: 22 or a subsequence thereof, said subsequence comprising 1-29 amino acid residues, starting with the N-terminal D in SEQ ID NO: 22.

9. The nucleic acid according to claim 1, where said encoded polypeptide comprises the amino acid sequence selected from SEQ ID NO: 46, 47, 48, 53, 54, 55, 60, 64, 65, 66, 67, 69 and 70.

10. The nucleic acid according to claim 1, further comprising a linked nucleic acid encoding a moiety that facilitates export of the polypeptide when produced recombinantly, a moiety that facilitates purification of said encoded polypeptide, or a moiety which enhances immunogenicity.

11. The nucleic acid according to claim 10, wherein said moiety which enhances immunogenicity is a T-cell target selected from *Chlamydia trachomatis* (Ct) antigens CT043, CT004, CT414, and CT681.

12. The nucleic acid according to claim 11, wherein said encoded polypeptide has an amino acid sequence selected from SEQ ID NO: 64, 65, 66 and 67.

13. A pharmaceutical composition comprising the nucleic acid of claim 12 and one or more of a pharmacologically acceptable carrier, excipient, adjuvant, and immune modulator, wherein said nucleic acid is DNA or RNA.

14. A pharmaceutical composition comprising the nucleic acid of claim 12 which encodes a polypeptide of SEQ ID NO: 64 and one or more of a pharmacologically acceptable carrier, excipient, adjuvant, and immune modulator, wherein said nucleic acid is DNA or RNA.

15. The nucleic acid according to claim 1, wherein said nucleic acid is DNA or RNA.

16. A pharmaceutical composition comprising the nucleic acid according to claim 1 and one or more of a pharmacologically acceptable carrier, excipient, adjuvant, and immune modulator, wherein said nucleic acid is DNA or RNA.

* * * * *